US010093922B2

(12) United States Patent
Zieler

(10) Patent No.: US 10,093,922 B2
(45) Date of Patent: *Oct. 9, 2018

(54) COMPOSITIONS AND METHODS FOR CREATING ALTERED AND IMPROVED CELLS AND ORGANISMS

(71) Applicant: Helge Zieler, Encinitas, CA (US)

(72) Inventor: Helge Zieler, Encinitas, CA (US)

(*) Notice: Subject to any disclaimer, the term of this patent is extended or adjusted under 35 U.S.C. 154(b) by 406 days.

This patent is subject to a terminal disclaimer.

(21) Appl. No.: 14/653,840

(22) PCT Filed: Dec. 19, 2013

(86) PCT No.: PCT/US2013/076526
§ 371 (c)(1),
(2) Date: Jun. 18, 2015

(87) PCT Pub. No.: WO2014/100400
PCT Pub. Date: Jun. 26, 2014

(65) Prior Publication Data
US 2015/0329853 A1 Nov. 19, 2015

Related U.S. Application Data

(60) Provisional application No. 61/739,671, filed on Dec. 19, 2012, provisional application No. 61/761,175, filed on Feb. 5, 2013.

(51) Int. Cl.
*C12N 15/10* (2006.01)
*C12N 15/81* (2006.01)
*C12N 15/70* (2006.01)
*C07H 21/02* (2006.01)

(52) U.S. Cl.
CPC ......... *C12N 15/1082* (2013.01); *C07H 21/02* (2013.01); *C12N 15/102* (2013.01); *C12N 15/1027* (2013.01); *C12N 15/70* (2013.01); *C12N 15/81* (2013.01)

(58) Field of Classification Search
CPC .............................. C12N 15/1082; C07H 21/02
USPC .............................................................. 506/9
See application file for complete search history.

(56) References Cited

U.S. PATENT DOCUMENTS

| 6,156,511 | A | 12/2000 | Schatz et al. |
| 6,645,766 | B2 | 11/2003 | Luo et al. |
| 7,846,712 | B2 | 12/2010 | Zhang et al. |
| 2001/0003650 | A1 | 6/2001 | Anderson et al. |
| 2010/0055125 | A1 | 3/2010 | Jungbauer et al. |

(Continued)

FOREIGN PATENT DOCUMENTS

WO 0130998 A1 5/2001

OTHER PUBLICATIONS

Albertson, L et al., Appl. Environ. Microbiol., 2011, vol. 77, No. 3, pp. 1033-1040.

(Continued)

*Primary Examiner* — Karla A Dines
(74) *Attorney, Agent, or Firm* — Gorman IP Law, APC

(57) ABSTRACT

The present invention provides compositions comprising randomized in-frame fusion polynucleotides and methods for introducing them into a host organism to identify desirable phenotypic changes that disrupt or alter existing genetic or biochemical mechanisms or pathways, thus creating novel characteristics of the transformed organism. Methods for using the compositions for increasing diversity within populations of organisms are also presented.

16 Claims, 11 Drawing Sheets
Specification includes a Sequence Listing.

(56) References Cited

U.S. PATENT DOCUMENTS

2011/0166868 A1   7/2011   Muir et al.
2014/0186915 A1   7/2014   Mori

OTHER PUBLICATIONS

Chen, X et al., Adv. Drug Deliv. Rev., Sep. 2012, vol. 65, pp. 1357-1369.
Hvorency, KL and Prelich, G, Yeast, 2010, vol. 27, pp. 861-865.
Jin, Y et al., Appl. Environ. Microbiol., 2005, vol. 71, pp. 8249-8256.
Nevoigt, E Microbiol. Mol. Biol. Rev, 2008, vol. 72, No. 3, pp. 379-412.
Rajagopala, SV et al., BMC Genomics, 2010, vol. 11, Ar. No. 470, pp. 1-8.
Tokuhiro, K et al., Appl. Environ. Microbiol., 2009, vol. 75, No. 17, pp. 5536-5543.
Wang, R et al., Enzyme and Microb. Technol., 2010, vol. 47, pp. 194-199.
Yilmaz, JL and Bulow, L., Biotechnol. Prog., 2002, vol. 18, pp. 1176-1182.
Babushok et al. Current topics in genome evolution: molecular mechanisms of new gene formation. Cell Mol Life Sci. 2007; 64(5):542-54.
Beekwilder et al. A phagemid vector using the *E. coli* phage shock promoter facilitates phage display of toxic proteins. Gene 1999; 228(1-2): 23-31.
Li and Elledge. Harnessing homologous recombination in vitro to generate recombinant DNA via SLIC. Nat Methods. 2007; 4(3): 251-256.
Lobban and Kaiser. Enzymatic end-to end joining of DNA molecules. J Mol Biol. 1973; 78(3): 453-471.
[Oliver et al. Cyanobacterial conversion of carbon dioxide to 2,3-butanediol. Proc Natl Acad Sci U S A. 2013; 110 (4):1249-1254.
Alper et al. Engineering yeast transcription machinery for improved ethanol tolerance and production. Science 2006; 314:1565-1568.
Anderson, J. et al., BglBricks: A flexible standard for biological part assembly, Jan. 20, 2010, Journal of Biological Engineering, 4:1-12.
Andersson et al. Application of bioluminescence to the study of circadian rhythms in cyanobacteria. Methods Enzymol. 2000; 305:527-542.
Arai et al. Design of the linkers which effectively separate domains of a bifunctional fusion protein. Protein Engineering 2001; 14 (8): 529-532.
Ashby and Houmard. Cyanobacterial two-component proteins: structure, diversity, distribution, and evolution. Microbiol Mol Biol Rev. 2006; 70(2):472-509.
Aslanidis and DeJong. Ligation-independent cloning of PCR products (LI-PCR). Nucl Acids Res 18 1990; (20): 6069-6074.
Aslanidis et al. Minimal length requirement of the single-stranded tails for ligation-independent cloning (LIC) of PCR products. PCR Methods Appl 1994;. 4(3): 172-177.
Atsumi et al. Evolution, genomic analysis, and reconstruction of isobutanol tolerance in *Escherichia coli*. Mol Syst Biol 2012; 6:449.
Atsumi et al. Direct photosynthetic recycling of carbon dioxide to isobutyraldehyde. Nat Biotechnol. 2009; 27 (12):1177-1180.
Baer et al. Effect of butanol challenge and temperature on lipid composition and membrane fluidity of butanol tolerant Clostridium acetobutylicum. Appl Environ Microbiol 1987; 53:2854-2861.
Belyaeva et al. The *Escherichia coli* cysG promoter belongs to the 'extended-10' class of bacterial promoters. Biochem. J. 1993; 296 (Pt 3): 851-857.
Brachmann et al. Designer deletion strains derived from *Saccharomyces cerevisiae* S288C: a useful set of strains and plasmids for PCR-mediated gene disruption and other applications. Yeast 1998; 14(2):115-132.
Brissette et al. Phage shock protein, a stress protein of *Escherichia coli*. Proc Natl Acad Sci U S A 1990; 87(3): 862-866.
Brissette et al. Characterization and sequence of the *Escherichia coli* stress-induced psp operon. J Mol Biol.1991; 220(1): 35-48.
Bustos and Golden. Expression of the psbDII gene in *Synechococcus* sp. strain PCC 7942 requires sequences downstream of the transcription start site. J Bacteriol. 1991; 173(23):7525-7533.
Bustos and Golden. Light-regulated expression of the psbD gene family in *Synechococcus* sp. strain PCC 7942: evidence for the role of duplicated psbD genes in cyanobacteria. Mol Gen Genet. 1992; 232(2):221-230.
Chenna et al. Multiple sequence alignment with the Clustal series of programs. Nucleic Acids Res. 2003; 31 (13):3497-3500.
Clerico et al. Specialized techniques for site-directed mutagenesis in cyanobacteria. Methods Mol Biol. 2007; 362:155-171.
Dahl et al. Multiplex amplification enabled by selective circularization of large sets of genomic DNA fragments. Nucleic Acids Res. 2005; 33(8): e71.
De Mey et al. Construction and model-based analysis of a promoter library for *E-coli*: an indispensable tool for metabolic engineering BMC Biotechnol. 2007; 7: 34.
Degryse et al. In vivo cloning by homologous recombination in yeast using a two-plasmid-based system. Yeast 1995; 11(7):629-640.
Deng and Coleman. Ethanol synthesis by genetic engineering in cyanobacteria. Appl Environ Microbiol.1999; 65 (2):523-528.
Dexter and Fu. Metabolic engineering of cyanobacteria for ethanol production. Energy Environ. Sci. 2009; 2 (8):857-864.
Ding et al. Tolerance and stress response to ethanol in the yeast *Saccharomyces cerevisiae*. Appl Microbiol Biotechnol. 2009; 85(2):253-263.
Dismukes et al. Aquatic phototrophs: efficient alternatives to land-based crops for biofuels. Curr Opin Biotechnol. 2008; 19(3):235-240.
Dolganov and Grossman. Insertional inactivation of genes to isolate mutants of *Synechococcus* sp. strain PCC 7942: isolation of filamentous strains. J Bacteriol. 1993; 175(23):7644-7651.
Ducat et al. Engineering cyanobacteria to generate high-value products. Trends Biotechnol. 2011; 29(2):95-103.
Ducat et al. Rerouting carbon flux to enhance photosynthetic productivity. Appl Environ Microbiol. 2012; 78 (8):2660-2668.
Dunlop et al. Engineering microbial biofuel tolerance and export using efflux pumps. Mol Syst Biol 2011; 7:487.
Dunlop. Engineering microbes for tolerance to next-generation biofuels. Biotechnol Biofuels 2011; 4:32.
Dymond, J et al., Synthetic chromosome arms function in yeast and generate phenotypic diversity by design, Sep. 22, 2011, Nature, 477:471-476.
Eisenbeis and Höcker . Evolutionary mechanism as a template for protein engineering. J Pept Sci. 2010; 16 (10): 538-544.
Eldridge et al. An in vitro selection strategy for conferring protease resistance to ligand binding peptides. Protein Eng Des Sel. 2009; 22(11):691-8.
Elhai. Genetic techniques appropriate for the biotechnological exploitation of cyanobacteria. J. Appl. Phycol. 1994; 6 (2):177-186.
Elsaesser and Paysan. Liquid gel amplification of complex plasmid libraries. Biotechniques 2004; 37(2):200-202.
Elsharawy et al. Accurate variant detection across non-amplified and whole genome amplified DNA using targeted next generation sequencing. BMC Genomics 2012; 13(1):500.
Flores et al. Gene transfer to cyanobacteria in the laboratory and in nature. In: Herrero A, Flores E, eds. The cyanobacteria: molecular biology, genomics and evolution. 2008. Norfolk, UK: Caister Academic Press. pp. 45-57.
Fullwood et al. The use of multiple displacement amplification to amplify complex DNA libraries. Nucleic Acids Res. 2008; 36(5):e32.
Funk et al. Vector systems for heterologous expression of proteins in *Saccharomyces cerevisiae*. Methods Enzymol. 2002; 350:248-57.
Gao et al. Photosynthetic production of ethanol from carbon dioxide in genetically engineered cyanobacteria. Energy Environ. Sci. 2012; 5(12):9857-9865.
Geerts et al. Inducible expression of heterologous genes targeted to a chromosomal platform in the cyanobacterium *Synechococcus* sp. PCC 7942. Microbiology 1995; 141(4):831-841.

(56) References Cited

OTHER PUBLICATIONS

Gibson et al. Chemical synthesis of the mouse mitochondrial genome. Nat Methods. 2010; 7(11):901-903.
Gibson et al. Enzymatic assembly of DNA molecules up to several hundred kilobases. Nat Methods 2009;. 6 (5):343-345.
Gietz and Schiestl. High-efficiency yeast transformation using the LiAc/SS carrier DNA/PEG method. Nat Protocols 2007; 2(1):31-34.
Gietz and Woods. Yeast transformation by the LiAc/SS Carrier DNA/PEG method. Methods Mol Biol. 2006; 313:107-120.
Natsoulis et al. A flexible approach for highly multiplexed candidate gene targeted resequencing. PLoS One 2011; ' 6(6):e21088.
Newberger et al. The Human OligoGenome Resource: a database of oligonucleotide capture probes for resequencing target regions across the human genome. Nucleic Acids Res. 2012; 40(Database issue):D1137-1143.
Quan and Tian. Circular polymerase extension cloning for high-throughput cloning of complex and combinatorial DNA libraries. Nat Protoc. 2011; 6(2):242-251.
Quan and Tian. Circular polymerase extension cloning of complex gene libraries and pathways. PLoS One. 2009; 4 (7): e6441.
Rabbitts. Commonality but diversity in cancer gene fusions. Cell 2009; 137(3):391-395.
Raymond et al. General method for plasmid construction using homologous recombination. Biotechniques 1999; 26 (1):134-8, 140-1.
Raymond et al. Linker-mediated recombinational subcloning of large DNA fragments using yeast. Genome Res 2002;. 12(1):190-197.
Robertson et al. A new dawn for industrial photosynthesis. Photosynth Res. 2011; 107(3):269-277.
Ruffing. Engineered cyanobacteria: teaching an old bug new tricks. Bioeng Bugs.2011; 2(3):136-149.
Sambrook et al. Molecular Cloning: A Laboratory Manual, Second Ed., 1989. Cold Spring Harbor Laboratory Press,10 Plainview, New York.
Sawyers. The bcr-abl gene in chronic myelogenous leukaemia. Cancer Surv. 1992; 15:37-51.
Shao et al. DNA assembler, an in vivo genetic method for rapid construction of biochemical pathways. Nucleic Acids Res. 2009; 37(2):e16.
Shizuya et al. Cloning and stable maintenance of 300-kilobase-pair fragments of human DNA in *Escherichia coli* using an F-factor-based vector. Proc Natl Acad Sci U S A 1992; 89(18): 8794-8797.
Steen et al. Metabolic engineering of *Saccharomyces cerevisiae* for the production of n-butanol. Microb Cell Fact. 2008; 7:36.
Stemmer DNA shuffling by random fragmentation and reassembly: in vitro recombination for molecular evolution. Proc Natl Acad Sci USA 1994; 91(22):10747-10751.
Stemmer. Rapid evolution of a protein in vitro by DNA shuffling. Nature 1994; 370(6488):389-391.
Takahama et al. Construction and analysis of a recombinant cyanobacterium expressing a chromosomally inserted gene for an ethylene-forming enzyme at the psbAI locus. J Biosci Bioeng. 2003; 95(3):302-305.
Tan et al. Photosynthesis driven conversion of carbon dioxide to fatty alcohols and hydrocarbons in cyanobacteria. Metab Eng. 2011; 13(2):169-176.
Tewhey et al. Microdroplet-based PCR enrichment for large-scale targeted sequencing. Nat Biotechnol. 2009; 27 (11):1025-1031.
Thieme et al. Quick and clean cloning: a ligation-independent cloning strategy for selective cloning of specific PCR products from non-specific mixes. PLoS One 2011; 6(6): e20556.
Thomas et al. Overexpression of groESL in Clostridium acetobutylicum results in increased solvent production and tolerance, prolonged metabolism, and changes in the cell's transcriptional program. Appl Environ Microbiol 2003; 69:4951-4965.
Tian et al. Quantitative proteomics reveals dynamic responses of *Synechocystis* sp. PCC 6803 to next-generation biofuel butanol. J Proteomics 2013; 78:326-345.

Tsinoremas et al. Efficient gene transfer in *Synechococcus* sp. strains PCC 7942 and PCC 6301 by interspecies conjugation and chromosomal recombination. J Bacteriol. 1994; 176(21):6764-6768.
Vieira and Messing. The pUC plasmids, an M13mp7-derived system for insertion mutagenesis and sequencing with synthetic universal primers. Gene 1982; 19(3):259-268.
Vioque. Transformation of cyanobacteria. Adv Exp Med Biol. 2007; 616:12-22.
Vroom and Wang. Modular construction of plasmids through ligation-free assembly of vector components with oligonucleotide linkers. Biotechniques2008; 44(7): 924-926.
Wang et al. Application of synthetic biology in cyanobacteria and algae. Front Microbiol. 2012; 3:344.
Wang et al. Enhancement of engineered trifunctional enzyme by optimizing linker peptides for degradation of agricultural by-products. Enzyme and Microb. Technol.2010; 47 (5): 194-199.
Ward. Single-step purification of shuttle vectors from yeast for high frequency back-transformation into *E. coli*. Nucleic Acids Res. 1990; 8(17):5319.
Weiner et al. Analysis of the proteins and cis-acting elements regulating the stress-induced phage shock protein operon. Nucleic Acids Res.1995; 23(11): 2030-2036.
Weiner et al. Stress-induced expression of the *Escherichia coli* phage shock protein operon is dependent on σ-54 and modulated by positive and negative feedback mechanisms Genes Dev. 1991; 5(10): 1912-1923.
Werner, S et al., Fast track assembly of multigene constructs using Golden Gate cloning and the MoClo system, Jan./Feb. 2012, Bioengineered Bugs 3:1, 38-43.
Whitworth and Cock. Evolution of prokaryotic two-component systems: insights from comparative genomics. Amino Acids 2009; 37(3):459-66.
Wingler and Cornish. Reiterative Recombination for the in vivo assembly of libraries of multigene pathways. Proc Natl Acad Sci U S A. 2011; 108(37):15135-15140.
Zhang and Fisher. The bifunctional enzymes of antibiotic resistance. Curr Opin Microbiol.2009; 12(5):505-511.
Zhao et al. Expression of a cloned cyclopropane fatty acid synthase gene reduces solvent formation in Clostridium acetobutylicum ATCC 824. Appl Environ Microbiol, 2003; 69:2831-2841.
Zhou and Li. Engineering cyanobacteria for fuels and chemicals production. Protein Cell. 1(3):207-210.Lathe R, Kieny MP, Skory S, Lecocq JP (1984). Linker tailing: unphosphorylated linker oligonucleotides for joining DNA termini. DNA 2012; 3(2): 173-182.
Zhou et al. Designing and creating a modularized synthetic pathway in cyanobacterium *Synechocystis* enables production of acetone from carbon dioxide. Metab Eng. 2012; 14(4):394-400.
Zhu et al. In-fusion assembly: seamless engineering of multidomain fusion proteins, modular vectors, and mutations. BioTechniques 2007; 43:354-359.
Kitagawa, M. et al., Complete set of ORF clones *Escherichia coli* ASKA library (A Complete Set of *E. coli* K-12 ORF Archive): Unique Resources for Biological Research, DNA Research, 2005, vol. 12, pp. 291-299.
Rajagopala, S.V. et al., The *Escherichia coli* K-12 ORFeome: a resource for comparative molecular microbiology, BMC Genomics, 2010, vol. 11, Art No. 470, pp. 1-8.
Gietz and Woods. Transformation of yeast by lithium acetate/single-stranded carrier DNA/polyethylene glycol method. Methods Enzymol. 2002; 350:87-96.
Gilbert. Why genes in pieces? Nature 1978; 271(5645):501.
Golden et al. Genetic engineering of the cyanobacterial chromosome. Methods Enzymol. 1987; 153:215-231.
Hammer et al. Synthetic promoter libraries—tuning of gene expression. Trends Biotechnol. 2006; 24 (2): 53-55.
Haun et al. Rapid, reliable ligation-independent cloning of PCR products using modified plasmid vectors. Biotechniques, 1992; 13(4): 515-518.
Heidorn et al. Synthetic biology in cyanobacteria engineering and analyzing novel functions. Methods Enzymol.2011; 497:539-579.
Hong et al. Identification of gene targets eliciting improved alcohol tolerance in *Saccharomyces cerevisiae* through inverse metabolic engineering. J Biotechnol. 2010; 149(1-2):52-59.

(56) References Cited

OTHER PUBLICATIONS

Hoogenboom, H, Selecting and screening recombinant antibody libraries.

Inaki and Liu. Structural mutations in cancer: mechanistic and functional insights. Trends Genet. 2012; 28 (11 ): 550-559.

International Search Report.

International Search Report, dated Apr. 22, 2014.

Irwin et al. In-fusion® cloning with vaccinia virus DNA polymerase. Methods Mol Biol. 2012; 890:23-35.

Ishiura et al. Expression of a gene cluster kaiABC as a circadian feedback process in cyanobacteria. Science 2000; , 281(5382):1519-1523.

Jang et al. Bio-based production of C2-C6 platform chemicals. Biotechnol Bioeng. 2012; 109(10):2437-2459.

Jensen and Hammer. Artificial promoters for metabolic optimization. Biotechnol. Bioengineering 1998; 58 (2-3): 191-195.

Jensen and Hammer. The sequence of spacers between the consensus sequences modulates the strength of prokaryotic promoters. Appl. Environ. Microbiol. 1998; 64 (1): 82-87.

Jia et al. Systematic engineering of microorganisms to improve alcohol tolerance. Engineering in Life Sciences 2009; 10(5): 422-429.

Jovanovic et al. Identification, nucleotide sequence, and characterization of PspF, the transcriptional activator of the *Escherichia coli* stress-induced psp operon. J. Bacteriol. 1996; 178 (7): 1936-1945.

Kamarainen et al. Physiological tolerance and stoichiometric potential of cyanobacteria for hydrocarbon fuel production. J Biotechnol. 2012; 162(1):67-74.

Keefe et al., Functional proteins from a random-sequence library, Nature, Apr. 5, 2001, vol. 410, pp. 715-718.

Knoshaug and Zhang. Butanol tolerance in a selection of microorganisms. Appl Biochem Biotechnol. 2008; 153 (1-3):13-20.

Kondo et al. Circadian rhythms in prokaryotes: luciferase as a reporter of circadian gene expression in cyanobacteria. Proc Natl Acad Sci U S A 1993; 90(12):5672-5676.

Kondo, A and Ueda, M., Yeast cell-surface display—applications of molecular display, 2004, Appl Microbiol Biotechnol 64:28-40.

Kuijpers et al. A versatile, efficient strategy for assembly of multi-fragment expression vectors in *Saccharomyces cerevisiae* using 60 bp synthetic recombination sequences. Microb Cell Fact. 2013; 12:47.

Kulkarni and Golden. mRNA stability is regulated by a coding-region element and the unique 5' untranslated leader sequences of the three Synechococcus psbA transcripts. Mol Microbiol. 1997; 24(6):1131-1142.

Kutsuna et al. A period-extender gene, pex, that extends the period of the circadian clock in the cyanobacterium *Synechococcus* sp. strain PCC 7942. J Bacteriol. 1998; 180(8):2167-2174.

Lan and Liao. Metabolic engineering of cyanobacteria for 1-butanol production from carbon dioxide. Metab Eng. 2011; 13(4):353-63.

Lan and Liao. ATP drives direct photosynthetic production of 1-butanol in cyanobacteria. Proc Natl Acad Sci U S A. 2012; 109(16):6018-6023.

Lathe et al. Linker tailing: unphosphorylated linker oligonucleotides for joining DNA termini. 1984. DNA 3(2): 173-182.

Lee et al. Systems metabolic engineering of microorganisms for natural and non-natural chemicals. Nat Chem Biol. 2012; 8(6):536-546.

Lehnger, "The Molecular Basis of Cell Structure and Function", Biochemistry, Worth Publishers, Inc., New York, NY.

Li and Elledge. SLIC: a method for sequence- and ligation-independent cloning. Methods Mol Biol. 2012; 852:51-59.

Li et al. FastCloning: a highly simplified, purification-free, sequence- and ligation-independent PCR cloning method. BMC Biotechnol. 2011; 11:92.

Liang et al. Activities of constitutive promoters in *Escherichia coli*. J. Mol. Biol. 1999; 292 (1): 19-37.

Lindberg et al. Engineering a platform for photosynthetic isoprene production in cyanobacteria, using Synechocystis as the model organism. Metab Eng. 2010; 12(1):70-79.

Liu and Qureshi. How microbes tolerate ethanol and butanol. New Biotechnol.2009; 26(3-4):117-121.

Liu et al. Proteomic analysis reveals resistance mechanism against biofuel hexane in *Synechocystis* sp. PCC 6803. Biotechnol Biofuels. 2012; 5(1):68.

Liu et al. Fatty acid production in genetically modified cyanobacteria. Proc Natl Acad Sci U S A. 2011; 108 (17):6899-6904.

Ma et al. Plasmid construction by homologous recombination in yeast. Gene 1987; 58(2-3):201-216.

Machado and Atsumi. Cyanobacterial biofuel production. J Biotechnol. 2012; 162(1):50-56.

Marks, J et al. By-passing Immunization Human Antibodies from V-gene Libraries Displayed on Phage, 1991 J. Mol. Biol. 222: 581-597.

Marschalek. Mechanisms of leukemogenesis by Mll fusion proteins. Br J Haematol. 2011; 152(2):141-154.

Mascal. Chemicals from biobutanol: technologies and markets. Biofuels, Bioprod. Bioref. 2012; 6(4):483-493.

Melo. The diversity of BCR-ABL fusion proteins and their relationship to leukemia phenotype. Blood 1996; 88 (7):2375-2384.

Menart et al. Constitutive versus thermoinducible expression of heterologous proteins in *Escherichia coli* based on strong PR,PL promoters from phage lambda. Biotechnology and Bioengineering 2003; 83 (2): 181-190.

Mitelman et al. Fusion genes and rearranged genes as a linear function of chromosome aberrations in cancer. Nat Genet. 2004; 36(4):331-334.

Mitelman et al. The impact of translocations and gene fusions on cancer causation. Nat Rev Cancer 2007; 7 (4):233-245.

Model et al. The *Escherichia coli* phage-shock-protein (psp) operon. Mol Microbiol.1997; 24(2):255-61.

Mutsuda et al. Biochemical properties of CikA, an unusual phytochrome-like histidine protein kinase that resets the circadian clock in Synechococcus elongatus PCC 7942. J Biol Chem 2003; 278(21): 19102-19110.

Myllykangas et al. Targeted sequencing library preparation by genomic DNA circularization. BMC Biotechnol. 2011; 11:122.

Figure 3
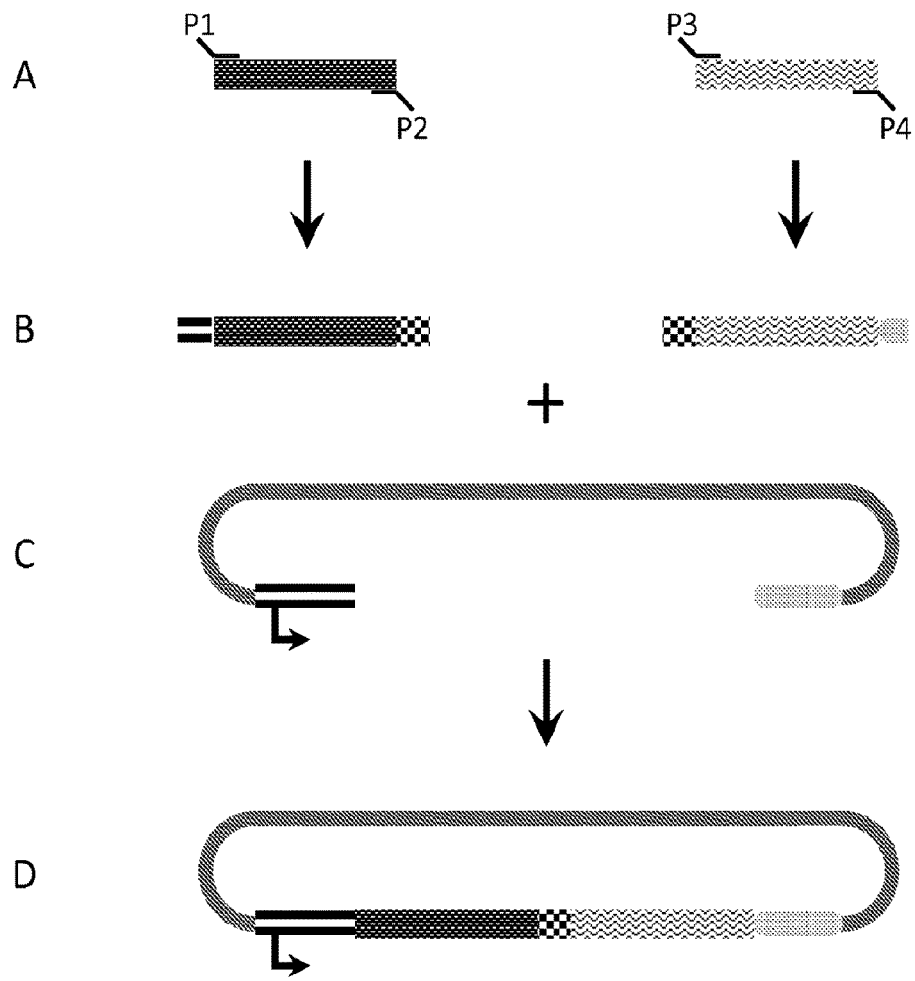
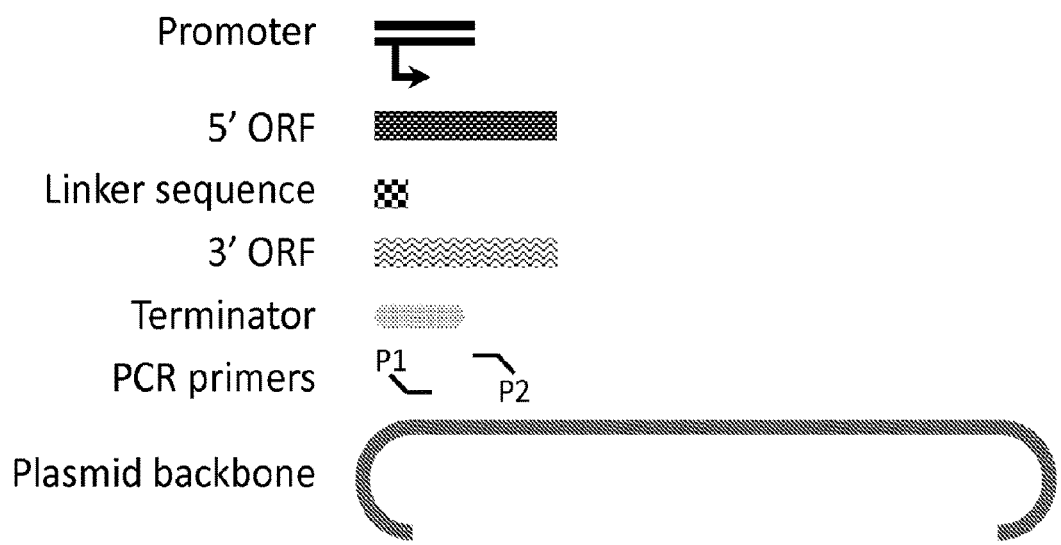

Figure 7
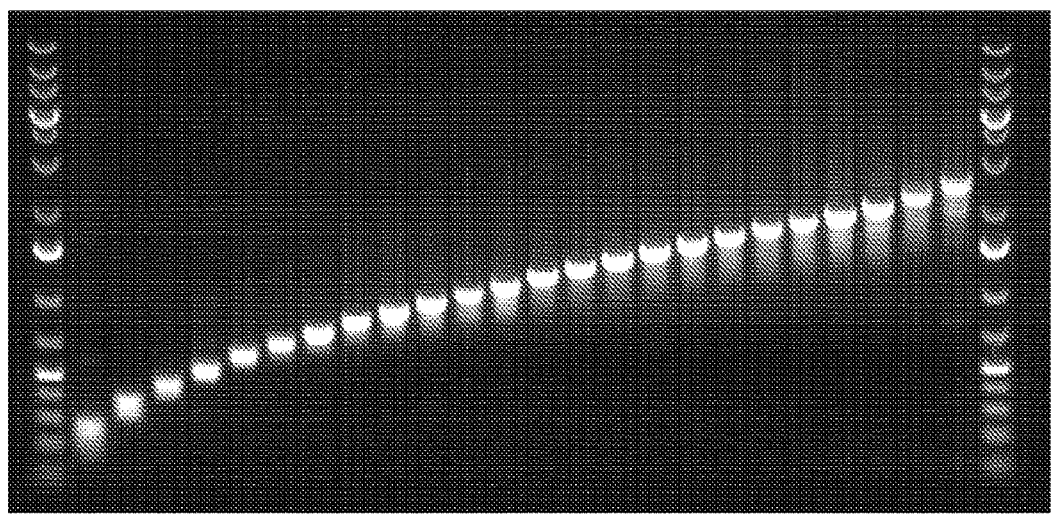
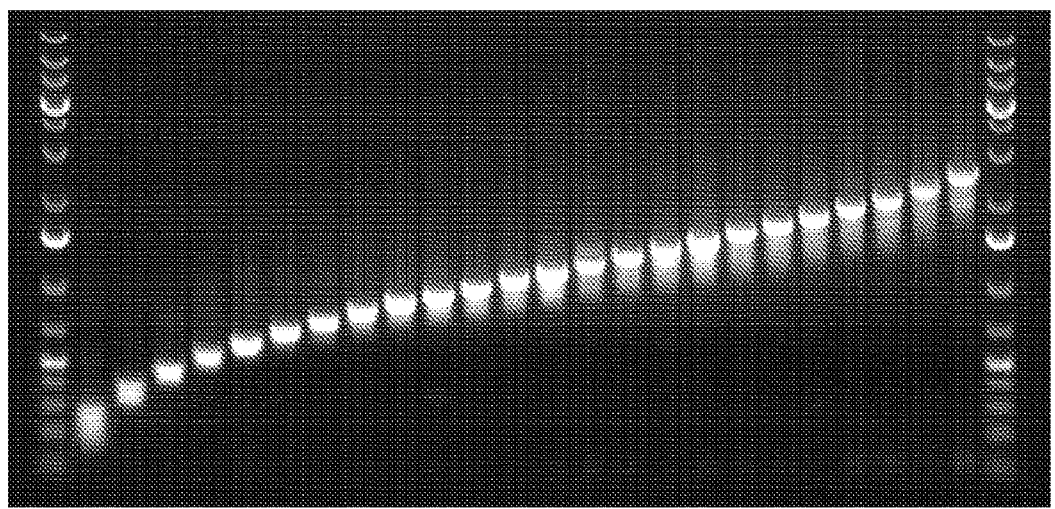

Figure 9

Yeast active fusion genes conferring heat resistance

| Fusion gene name | Fusion gene SEQ ID | 5' ORF SEQ ID | 5' ORF description | 5' ORF length (bp) | 3' ORF description | 3' ORF SEQ ID | 3' ORF length (bp) |
|---|---|---|---|---|---|---|---|
| Y1-5A | 25131 | 108 | Putative protein of unknown function | 198 | General stress response protein | 3444 | 1461 |
| Y1-7A | 25132 | 675 | Putative protein of unknown function | 477 | General stress response protein | 3444 | 1461 |
| Y1-13A | 25133 | 3760 | Dynein intermediate chain | 1599 | General stress response protein | 3444 | 1461 |
| Y1-17A | 25134 | 3444 | General stress response protein | 1458 | Putative protein of unknown function | 1840 | 882 |
| Y1-18A | 25135 | 2338 | Zinc-finger protein of unknown function | 1029 | Oligosaccharyltransferase subunit | 2403 | 1053 |
| Y1-19A | 25136 | 3444 | General stress response protein | 1458 | Telomeric Y' element helicase | 2746 | 1179 |
| Y1-20A | 25137 | 4168 | ER membrane protein | 1815 | General stress response protein | 3444 | 1461 |
| Y1-23A | 25138 | 2746 | Telomeric Y' element helicase | 1176 | General stress response protein | 3444 | 1461 |
| Y1-25A | 25139 | 2005 | C-4 methyl sterol oxidase | 927 | General stress response protein | 3444 | 1461 |
| Y1-28A | 25140 | 731 | Chromatin accessibility complex protein | 501 | General stress response protein | 3444 | 1461 |
| Y1-33A | 25141 | 3561 | Protein of unknown function | 1506 | Regulator of Hsp90 family chaperones | 1153 | 651 |
| Y1-38A | 25142 | 1158 | Component of the EKC/KEOPS complex | 649 | General stress response protein | 3444 | 1461 |
| Y1-39B | 25143 | 13 | Dubious open reading frame | 114 | General stress response protein | 3444 | 1461 |
| Y1-40A | 25144 | 4378 | Putative lipase | 1941 | General stress response protein | 3444 | 1461 |
| Y1-43A | 25145 | 44 | Putative protein of unknown function | 147 | General stress response protein | 3444 | 1461 |
| Y1-45A | 25146 | 1573 | Putative protein of unknown function | 795 | General stress response protein | 3444 | 1461 |
| Y1-47A | 25147 | 1201 | Kinetochore-associated Ndc80 complex | 663 | General stress response protein | 3444 | 1461 |
| Y1-48A | 25148 | 3806 | Multidrug efflux pump | 1626 | General stress response protein | 3444 | 1461 |
| Y1-58B | 25149 | 206 | Lsm (Like Sm) protein | 258 | Stress response ATPase | 4386 | 1950 |
| Y1-58C | 25150 | 575 | Mitochondrial ribosomal protein | 441 | Mitochondrial protein | 4459 | 2010 |
| Y1-66C | 25151 | 815 | Putative protein of unknown function | 534 | Mitochondrial hsp70 chaperone | 4413 | 1974 |
| Y1-67B | 25152 | 2670 | Cellular stress response protein | 1143 | Protein of unknown function | 2558 | 1107 |

Figure 9 (continued)

Yeast active fusion genes conferring heat resistance

| Fusion gene name | Fusion gene SEQ ID | Total fusion protein length (bp) | 5' ORF complete ? | 3' ORF complete ? | In-frame ? | Linker sequence | 5' cloning junction | 3' cloning junction |
|---|---|---|---|---|---|---|---|---|
| Y1-5A | 25131 | 1719 | yes | yes | yes | perfect | perfect | perfect |
| Y1-7A | 25132 | 1998 | yes | yes | yes | perfect | perfect | perfect |
| Y1-13A | 25133 | 3120 | yes | yes | yes | IS | perfect | perfect |
| Y1-17A | 25134 | 2400 | yes | yes | yes | perfect | perfect | perfect |
| Y1-18A | 25135 | 2142 | yes | yes | yes | IS | perfect | perfect |
| Y1-19A | 25136 | 2697 | yes | yes | yes | IS | perfect | perfect |
| Y1-20A | 25137 | 3336 | yes | yes | yes | IS | perfect | perfect |
| Y1-23A | 25138 | 2697 | yes | yes | yes | IS | perfect | perfect |
| Y1-25A | 25139 | 2448 | yes | yes | yes | perfect | perfect | perfect |
| Y1-28A | 25140 | 2022 | yes | yes | yes | perfect | perfect | perfect |
| Y1-33A | 25141 | 2217 | yes | yes | yes | perfect | perfect | perfect |
| Y1-38A | 25142 | 2170 | yes | yes | yes | perfect | perfect | perfect |
| Y1-39B | 25143 | 1635 | yes | yes | yes | perfect | perfect | perfect |
| Y1-40A | 25144 | 3462 | yes | yes | yes | IS | perfect | perfect |
| Y1-43A | 25145 | 1668 | yes | yes | yes | perfect | perfect | perfect |
| Y1-45A | 25146 | 2316 | yes | yes | yes | perfect | perfect | perfect |
| Y1-47A | 25147 | 2184 | yes | yes | yes | perfect | perfect | perfect |
| Y1-48A | 25148 | 3147 | yes | yes | yes | IS | perfect | perfect |
| Y1-58B | 25149 | 2268 | yes | yes | yes | perfect | perfect | perfect |
| Y1-58C | 25150 | 2511 | yes | yes | yes | perfect | perfect | perfect |
| Y1-66C | 25151 | 2568 | yes | yes | yes | perfect | perfect | perfect |
| Y1-67B | 25152 | 2310 | yes | yes | yes | perfect | perfect | perfect |

COMPOSITIONS AND METHODS FOR CREATING ALTERED AND IMPROVED CELLS AND ORGANISMS

This application is the National Phase Under 35 U.S.C. § 371 of PCT International Application No. PCT/US2013/076526 filed on Dec. 19, 2013, which claims priority under 35 U.S.C. § 119 on Patent Application No. 61/739,671 filed on Dec. 19, 2012, and on Patent Application No. 61/761,175 filed on Feb. 5, 2013, the entire contents of each of which are hereby incorporated by reference.

BACKGROUND OF THE INVENTION

Numerous agricultural and industrial production systems and processes depend on specific organisms, such as plants, algae, bacteria, fungi, yeasts, protozoa and cultured animal cells, for production of useful materials and compounds, such as food, fiber, structural materials, fuel, chemicals, pharmaceuticals, or feedstocks thereof. In the process of the current shift to biological production systems for a variety of chemicals and fuels, a wide assortment of organisms will be used for production, most of them microbes, with an increasing tendency towards photosynthetic organisms (Dismukes 2008). The ability to grow robustly, and the ability to efficiently produce the materials and compounds of interest, are desirable properties of these organisms.

Optimization of the growth of these organisms and augmentation of their yield of useful materials and compounds is an ongoing activity of many companies and individuals, with the goal of achieving a higher productivity or yield, or lower production cost of commercially important materials and compounds. Such improvements can occur through the modification of production systems, or through the modification of the organisms themselves.

Genetic or epigenetic changes in organisms can be particularly powerful ways of improving the organisms' performance and raising their productivities. All organisms in use by humans have been selected for specific genetic compositions that maximize their productivity and usefulness. In addition, various techniques can be employed to increase the range of characteristics or phenotypes displayed by these organisms, enabling the selecting of superior strains and varieties. Among these techniques are mutagenesis, genetic engineering, transgenesis, metabolic engineering, breeding, adaptive mutation and others. Application of such techniques has allowed rapid progress in the improvement of organisms.

Deregulating genetic checkpoints is a general strategy for modifying the growth properties and yield of useful organisms. Genetic checkpoints have generally evolved to allow an organism to alter its growth, metabolism or progression through the cell cycle, enabling it to survive periods of stress or nutrient limitation. In multicellular organisms, checkpoints are also in place to inhibit cell divisions once a tissue or organ is mature and fully formed. Relieving these checkpoints is often desirable for maximizing growth, yield and productivity of an organism being cultured or grown in cultivation, where conditions of stress may be controllable and avoidable.

Among the genetic engineering methods developed in the past are gain-of-function approaches, through which one or more homologous or heterologous polynucleotides are introduced into an organism's genome. Typically, such polynucleotides are constructed in a manner that the polynucleotide product will be overexpressed in the organism, thus imparting a novel or altered function to that organism. Mutagenesis can also result in gain-of-function changes in a cell or an organism, although such changes are rarer in response to mutagenesis than loss-of-function changes, in which the activity of a polynucleotide or polynucleotide product is impaired or destroyed by the genetic change.

Polynucleotides tend to have specific functions which are a product of the polynucleotide sequence and of the biochemical properties of the encoded RNA or protein. The sequence and biochemical properties of a protein or RNA govern its structure, biochemical activity, localization within a cell, and association with other cellular components, allowing appropriate activity of the protein or RNA, and proper regulation of that activity. Alteration of a polynucleotide sequence resulting in abnormal properties of the encoded protein or RNA, affecting its biochemical and structural properties, sub-cellular localization and/or association with other proteins or RNAs, can have profound consequences on the characteristics or phenotype of the organism. Polynucleotide fusions, involving joining of intact or partial open reading frames encoded by separate polynucleotides, is a known way of altering a polynucleotide sequence to change the properties of the encoded RNA or protein and to alter the phenotype of an organism.

There are two general mechanisms by which polynucleotide fusions can alter an organism's phenotype. These two mechanisms can be illustrated with the case of polynucleotide A (encoding protein A') fused to polynucleotide B (encoding protein B'), in which proteins A and B have different functions or activities and/or are localized to different parts of the cell. The first mechanism applies to sub-cellular localization of the two proteins. The fusion protein encoded by the polynucleotide fusion of the two polynucleotides may be localized to the part of the cell where protein A' normally resides, or to the part of the cell where protein B' normally resides, or to both. This alteration of cellular distribution of the activities encoded by proteins A' and B' may cause a phenotypic change in the organism. A schematic illustration of the altered localization of two proteins as a result of their fusion is illustrated in FIG. 1.

The second general mechanism by which fusion proteins alter the phenotypic property of a cell or organism relates to the direct association of two different, normally separate functions or activities in the same protein. In the case of proteins A' and B', their fusion may lead to an altered activity of protein A' or of protein B' or of the multiprotein complex in which these proteins normally reside, or of combinations thereof. The altered activity includes but is not limited to: qualitative alterations in activity; altered levels of activity; altered specificities of activity; altered regulation of the activity by the cell; altered association of the protein with other proteins or RNA molecules in the cell, leading to changes in the cell's biochemical or genetic pathways. A schematic illustration of phenotypic changes arising in a cell as a consequence of expressing a fusion protein is shown in FIG. 1.

Gene fusions, the function-generating principle that the technology is based on, is not a regularly occurring biological mechanism (Ashby 2006, Babushok 2007, Whitworth 2009, Zhang 2009, Eisenbeis 2010), but it has been observed sufficiently often to confirm the validity of the strategy. Apart from occurring in evolutionary time, for example in the evolution of new gene sequences by exon shuffling (Gilbert 1978), gene fusions are frequent events in oncogenesis where the fusion of two proto-oncogenes contributes to uncontrolled cell proliferation of cancer cells (Mitelman 2004, Mitelman 2007, Rabbitts 2009, Inaki 2012). Examples of alteration of activity of a polynucleotide fusion are the BCL-ABL oncogene involved in promoting uncontrolled cell growth in chronic myeloid leukemia (Sawyers 1992, Melo 1996), the mixed-lineage leukemia (MLL) polynucleotides coding for Histone-lysine N-methyltransferase that are involved in aggressive acute leukemia (Marshalek 2011), prokaryotic two-component signal transduction proteins (Ashby 2006, Whitworth 2009) and multifunctional bacterial antibiotic resistance polynucleotides (Zhang 2009). Despite these examples, however, polynucleotide fusions are relatively rare in biology compared to other genetic changes such as point mutations and tend to occur at a frequency that is more appropriately measured over evolutionary time as opposed to per cell generation (Babushok 2007, Eisenbeis 2010). As a result, a system for creating artificial polynucleotide fusions has the potential to create many phenotypes that are rarely or never found in nature. Fusion proteins capable of bypassing a variety of genetic checkpoints in various useful organisms will allow the isolation of faster-growing and higher-yielding strains and varieties.

To date, no attempt has been made to take advantage of the function-generating capability of fusion genes or polypeptides in a large-scale and systematic manner. There are no published examples of large-scale collections of randomized, in-frame polynucleotide fusions. Previous examples of fusion proteins have been generated in a limited and directed fashion with specific outcomes in mind. The present invention describes the creation and use of systematic, randomized, large-scale and in-frame gene fusions or polynucleotide fusions for the purpose of altering gene function, generating new gene functions, new protein functions and/or generating novel phenotypes of interest in biological organisms.

The present invention is distinct from gene and protein evolution methods such as gene shuffling (Stemmer 1994, Stemmer 1994a) that randomly recombine homologous sequences in order to create new variants of specific genes and proteins. The present invention uses collections of sequences that are substantially non-homologous as input sequences to create random, recombinant and novel coding sequences.

BRIEF SUMMARY OF THE INVENTION

The present invention relates to methods and compositions that bring about changes in phenotypes in an organism through the introduction of randomized in-frame fusion polynucleotides into the genome of the organism. The random association of multiple sequences results in randomized in-frame fusion polynucleotides that disrupt or alter existing genetic or biochemical mechanisms or pathways in the cell or organism, thus creating novel characteristics of the transformed cell or organism. This method is useful for increasing diversity within populations of organisms, and creating new and useful phenotypes or characteristics in such organisms.

The present invention uses randomized in-frame fusion polynucleotides to create previously unknown phenotypes in a target cell or organism. The present invention is directed to a composition comprising at least 2 discrete random polynucleotides randomly fused in-frame to form at least one randomized in-frame fusion polynucleotide. The randomized in-frame fusion polynucleotide can be operably linked to at least one regulatory sequence that controls expression of the randomized in-frame fusion polynucleotide where the regulatory sequence is a promoter, a terminator, or an untranslated sequence. In one embodiment, the randomized in-frame fusion polynucleotide is operably linked to a vector. The randomized in-frame fusion polynucleotide can be introduced into a host cell. In some cases the host cell can be regenerated into the organism from which the host cell was derived. The randomized fusion polypeptide causes a phenotype that is not present in a control cell or a control organism.

The invention is also directed to large scale methods of producing randomized in-frame fused polynucleotides by isolating polynucleotides from an organism, optionally randomly fragmenting those polynucleotides and then randomly joining the fragments in-frame. Another embodiment presents a method of altering the phenotype of a cell comprising introducing into a host cell the composition containing the randomized in-frame fusion polynucleotide. Yet another embodiment presents a method for altering the phenotype of an organism by introducing a randomized in-frame fusion polypeptide into a host cell and then regenerating the organism from that cell. Yet another embodiment presents a method for identifying a randomized in-frame fusion polypeptide responsible for an altered phenotype by comparing the life cycle of the cell or organism containing the randomized in-frame fusion polypeptide to a control cell or organism, selecting the cell or organism containing the randomized in-frame fusion polypeptide that displays a phenotype absent in the control organism, isolating the randomized in-frame fusion polynucleotide encoding the randomized in-frame fusion polypeptide from the selected organism, introducing the isolated randomized in-frame fusion polynucleotide into a host cell and, if appropriate regenerating the organism from that host cell, and then comparing the randomized in-frame fusion polynucleotide containing cell or regenerated organism to a control organism to confirm that the observed altered phenotype remains.

In some embodiments, a collection of coding sequences (open reading frames or ORFs) is generated, and random pairs of ORFs are cloned into an expression vector as randomized translational fusions. This is done in a manner that each ORF present in the starting collection can be positioned in a 5' orientation with respect to the ORF it is fused to, or in a 3' orientation. The resulting library of randomized in-frame fusion polynucleotides is introduced into a target organism, and transformed cells or organisms are selected for presence of the randomized in-frame fusion polynucleotide. In another embodiment, populations of transformed organisms are selected or screened for a novel phenotype. Transformed organisms with the desirable phenotype are of direct utility in a process that the target organism is typically used for.

BRIEF DESCRIPTION OF THE DRAWINGS

FIG. 3: Example of assembling two ORFs into an expression vector in a single step by homology-dependent cloning. A 5' ORF and a 3' ORF (A) are PCR amplified using sequence-specific primers (P1, P2, P3, P4). Each primer contains extra sequences at its 5' end that specifies homology to sequences in the other ORF or in the vector, corresponding to the order in which the fragments are to be assembled (see B). The PCR-amplified ORFs (B), containing the sequences homologous to each other and to the cloning vector (C) are combined with the cloning vector and assembled into a final construct (D) by allowing the regions of homology between the three fragments to direct each fragment into the correct position and orientation. For simplicity, the figure shows only a single 5' ORF and a single 3' ORF, but the same method will work with mixtures containing any number of ORFs.

FIG. 7: 1% agarose gels showing 24 of the ORF Large Pools produced for the 3' ORFs (A) and 5' ORFs (B). Each lane contains 1 µg of DNA from the Large Pools. Each Large Pool contains the products of 8 different $2^{nd}$ stage multiplex PCR reactions grouped by size, with a total of 208-216 different *S. cerevisiae* ORF amplicons present in each Large Pool. The sizes of the DNA markers at the left and right side of each gel are as follows (from bottom, in bp): 75, 200, 300, 400, 500, 700, 1000, 1500, 2000, 3000, 4000, 5000, 7000, 10000, 20000.

FIG. 9: Table listing fusion proteins isolated in *Saccharomyces cerevisiae* in a screen for heat tolerance. Each row in the table lists a separate fusion gene isolated in the screen described in Example 2. The fusion genes are identified by name, SEQ ID NO: and their component 5' and 3' ORFs are listed, including their length, SEQ ID NO: and a brief description of their cellular function, if known. All of the listed fusion genes have complete, full-length 5' and 3' ORFs, and are fused in-frame. All cloning junctions are perfect. The linker sequence separating the two ORFs is complete and perfect in all cases where this part of the fusion gene was completely sequenced; in several cases, the sequence was incomplete (SI) and did not allow determination whether the linker sequence was correct.

DETAILED DESCRIPTION OF THE INVENTION

The present invention provides a method for screening and sampling a large number of biochemical, genetic and interactive functions for a desired phenotype. The present invention discloses a novel method of producing altered or improved cells or organisms by creating randomized fusions of open reading frames (ORFs), or fragments thereof, to create large libraries of polynucleotide combinations, which can be used to generate novel phenotypes and characteristics in useful organisms. The present invention describes methods to generate collections of randomized in-frame fusion polynucleotides.

An ORF is defined as any sequence of nucleotides in a nucleic acid that encodes a protein or peptide as a string of codons. The ORFs in the starting collection need not start or end with any particular amino acid. The ORF or polynucleotide sequence encoding a protein or peptide may be continuous or may be interrupted by introns.

The term "in-frame" in this invention, and particularly in the phrase "in-frame fusion polynucleotide" refers to the reading frame of codons in an upstream or 5' polynucleotide, gene or ORF as being the same as the reading frame of codons in a polynucleotide, gene or ORF placed downstream or 3' of the upstream polynucleotide, gene, or ORF that is fused with the upstream or 5' polynucleotide, gene or ORF. Collections of such in-frame fusion polynucleotides can vary in the percentage of fusion polynucleotides that contain upstream and downstream polynucleotides that are in-frame with respect to one another. The percentage in the total collection is at least 10% and can number 10%, 11%, 12%, 13%, 14%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any number in between.

Figure 1:
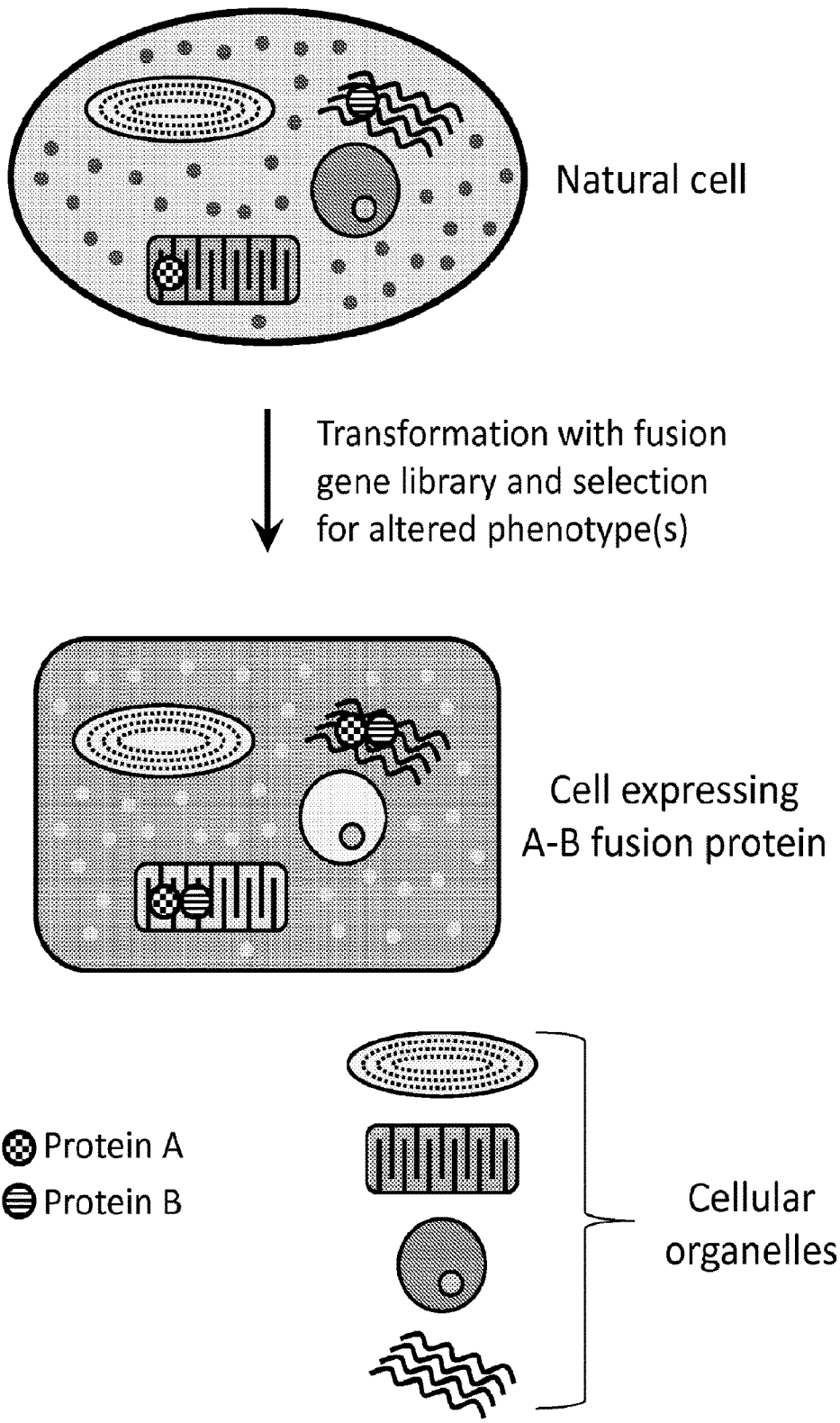
FIG. 1: Illustration of a change of phenotype of a cell expressing a randomized in-frame fusion polynucleotide. A natural cell (top of diagram) expresses two hypothetical proteins, protein A and protein B (shown as small round objects, see the legend at the bottom of the figure) which in this example are localized to different parts of the cell and have different functions. A population cells is transformed with a library of randomized in-frame fusion polynucleotides, and variants of the cell are selected that have altered phenotypes. In this particular example, the cell with altered properties expresses a polynucleotide encoding a randomized fusion between protein A and protein B (cell expressing A-B fusion protein at the bottom of the diagram). The randomized fusion protein is present at the subcellular location normally occupied by protein A as well as the one normally occupied by protein B. As a result, the cell expressing the randomized fusion protein has altered properties, depicted in this schematic diagram by changes in cell shape, shading and changes in the organelles.
Figure 2:
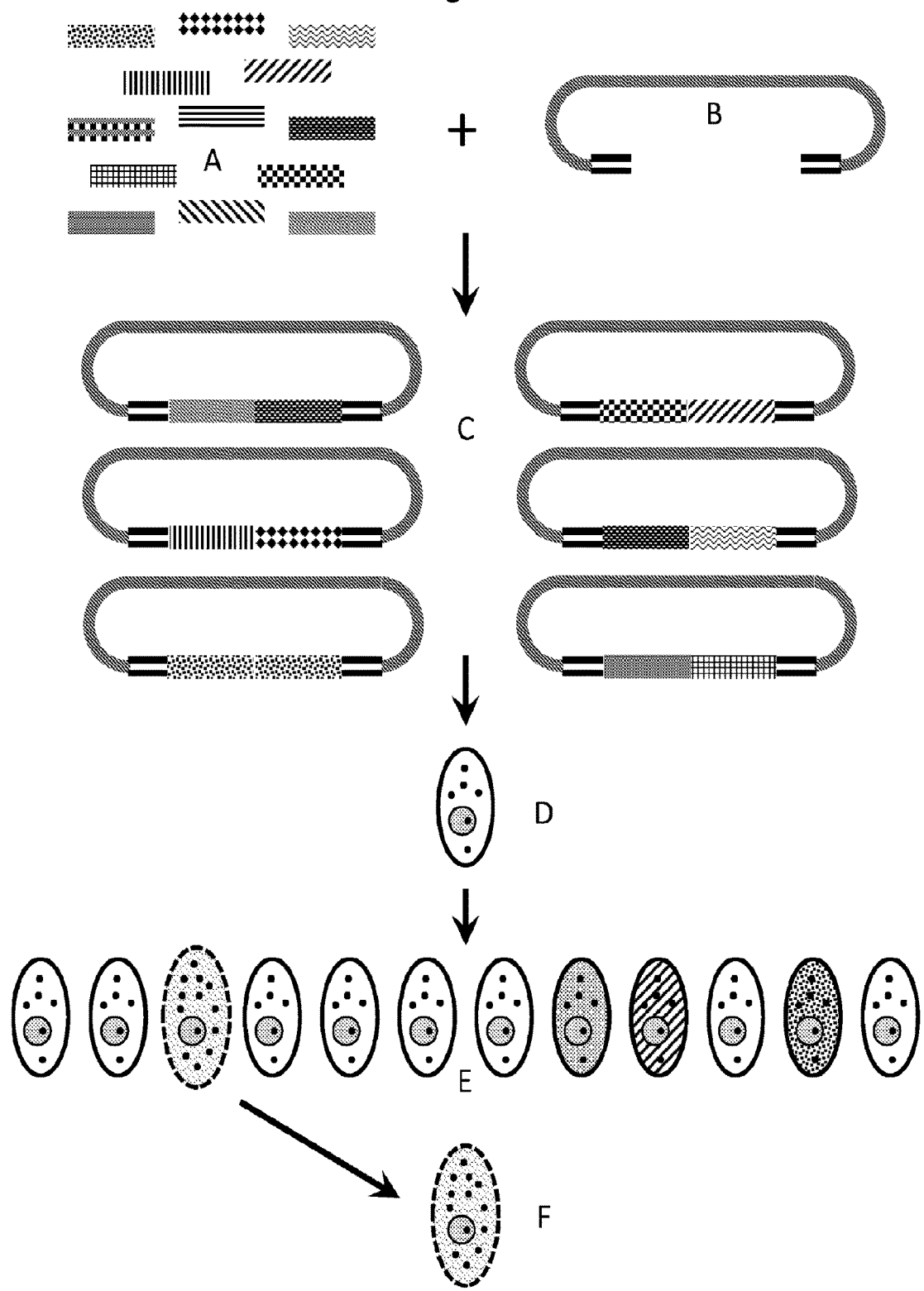
FIG. 2: Example of randomizing a collection of ORFs into randomized in-frame fusion polynucleotides and using these to alter an organism phenotypically. A collection of ORFs (A) is combined with a vector DNA molecule (B) in a manner that ORFs are combined in a randomized pairwise fashion, resulting in a large collection of randomized fused ORFs (C). The vector molecule in this example contains sequences mediating expression of the ORFs (double lines). The collection of randomized in-frame fusion polynucleotides is introduced into an organism (D), and transformants are isolated (E), some of which have altered phenotypes. Modified organisms with phenotypes of interest are isolated from this population (F). The randomized fusion polynucleotides expressed in transformants with altered phenotypes can be re-isolated and validated by re-transformation into the original cell population (not shown in this diagram).

A collection of ORFs is generated as separate DNA fragments, or separate sequences on larger DNA fragments. A library of randomized in-frame fusion polynucleotides is then generated from one or more collections or pools of polynucleotides encoding ORFs by combining two or more random polynucleotides, or fragments thereof, in a manner such that the combined polynucleotides can be expressed in the target cell as a randomized in-frame fusion peptide or polypeptide. The library of randomized in-frame fusion polynucleotides is generated in a fashion that allows many or all of the possible sequence combinations to be formed. The library is then introduced into an organism and allowed to express. The resulting collection of organisms expressing the randomized in-frame fusion polynucleotides is selected or screened for desirable phenotypes or characteristics. The polynucleotides responsible for the changes in the properties of a specific transformant can be recovered and used repeatedly. The general concept of this approach is illustrated in FIG. 2. As an example, all polynucleotides encoded by an organism can be used in the construction of the randomized in-frame fusion polynucleotide library. In the case of the laboratory bacterium E. coli, for example, every one of the 5,286 proteins encoded by E. coli can be the initial collection of ORFs used to make the randomized in-frame fusion polynucleotide library. The randomized in-frame fusion polynucleotide library thus contains a very high number of polynucleotide combinations ($5,286 \times 5,286 = 2.8 \times 10^7$ total combinations), and the presence of novel functions within this combinatorial set of polynucleotides is consequently high.

The polynucleotides used to make up the initial set of ORFs, or fragments thereof, can be from any source (genome, metagenome, cDNA, etc) and can be any subset of polynucleotides from such a source, selected by sequence composition, function or other criteria. The method can thus be tailored to capture specific biochemical functions, or functions from specific source organisms or source environments. The invention disclosed herein is therefore very flexible in the manner in which novel polynucleotide functions and phenotypes can be created.

The polynucleotides used to make up the initial set of ORFs will consist of sequences that are primarily non-homologous and distinct from one another, as opposed to ORFs that share extensive sequence homology. The term "non-homologous" in this invention is defined as having sequence identity at the nucleotide level of less than 50%.

Percentage of sequence identity: The term "percent sequence identity" refers to the degree of identity between any given query sequence, e.g. SEQ ID NO: 102, and a subject sequence. A subject sequence typically has a length that is from about 80 percent to 200 percent of the length of the query sequence, e.g., 80, 82, 85, 87, 89, 90, 93, 95, 97, 99, 100, 105, 110, 115, or 120, 130, 140, 150, 160, 170, 180, 190 or 200 percent of the length of the query sequence. A percent identity for any subject nucleic acid or polypeptide relative to a query nucleic acid or polypeptide can be determined as follows. A query sequence (e.g. a nucleic acid or amino acid sequence) is aligned to one or more subject nucleic acid or amino acid sequences using the computer program ClustalW (version 1.83, default parameters), which allows alignments of nucleic acid or protein sequences to be carried out across their entire length (global alignment, Chenna 2003).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher website and at the European Bioinformatics Institute website on the World Wide Web (ebi.ac.uk/clustalw).

To determine a percent identity of a subject or nucleic acid or amino acid sequence to a query sequence, the sequences are aligned using Clustal W, the number of identical matches in the alignment is divided by the query length, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The ORFs in the starting collection can number at least 5 or higher, including at least 5, 6, 7, 8, 9, 10, 15, 20, 30, 40, 50, 100, 200, 300, 400, 500, 1000, 2000, 3000, 4000, 5000, 10000, 20000, 30000, 40000, 50000, 100000, 200000, 300000, 400000, 500000, 1000000 or higher. The number of randomized fusion polynucleotides in the library typically equals at least the number of ORFs in the starting collection and can be as many as the square of the number of ORFs in the starting collection, which would be the expected number of all possible polynucleotide combinations, assuming that each ORF is present in both possible positions (5' and 3') and in combination with each other ORF. The number of randomized in-frame fusion polynucleotides in a library generated from fragments of ORFs would be expected to have an even greater number of combinations.

The ORFs in the starting collection can be derived from a single organism or from multiple organisms. The source of the ORFs includes but is not limited to: random pieces of genomic DNA or amplified genomic DNA from any virus, bacterium, archaeon, prokaryote, eukaryote, protozoan, yeast, fungus, animal, alga or plant or mixed population thereof; bacterial ORFs present as complete or partial collections or pools of protein-coding sequences derived from the genomes of one or more bacteria, archaea or other prokaryote; collections of cDNAs present as individual clones or pools of protein-coding sequences from bacteria, archaea, any prokaryote or any eukaryotic organism; randomized or partially randomized oligonucleotides; partially or fully random DNA sequences derived from randomized oligonucleotides by amplification.

The ORFs in the starting collection can comprise the entire collection of ORFs from an organism's genome, or a fraction thereof. The ORFs in a collection or pool can be pre-selected based on known function, sequence composition, sequence content, sequence homology, amino acid composition of the encoded proteins, amino acid content of the encoded proteins, sequence homology of the encoded proteins, length, presence of specific motifs, charge, hydrophobicity, isoelectric point, 3-dimensional structure or fold, ability to associate with other proteins, or any other property.

The ORFs in the starting collection can contain natural sequences or mutagenized sequences, including known variants of certain polynucleotides known to have a gain or loss of function, or an altered function. They can also contain degenerate sequences or sequences altered by mutagenesis. Degenerate sequences in this case are defined as populations of sequences where specific sequence positions differ between different molecules or clones in the population. The sequence differences may be in a single nucleotide or in multiple nucleotides of any number, examples being 2, 3, 4, 5, 6, 7, 8, 9, 10, 20, 30, 40, 50, 60, 70, 80, 90, 100, 200, 300, 400, 500, 600, 700, 800, 900 or 1000 nucleotides. Multiple, degenerate nucleotides may be adjacent or separated by constant or fixed sequences that are not degenerate. Sequence differences in a degenerate sequence may involve presence of 2, 3 or 4 different nucleotides in that position within the population of sequences, molecules or clones. Examples of degenerate nucleotides in a specific position of a sequence are: A or C; A or G; A or T; C or G; C or T; G or T; A, C or G; A, C or T; A, G or T; C, G or T; A, C, G or T.

The ORFs in the starting collection can be free of introns, such as the ORFs typically found in prokaryotes, or they may contain introns as are typically found in the ORFs of eukaryotes.

The ORFs in the starting collection can be derived from PCR fragments, PCR fragment pools, cDNAs, random pieces of genomic DNA, synthetic DNA, cloned DNA, DNA isolated directly from source organisms or from the environment, or from any other source, or any combination of sources.

The ORFs in a starting collection can be added in molar amounts corresponding to the concentrations of other ORFs, or in lower or higher amounts that change their representation within the final randomized in-frame fusion polynucleotide library. For example, if a polynucleotide coding for a specific protein conferring a desirable phenotype is suspected to have a particularly high chance of conferring that phenotype in a target organism, it is possible to over-represent this sequence in the ORF collection to ensure that most or all polynucleotide fusion combinations are tested in combination with the prioritized sequence.

The randomized in-frame fusion polypeptides can be designed in a manner that the ORFs are fused directly to each other, without any sequence inserted between the final codon of the upstream (5')ORF and the first codon of the downstream (3') ORF (or the other way around). Alternatively, the randomized in-frame fusion polypeptides are designed to have sequence insertions that encode additional amino acids between the two ORFs. These sequence insertions can range between 3 and 3000 nucleotides in length, and encode "linker" peptide or polypeptide sequences that are suitable for separating the two parts of the randomized fusion polynucleotide. Small amino acids, such as glycine, alanine, serine, proline, threonine, aspartic acid or asparagine are suitable for linker peptides because they tend to form flexible and unstructured domains, or alpha-helical domains lacking bulky side groups, that allow separation between the two parts of the encoded randomized fusion polypeptide and that allow each part of the encoded randomized fusion polypeptide to move independently relative to the other. Accordingly, sequence insertions separating the two fused ORFs may contain codons specifying these amino acids. Alternatively, the linker peptide sequence may be designed to contain a specific secondary structure, such as an alpha helix, beta sheet, coiled coil or turn, or combinations thereof, that permit the two domains of the encoded randomized fusion polypeptide to be separated by a specific structure or combinations of specific structures.

Each ORF can contain conserved 5' and 3' flanking sequences that match those at the 5' and 3' ends of other ORFs in the starting collection. These sequences are not part of the natural ORF and allow the ORFs to be amplified, cloned, isolated, and/or joined to other ORFs or to pieces of vector DNA. The conserved 5' and 3' flanking sequences can contain restriction sites, recombination sites, or any other sequence that permits specific joining to other ORFs, to vector sequences, or other sequences aiding in the transfer into an organism, replication within that organism, stability in that organism, or expression within that organism.

The ORFs in the starting collection can be full-length ORFs or partial ORFs and can range in size from 15 nucleotides to 100,000 nucleotides.

The ORFs in the starting collection can be configured to allow them to be placed at the 5' end of the resulting randomized in-frame fusion polynucleotide, or at the 3' end, or randomly at either end. The conserved sequences at the ends of the ORFs can be designed to allow such specific or non-specific placement. The library of randomized in-frame fusion polynucleotides may contain the same collection of ORFs at the 5' end as at the 3' end, or distinct collections of ORFs at each end.

The randomized polynucleotide fusion polynucleotides can be generated by a variety of methods for joining or cloning DNA molecules known to those skilled in the art including, but not limited to, traditional cloning using restriction enzymes and DNA ligase (ligation-dependent cloning), agarose gel-free cloning, ligation-independent (or ligation-free) cloning, site-specific recombination, homology-dependent cloning, recombinational cloning, homology-dependent end joining, annealing of single-stranded ends, linker tailing, topoisomerase-catalyzed cloning, enzyme-free cloning, and others. "Joining nucleic acid molecules" as used herein refers to any method that results in the molecules being operably linked at room temperature. Such methods include, but are not limited to, covalent linkage (ligation), annealing of complementary strands of nucleic acid molecules and other ways of associating two or more nucleic acid molecules.

In a specific embodiment of the invention, homologous sequences at the ends of the 5' and 3' polynucleotides to be joined can be used to direct or mediate the joining event. A large number of methods exist that can be used to accomplish such homology-dependent assembly (Lobban 1973), including linked tailing (Lathe 1984), In-Fusion cloning (Zhu 2007, Irwin 2012), Sequence and Ligation-Independent Cloning (SLIC, Li 2007, Li 2012), FastCloning (Li 2011), Circular Polymerase Extension Cloning (Quan 2009, Quan 2011), the Gibson assembly method (Gibson 2009, Gibson 2010), Quick and Clean Cloning (Thieme 2011), and others (Vroom 2008).

Randomized in-frame fusion polynucleotides of this sort can impart new functions to an organism and change the organism's phenotype(s) in many different manners. To achieve such a change of phenotype, the library of randomized in-frame fusion polynucleotides is transformed into a target organism. The target organisms can be the source organism of some or all of the polynucleotides, sequences, or ORFs used to make the randomized in-frame fusion polynucleotide library, or it can be a different organism. Target organisms include but are not limited to: *E. coli*, yeast, any species of bacteria, archaea, yeast, fungi, algae, cultured algal cells, insects, nematodes, vertebrates, animals, cultured animal cells, plants, or cultured plant cells. The target organism is generally an organism which is used for specific purposes, including, but not limited to, use in industry or agriculture, or in the production of chemicals, foods, fibers, structural materials, fuels, pharmaceuticals, agrochemicals, dyes, cosmetics or other useful substances.

Transformants of the target organism are generated which express members of the randomized in-frame fusion polynucleotide library. The transformants are be selected or screened for presence of the randomized in-frame fusion polynucleotides encoding the randomized fusion polypeptides, and allowed to express the polypeptides. The population of transformants is then selected or screened for any observable, selectable or measurable phenotype. Such phenotypes include, but are not limited to, changes or alterations in the following properties: growth rate; rate of cell division; generation time; size; color; texture; morphology; population density; productivity; yield; shape; growth habit; composition; metabolism; uptake or utilization of nutrients, minerals, salts, ions, toxins or water; photosynthetic efficiency; sensitivity to or resistance to abiotic stresses such as temperature, osmotic strength, salinity, pH, electromagnetic radiation, organic solvents, oxidation, oxidizing agents, detergents, drought, wind, desiccation, flood, nutrient limitation, starvation, oxygen limitation, light, pressure, compaction, shear or ionizing radiation; tolerance or resistance to biotic stresses such as diseases, pests phages, viruses, infective agents, parasites or pathogens; appearance; reflective properties; fluorescent properties; refractivity; light-transmitting properties; electrical resistance, impedance or conductance; growth in the presence of specific nutrients; binding or adhesive properties; permeability; association or symbiosis with other organisms; pathogenicity; physical properties such as density, strength, hardness, brittleness, flexibility, rigidity, turgor pressure, electrical impedance, electrical resistance, electrical conductivity, magnetism, permeability, viscosity, color, texture or grain; behavior; response to environmental stimuli; expression of a polynucleotide; activity of an enzyme; rates of genetic or epigenetic change or mutation; ability to take up and/or integrate homologous or heterologous nucleic acid sequences; phenotypic diversity of a population; ability to be stained by dyes or compounds eliciting a change in color; resistance to antibiotics or toxins; resistance to penetration; quality of or production of products such as food, feed, fuel, fiber, structural materials, pharmaceutical compounds, cosmetics, dyes, chemicals, proteins, lipids, nucleic acids, fertilizers, or combinations thereof, or precursors thereof, or feedstocks for the production thereof.

Organisms expressing one or more specific randomized in-frame fusion polynucleotides can be re-transformed with the same library of randomized in-frame fusion polynucleotides, a similar library, or a different library, and the process of selecting or screening for altered properties of the organism repeated. In this manner, an iterative approach of transformation, selection, re-transformation, re-selection, etc. can be used to continue altering properties or phenotypes of the organism.

A randomized in-frame fusion polynucleotide can also be re-isolated from an organism transformed with the randomized in-frame fusion polynucleotide. The re-isolation can be done using any of a number of methods including, but not limited to, PCR amplification ad plasmid rescue (Ward 1990) followed by plasmid transformation into a laboratory organisms such as *E. coli*. After re-isolation, it is possible to re-transform the randomized in-frame fusion polynucleotide into the same organism and/or a different organism to confirm that the randomized in-frame fusion polynucleotide reproducibly confers the same phenotype in repeated experiments.

An organism expressing a randomized in-frame fusion polynucleotide and having an altered phenotype as a result of the randomized in-frame fusion polynucleotide can be used as a starting point for further phenotypic changes by transforming this organism again with a library of randomized in-frame fusion polynucleotides. The library of fusion polynucleotides in the second round of improvement can be the same library that was used to generate the organism with an altered phenotype, or it can be a different library. Such iterative rounds of transformation of an organism with randomized in-frame fusion polynucleotide libraries and selection for phenotypes can result in multiple phenotypic changes, or phenotypic changes that are more profound than can be achieved with a single round of transformation and selection.

In another embodiment of this invention, a collection of organisms transformed with a library of randomized in-frame fusion polynucleotides is selected or screened for alterations in the expression of polynucleotide sequences, either homologous to the organism or heterologous, compared to control organisms transformed with empty vector sequences. In this manner, for example, it is possible to obtain a phenotype of promiscuous expression, by which many polynucleotide sequences are expressed that would ordinarily not be expressed. Such a phenotype is useful for isolating novel genetic or biochemical pathways, or transferring novel genetic or biochemical pathways into a heterologous organism. Alternatively, this approach enables a phenotype of promiscuous repression, by which many polynucleotide sequences that are normally expressed are reduced in expression or are silent. Alternatively, it is possible to activate or deactivate transposons naturally present in the genome.

In another embodiment of this invention, a collection of organisms transformed with a library of randomized in-frame fusion polynucleotides is selected or screened for altered rates of genomic or genetic changes. These genomic and genetic changes include but are not limited to: point mutations; sequence insertions, deletions, or inversions; repeat copy number variation; chromosomal translocations; chromosome crossovers; gene conversion; alterations in the distribution, prevalence, position or expression of transposons; uptake of foreign nucleic acid sequences; integration of foreign nucleic acid sequences; or combinations thereof resulting in complex sequence changes and genome rearrangements. Such evolver phenotypes conferred by specific randomized in-frame fusion polynucleotides may be useful for generating organisms with high rates of evolution and an increased genetic and phenotypic diversity of organisms, or for generating organisms suitable for the introduction of targeted genetic changes, or organisms predisposed to a specific type of genetic change.

In yet another embodiment of this invention, a collection of organisms transformed with a library of randomized in-frame fusion polynucleotides is selected or screened for higher yield of a material or compound produced by the organism.

In a further embodiment of the invention, a collection of organisms transformed with a library of randomized in-frame fusion polynucleotides is selected or screened for the absence of genetic checkpoints that limit the growth rate, productivity or other properties of the cell or organism. In particular, this allows isolation of organisms with constitutive production of a material or compound that is naturally produced only in certain physiological or growth states, or is produced at maximal levels only in certain physiological or growth states.

In another embodiment of the invention, a collection of organisms transformed with a library of randomized in-frame fusion polynucleotides is selected or screened for altered activity or specificity of enzymes or biochemical pathways expressed by the cell.

In a still further embodiment of the invention, the collection of randomized in-frame fusion polynucleotides is made by randomly fusing one or a small number of polynucleotides of interest with a larger collection of polynucleotides. In this manner it is possible to create a collection of variants or mutants of the polynucleotides of interest, which can be screened for specific properties. In particular, in this manner it is possible to screen for enzymes with higher activity, altered activity, altered temperature optimum, altered pH optimum, resistance to high temperatures or extreme pHs, resistance to acids or bases, resistance to desiccation, resistance to organic solvents, resistance to high salt concentrations, resistance to proteases, or other desirable properties of an enzyme.

EXAMPLES

Example 1: Isolation of Randomized in-Frame Fusion Polynucleotides Capable of Conferring Stress Tolerance to *Escherichia coli*

Bacterial Strains and Genomic DNA Preparation:

A complete collection of *E. coli* ORFs is generated based on the reference sequence of *E. coli* strain K-12 MG1655 (available on the internet via the genome section of the University of Wisconsin website). This strain is available from the American Type Culture Collection (ATCC), and is used as a source of high-purity genomic DNA from which ORFs of interest are amplified. A sequence annotation of this genome is used to identify the start and stop codons of each ORF. For example, one particular annotation prepared by the J. Craig Venter Institute (available from the cmr-jcvi website on the internet) lists a total of 5,286 protein-coding ORFs, including both verified and hypothetical protein-coding genes, ranging in size from 93 bp (encoding 31 amino acids) to 7152 bp (encoding 2384 amino acids).

Figure 4:
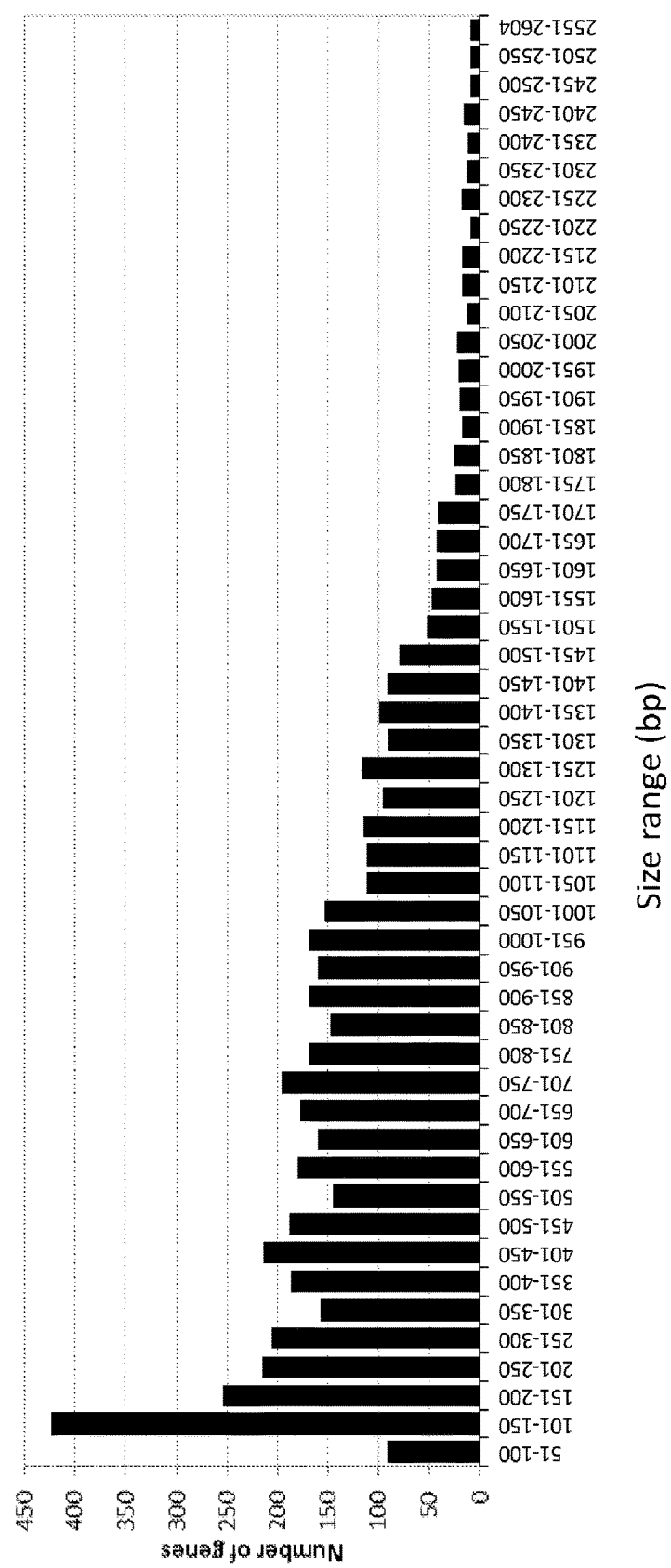
FIG. 4: Size distribution of selected *Escherichia coli* genes, 93-2604 bp in length, used as a starting collection of sequences for a randomized in-frame polynucleotide fusion library.

The length of genes used as input sequences is capped at 2604 bp, which increases the likelihood of successful PCR amplification and correct folding of the resultant in-frame fusion polypeptides or proteins. The result is a final collection of verified and uncharacterized ORFs for a total of 5095 ORFs for PCR amplification. The average length of this sequence collection is 791 bp and the median length is 711 bp. The size distribution of these *E. coli* ORFs is shown in FIG. 4.

When screening for polynucleotides conferring specific phenotypes in *E. coli*, it may be advantageous to include polynucleotides with known roles in the phenotypes of interest in the collection of ORFs to be screened. Examples include polynucleotides known to be involved in stress tolerance in organisms whose genomes have been sequenced. The current collection of sequenced microbial genomes includes a large number of thermophiles which may be a good source of chaperonins, heat-shock proteins or other stress-tolerance polynucleotides that confer stress-tolerance to other organisms and in combination with other ORFs.

The bacterial strain that serves as the source of ORFs is grown in liquid culture, cells are pelleted by centrifugation and then resuspended in 1/10 of the original culture volume using 20 mM Tris pH 8.0, 10 mM EDTA and 100 mM glucose. The cells are lysed by adding 1/100 volume 10 mg/ml hen egg lysozyme dissolved in 10 mM Tris pH 8.0, 10 mM EDTA and adding 1/20 volume 10 mg/ml DNA-se free RNAse A, mixing well and incubating at room temperature for 15 minutes. Cell lysis and release of genomic DNA is completed by treatment with proteinase K. To the lysed cells is added 1/10 volume of 1M Tris, 0.5M EDTA, pH 9.5 and 1/100 volume of a 20 mg/ml solution of proteinase K. The lysed cells are mixed gently by capping the tube and inverting it, and the mixture is incubated at 50° C. for 2 hours with occasional gentle mixing. The DNA is then extracted twice with an equal volume of phenol-chloroform (pH 7.0) followed by one additional extraction with an equal volume of chloroform. The DNA is precipitated by the addition of 1/10 volume 3M sodium acetate pH 5.5 and 2.5 volumes ethanol (or 1 volume isopropanol). The tube is immediately inverted after addition of the alcohol, and the DNA is visible as a stringy white precipitate. To avoid co-precipitating other impurities from the cell (residual protein or carbohydrates), the precipitated DNA is removed from the alcohol solution using a clean pipet tip or a pasteur pipet and is transferred to a clean tube containing 70% ethanol. The tube is capped and inverted multiple times to remove salts from the DNA precipitate. The pellet is collected by centrifugation, the ethanol removed by aspiration and the pellet is dried in an air flow hood to remove excess ethanol. The pellet is dissolved in 1×TE (10 mM Tris pH 8.0, 0.1 mM EDTA). Further purification of the DNA can be performed using column chromatography or cesium chloride density centrifugation (Sambrook 1989).

Expression Vectors

A simple and standard expression vector is used to express all fusion proteins. The *E. coli* lac promoter/operator is present on most standard cloning vectors and is capable of high-level expression of heterologous polynucleotides in the presence of lactose or lactose analogs. The pUC19 vector (Vieira 1982) is a convenient source of a plasmid backbone (pMB1 replicon), an antibiotic-resistance polynucleotide (e.g. β-lactamase from Tn3 conferring ampicillin resistance) and the *E. coli* lac promoter/operator and terminator sequences. These sequences are PCR amplified from pUC19 and used as a source of the plasmid backbone for cloning and expression of randomized in-frame fusion polynucleotides as illustrated in FIG. 3. For example, the PCR primers listed in SEQ ID NO: 25124 and SEQ ID NO: 25125 can be used to PCR amplify such a fragment from pUC19 to result in a 2391 bp linear vector fragment (SEQ ID NO: 25126). The regions of homology to this expression vector fragment that are included in the 5' end of the 5' ORF and in the 3' end of the 3' ORF (see FIG. 3) share homology with the ends of this vector sequence (SEQ ID NO: 25126).

As an alternative to the lac promoter system for expression of randomized in-frame fusion polynucleotides, other E. coli promoters can be used, such as the cycG promoter (Belyaeva 1992), the Tn3 β-lactamase promoter, the $P_{spc}$ ribosomal protein promoter or the phage lambda $P_L$ and $P_R$ promoters (Liang 1999, Menart 2002). The promoter of the stress-inducible E. coli psp operon (Brisette 1990, Brisette 1991, Weiner 1991, Weiner 1995, Jovanovic 1996, Model 1997, Beekwilder 1999) may be particularly suited for expression of randomized in-frame fusion polynucleotides under conditions of abiotic stress, when constitutive promoters dependent on vegetative cell growth may be not be very active. Alternatively, synthetic promoters can be developed from partially randomized sequences containing the consensus elements for bacterial expression (Jensen 1998a, Jensen 1998b, Hammer 2006, De May 2007).

To test a candidate promoter for suitability for the expression of randomized in-frame fusion polynucleotides, the selected promoters and their associated 5'UTRs are synthesized as 250 bp DNA fragments and cloned upstream of the lacZ α fragment in a high-copy plasmid such as pUC19. E. coli terminators are placed upstream of the promoter fragments to prevent read-through transcription from promoters present elsewhere on the plasmid. The resulting constructs are tested in E. coli for their ability to confer a blue colony color phenotype in the presence of the chromogenic substrate X-Gal, which is indicative of expression of the lacZ α fragment.

The plasmids described here for expression of randomized in-frame fusion polynucleotides are based on high-copy number plasmids such as those containing the pMB1 origin of replication. However, other plasmid systems are also suitable for this work. For example an F'-based plasmid such as pBeloBAC11 (Shizuya 1992) can be used to express randomized in-frame fusion polynucleotides using the same promoters as described above, or using a different set of promoters.

Fusion Gene Structure and ORF Amplification Strategy:

Two different sets of primers are designed for each ORF, one for cloning the ORF into the 5' position of the randomized in-frame fusion polynucleotide and the other for placing it 3'. The primers are designed to contain 15-100 bases of conserved sequence at their 5' ends. This conserved sequence is homologous to sequences at the ends of the other ORF they will be paired with, or to the ends of the vector sequences. This sequence homology is illustrated in FIG. 3. Because each ORF is to be placed at both the 5' and the 3' position in combination with all the other ORFs, two different PCR amplicons are generated for each ORF, one destined for the 5' position and the other for the 3' position (see FIG. 3).

For example, a hypothetical polynucleotide sequence A, coding for a peptide or protein, can be part of a starting collection of polynucleotides intended to be used for the construction of a collection of randomized in-frame fusion polynucleotides. The goal of generating the collection of randomized in-frame fusion polynucleotides is to have each polynucleotide in the starting collection, including polynucleotide A, present at the 5' position of a series of randomized in-frame fusion polynucleotides, and to have the same sequence present in the 3' position of a different series of randomized in-frame fusion polynucleotides. In each of these two series of randomized in-frame fusion polynucleotides, the polynucleotide A will be fused with as many other members of the starting collection as feasible with the available methods for generating such fusions. In order to enable these separate series of fusions, with polynucleotide A in a 5' or in a 3' position with respect to the other polynucleotides present in the starting collection, two different versions of the polynucleotide sequence A are generated. The version of polynucleotide sequence A intended for use in the 5' position will not contain a stop codon and will have 5' homology (or other sequence compatibility for cloning purposes) to the promoter region of the expression vector. The version of polynucleotide sequence A intended for use in the 3' position will contain a stop codon and will have 3' homology (or other sequence compatibility for cloning purposes) to the terminator region of the expression vector.

The sequence separating the two ORFs in a randomized in-frame fusion polynucleotide (labeled as 'linker sequence' in FIG. 3) encodes a short peptide that is rich in glycine and serine residues. Such a peptide is expected to be unstructured and will provide a flexible protein spacer separating the two members of a randomized fusion protein while being relatively resistant to proteolysis. Examples of suitable linker peptide sequences are GGGGSGGSGGSGGGGS (SEQ ID NO: 25117) or SGGSSAAGSGSG (SEQ ID NO: 25118) or SAGSSAAGSGSG (SEQ ID NO: 25119, Wang 2010). Alternatively, alpha-helical linker sequences can be used, for example the sequence $A(EAAAAK)_nA$, n=2-5 (SEQ ID NOS: 25120 to 25123, Arai 2001).

Each primer contains 16 bases of conserved sequence at the 5' end that serves two purposes. First, the extra sequence allows efficient PCR amplification of pools of ORFs using conserved PCR primer sequences that are able to amplify all the ORFs in a collection without biasing the representation of different ORFs with respect to one another (Dahl 2005, Myllykangas 2011, Natsoulis 2011). Second, they contain homology to the expression vector (a derivative of the cloning and expression vector pUC19 (Vieira 1982, SEQ ID NO: 25126) and to the conserved sequences at the ends of the randomized in-frame fusion polynucleotide partner, enabling rapid and efficient, homology-dependent assembly of the randomized in-frame fusion polynucleotides in the vector (see FIG. 3). The two amplicons for each ORF only differ in the presence of a stop codon (occurring only in the ORFs destined for the 3' position of the randomized in-frame fusion polynucleotide library) and in their conserved flanking sequences.

The conserved sequence added to all 5' PCR primer of ORFs destined for the 5' position in a fusion gene is GCTGGATCCTGCTAGC (SEQ ID NO: 25127). The conserved sequence added to all 3' PCR primer of ORFs destined for the 5' position in a fusion gene is CAGGAGCTGCACTTCC (SEQ ID NO: 25128). The conserved sequence added to all 5' PCR primer of ORFs destined for the 3' position in a fusion gene is TGGAAGTGGTTCAGGA (SEQ ID NO: 25129). The conserved sequence added to all 3' PCR primers of ORFs destined for the 3' position in a fusion gene is CTACTCGAGACTGCAG (SEQ ID NO: 25130).

The 5'-terminal 16 nucleotides in the 3' PCR primer of ORFs destined for the 5' position in a fusion gene, and the 5'-terminal 16 nucleotides in the 5' PCR primer of ORFs destined for the 3' position in a fusion gene, form part of a linker sequence that separates the two ORFs. This 60 bp linker sequence, (SEQ ID NO: 25103), encodes a 20 amino acid peptide (SEQ ID NO: 25104) rich in glycine, serine and alanine, which is loosely based on sequences used by others when connecting two ORFs in a fusion gene (Arai 2001, Eldridge 2009, Wang 2010). This linker sequence is fully encoded in the second or conserved stage of PCR amplification (see below), resulting in the addition of conserved coding sequences to the 3' ends of the ORFs destined for the 5' position of the randomized in-frame fusion polynucleotides and the 5' end of the ORFs destined for the 3' position in the randomized in-frame fusion polynucleotides.

Because two entire sets of *E. coli* ORFs need to be generated, one for the 5' position in the fusion genes and the other for the 3' position, all procedures described below are performed in duplicate for the two ORF positions.

Sequence Amplification:

Each ORF is PCR amplified with polynucleotide-specific primers containing 20-30 polynucleotide-specific bases at the 3' end and the conserved sequences at the 5' ends. The amplification is performed for each polynucleotide individually, or for pools of polynucleotides simultaneously.

For individual amplification, the two primers, each at a final concentration of 0.5-5 µM, are combined with 10-1000 ng of *E. coli* genomic DNA, PCR buffer and thermostable polymerase in a total reaction volume of 1-50 µl. A high-fidelity thermostable polymerase such as Phusion® polymerase can be used. For Phusion® polymerase, the PCR amplicons are generated by 2 minutes denaturation at 95° C. followed by 10-35 cycles of 20 seconds at 95° C., 20 seconds at 60° C. and 1 min/kb at 72° C. (minimally 30 seconds at 72° C.). The efficiency of formation of the PCR product is measured by agarose electrophoresis or by fluorescent spectroscopy using a fluorometer such as a Qubit® fluorometer (Life Technologies). Successful PCR reactions can be purified using silica resins suitable for DNA purification. Unsuccessful reactions are repeated by varying the $Mg^{+2}$ concentrations in the PCR reaction and/or other reaction conditions. Following successful amplification of each ORF, the concentration of each PCR product is normalized, and products corresponding to specific size ranges are pooled for cloning.

Individual amplification has the advantage that the amplification of each ORF is performed and monitored separately, allowing approximately equivalent representation of each ORF in the final pool of ORFs. It has the disadvantage that a large number of PCR reactions need to be performed and assayed in parallel, requiring robotics and optimization of a large number of amplifications.

For pooled amplification, ORFs are pooled by size, because the efficiency of PCR amplification is strongly size dependent, and because the PCR conditions (extension time at 72° C., see above) depend on the size of the amplicon. The ORFs are separated into any number of size pools. A smaller number of size pools has the advantage that the amplification can be done in a smaller number of samples, saving time and reagents. A large number of size pools has the advantage that the complexity of each pool is lower, implying higher concentrations of each primer pair and thus a higher likelihood of successful amplification of each polynucleotide. A convenient number of size pools corresponds to the number of wells in one or two 96-well plates. For example, 192 pools of 26-27 ORFs each (192 pools×26.54 ORFs on average=5095 ORFs total; this corresponds to 103 pools containing 27 primer pairs each, and 89 pools containing 26 primer pairs each).

PCR amplification is performed in three steps: 1) an initial amplification using gene-specific primers followed by 2) bulk-up of each ORF pool using conserved primers, followed by further pooling, size selection on gels and 3) a third amplification step resulting in the final length PCR products. The three amplification steps are referred to as $1^{st}$ stage, $2^{nd}$ stage and $3^{rd}$ stage amplifications, respectively.

All PCR amplifications are performed using Phusion™ Hot Start II thermostable high-fidelity polymerase (Thermo Scientific™). The enzyme is supplied with a 5×HF amplification buffer which is used for all reactions. Amplifications are performed in 20 µL or 50 µL reaction volumes, as noted below. All amplifications are performed on T100 thermal cyclers (Bio-Rad Laboratories) containing 96-well blocks. The deoxynucleotide triphosphates (dNTPs) used in all amplifications are a stock containing 10 mM of each dNTP, also obtained from Thermo Scientific®. Deionized water is used in all reactions and to make all solutions not supplied with the polymerase.

All PCR Amplifications Follow the Same General Procedure:

1. A PCR mix as described below is prepared for each stage of the PCR reaction, and is kept cold until inserted into the thermal cycler.

2. The samples are mixed thoroughly and then centrifuged at 4000 rpm for 1 minute to bring the reaction contents to the bottom of the tube or well in a plate.

3. The plates or tubes are inserted into a thermal cycler.

$1^{st}$ Stage Amplification:

First stage amplifications are conducted using pools of sequence-specific PCR primers as noted above. Each amplification is performed in 20 µL total volume, using 2 µL of 10 ng/µL *Escherichia coli* strain MG1655 genomic template DNA per reaction. To each reaction are added 2.5 µL primer pools from 100 µM stocks to provide a total final primer concentration of 12.5 µM. Each primer pool contains either 26 or 27 primer pairs; and final individual primer concentrations are approximately 0.23-0.24 µM.

The 1st stage PCR reaction mix is set up in 20 µl total volume and is mixed from the following components: 4 µl 5× Phusion® HF Buffer, 0.4 µl 10 mM dNTPs, 10.7 µl deionized $H_2O$, 2 µl 10 ng/µl genomic template DNA, 2.5 µL primer pools (100 µM), 0.4 µl Phusion™ Hot Start II thermostable polymerase (2 units/µl). The PCR cycling conditions are as follows: initial denaturation at 98° C. for 45 sec, 10 cycles consisting of three steps each (98° C. for 10 seconds, 60° C. for 30 seconds and 72° C. for 3 minutes), a final extension step at 72° C. for 3 minutes and a soak at 4° C. until removal of the samples from the thermal cycler. After the PCR amplification is complete, the samples are removed from the thermal cycler, mixed thoroughly, and centrifuged at 4000 rpm for 1 minute to provide the $1^{st}$ Stage amplification product.

$2^{nd}$ Stage Amplification:

The primers used in $2^{nd}$ stage amplifications are single primers with homology to the conserved portions of the $1^{st}$ stage amplification primers. The $2^{nd}$ stage primers are prepared as pairwise mixes, each containing equimolar amounts of the two primers and containing a total primer concentration of 20 µM.

The $2^{nd}$ stage PCR reaction mix is set up in 50 µl total volume and is mixed from the following components: 10 µl 5× Phusion® HF Buffer, 1 µl 10 mM dNTPs, 22 µl deionized $H_2O$, 10 µl $1^{st}$ stage reaction product, 6 µl $2^{nd}$ stage primer mix (20 µM) and 1 µl Phusion™ Hot Start II thermostable polymerase (2 units/µl). The PCR cycling conditions are as follows: initial denaturation at 98° C. for 45 sec, 25 cycles consisting of two steps each (98° C. for 20 seconds and 72° C. for 3 minutes), a final extension step at 72° C. for 3 minutes and a soak at 4° C. until removal from the thermal cycler.

After the PCR amplification is complete, the samples are removed from the thermal cycler, mixed thoroughly, and centrifuged at 4000 rpm for 1 minute.

To allow more efficient downstream processing of the samples, the 192 multiplex PCR samples are consolidated into 24 larger pools by pooling 8 samples into one. The amount of product in each multiplex PCR reaction is first quantitated to allow equimolar pooling of the different sized fragment collections. This is done either by conducting gel electrophoresis on each multiplex reaction and quantitating the fluorescence in each band of expected size, or by capillary electrophoresis, such as an Applied Biosystems® 3730 DNA analyzer or a QIAGEN® QIAxce® instrument. The concentration of desirable product in each multiplex reaction is used to calculate the relative amounts of each multiplex PCR reaction that are to be pooled together to result in equimolar amounts of each product added to the pool, taking the average size of each multiplex pool into consideration. Products are grouped and pooled by size to minimize amplification biases in downstream PCR amplifications.

The 192 multiplex reactions are combined into 24 larger pools as follows. Large Pool 1: multiplex pools 1-8; Large Pool 2: multiplex pools 9-16; Large Pool 3: multiplex pools 17-24; Large Pool 4: multiplex pools 25-32; Large Pool 5: multiplex pools 33-40; Large Pool 6: multiplex pools 41-48; Large Pool 7: multiplex pools 49-56; Large Pool 8: multiplex pools 57-64; Large Pool 9: multiplex pools 65-72; Large Pool 10: multiplex pools 73-80; Large Pool 11: multiplex pools 81-88; Large Pool 12: multiplex pools 89-96; Large Pool 13: multiplex pools 97-104; Large Pool 14: multiplex pools 105-112; Large Pool 15: multiplex pools 113-120; Large Pool 16: multiplex pools 121-128; Large Pool 17: multiplex pools 129-136; Large Pool 18: multiplex pools 137-144; Large Pool 19: multiplex pools 145-152; Large Pool 20: multiplex pools 153-160; Large Pool 21: multiplex pools 161-168; Large Pool 22: multiplex pools 169-176; Large Pool 23: multiplex pools 177-184; and Large Pool 24: multiplex pools 185-192. The resulting average ORF sizes (with and without added primer sequences) of each Large Pool is calculated based on the sizes of its component ORFs.

Once pooling has been completed, an amount of each ORF Large Pool corresponding to 10 µg of total desirable product are purified using a silica resin column or plate such as the Macherey Nagel NucleoSpin® 96 PCR cleanup kit, following the manufacturer's recommendations. After elution of the purified PCR product, each sample is mixed thoroughly and its concentration determined spectrophotometrically.

To eliminate unwanted size products and primer dimers from the 48 Large Pools, 2 µg of each pool is electrophoresed on a 1% agarose gel and stained with ethidium bromide, the bands visualized under UV or blue light, and gel fragments corresponding to the correct size of each larger pool are excised from the gel. The gel fragments are weighed and DNA is purified from them using silica resin gel purification methods such as the Macherey Nagel NucleoSpin® Gel and PCR clean-up kit, following the manufacturer's recommendations. When the purification is complete, the concentrations of all samples are determined spectrophotometrically, and the concentration of each purified $2^{nd}$ stage Large Pool amplification product is adjusted to 10 ng/µL for $3^{rd}$ Stage Amplification.

$3^{rd}$ Stage Amplification:

The $3^{rd}$ stage amplification adds the final sequences to each PCR product to allow efficient assembly by end homology and to increase the amount of each Large Pool. The primers used in $3^{rd}$ stage amplifications are single primers with homology to the conserved portions of the $1^{st}$ and $2^{nd}$ stage amplification primers. The $3^{rd}$ stage primers are prepared as pairwise mixes, each containing equimolar amounts of the two primers and containing a total primer concentration of 20 µM.

The $3^{rd}$ stage PCR reaction mix is set up in 50 µl total volume and is mixed from the following components: 10 µl 5× Phusion® HF Buffer, 1 µl 10 mM dNTPs, 22 µl deionized $H_2O$, 10 µl gel-purified, pooled $2^{nd}$ stage reaction product (10 ng/µl), 6 µl $3^{rd}$ stage primer mix (20 µM) and 1 µl Phusion® Hot Start II thermostable polymerase (2 units/µl). The PCR cycling conditions are as follows: initial denaturation at 98° C. for 45 sec, 25 cycles consisting of two steps each (98° C. for 20 seconds and 72° C. for 3 minutes), a final extension step at 72° C. for 3 minutes and a soak at 4° C. until removal from the thermal cycler.

After the $3^{rd}$ stage amplification is complete, the samples are mixed thoroughly, centrifuged, and purified using a silica resin purification, such as the Macherey Nagel NucleoSpin® 96 PCR clean-up kit, following the manufacturer's recommendations. After elution, each sample is mixed thoroughly and its concentration is determined spectrophotometrically.

For more efficient downstream processing, the 24 Large Pools are then consolidated into 5 "Superpools", by combining the 4 smallest Large Pools into one Superpool and combining successive sets of 5 Large Pools to form additional Superpools. The relative amounts of each Large Pool added to each Superpool is calculated, by considering the final concentrations of each large pool after $3^{rd}$ stage amplification and purification, and the final average size of each Large Pool (including sequences added by primers), with the goal of adding equimolar amounts of each Large Pool to each Superpool.

As in previous steps in this example, Superpools are prepared based on ORF size, with similarly sized ORF Larger Pools grouped into the same Superpool. To minimize cloning biases based on insert size, size fractions are cloned separately into the expression vectors, by combining each size pool of the 5' ORFs with each size pool of the 3' ORFs pairwise, in each case together with the cloning vector.

Randomized in Frame Fusion Polynucleotide Library Construction

After amplification and pooling into Superpools, the relative concentrations of the ORFs are normalized for molar concentrations of DNA molecules (as opposed to mass concentrations). Specific ORFs, including ORFs from cloned polynucleotides or ORFs from other organisms that are added to an ORF collection generated by individual or pooled PCR amplification as described above, can be added to the ORF collection in varying amounts. For example, specific ORFs are added in molar amounts corresponding to the concentrations of other ORFs, or in lower or higher amounts that change their representation within the final randomized in-frame fusion polynucleotide library. For example, if a polynucleotide encoding a specific protein that confers stress tolerance is suspected to have a particularly high chance of conferring stress tolerance in *E. coli*, it is possible to over-represent this sequence in the ORF collection to ensure that most or all randomized in-frame fusion polynucleotide combinations are tested along with this prioritized sequence.

One-step assembly of two ORFs into a pUC19 expression vector molecule is directed by conserved/homologous sequences that are located at the 5' and 3' ends of each fragment and that specify the structure of the circular, assembled product, shown in FIG. 3. Any one of a large number of methods can be used to accomplish this homology-dependent assembly, all of which are derived from cloning methods that are based on the annealing of homologous, single-stranded DNA ends, such as linker tailing methods (Lathe 1984) or methods dependent on complementary homopolymeric single-stranded tails at the ends of DNA molecules (Lobban 1973). In addition, modern homology-dependent cloning techniques are conceptually related to the ligation-independent cloning methods described in the early 1990s (Aslanidis 1990, Aslanidis 1994). Such homology-dependent cloning methods include but are not limited to: In-Fusion cloning (Zhu 2007, Irwin 2012), Sequence and Ligation-Independent Cloning (SLIC, Li 2007, Li 2012), FastCloning (Li 2011), Circular Polymerase Extension Cloning (Quan 2009, Quan 2011), the Gibson assembly method (Gibson 2009, Gibson 2010), Quick and Clean Cloning (Thieme 2011), and others (Vroom 2008).

Library assembly is performed in vitro with each combination of the five 5' and the five 3' ORF superpools, for a total of 25 assembly reactions. In each reaction, 150 fmol of the 5'ORF superpool DNA and 150 fmol of the 3'ORF superpool DNA (molar concentrations based on average size) are combined with 75 fmol of the PCR-amplified single fragment pUC19 vector DNA (SEQ ID 25126). The volume of the DNA mixture is adjusted to 10 µl, to which is added 10 µl of assembly mix (200 mM Tris pH 8.0, 20 mM $MgCl_2$, 0.4 mM each of dATP, dCTP, dGTP and dTTP, 20 mM dithiothreitol, 2 mM nicotinamide adenine dinucleotide, 0.02 units/µl T5 exonuclease, 0.05 units/µl Phusion® thermostable DNA polymerase, 0.4 units/µl Taq ligase). The reaction is mixed gently and incubated at 50° C. for 1-2 hours. The reaction is then kept on ice or frozen before use for *E. coli* transformations.

This in vitro assembly procedure can be performed as described, or with other enzymes with exonuclease activity that may be suitable for this procedure, such as T4 DNA polymerase, Exonuclease III, lambda exonuclease, T5 exonuclease or T7 exonuclease. Exonucleases with 5' to 3' directionality of their activity (i.e. T4 polymerase, lambda exonuclease, T5 exonuclease or T7 exonuclease) are preferred as they result in higher numbers of base pairs of annealed sequence between the two nicks at each cloning junction, thus stabilizing the desired product. The procedure can be performed without the addition of Taq DNA ligase, with satisfactory results. The reaction may also be supplemented with polyethylene glycol (molecular weight 4000-10000) at a final concentration of 5-10% to promote annealing of single-stranded DNA ends. However, given sufficiently high DNA concentrations as noted above, PEG is not necessary.

The assembly reactions are transformed into *E. coli* by electroporation by mixing 1 µl of the assembly reaction with 25 µl electrocompetent DH10B cells (Life Technologies Corporation) or EC100 cells (Epicentre Technologies) on ice. The cell/DNA mixture is then transferred into a 1 mm gap width electroporation cuvette and electroporated at 1.5 kV using a Bio-Rad Micropulser electroporator. The cells are suspended in 1 ml LB broth, cultured in a 10 ml culture tube for 1 hour at ° C. shaking at 250 rpm, and plated on LB agar containing 50-100 µg/µl carbenicillin. Transformation efficiencies can be improved by desalting the assembly reaction, either by DNA precipitation with ethanol, or by microdialysis, or by centrifugation through a Bio-Rad Micro Bio-Spin P6 gel column following the manufacturer's recommendation.

Library Transformation and Screening

Following assembly, the different libraries are pooled for transformation into *E. coli*, to reduce the total number of transformations and samples that need to be handled. The separate ligations/libraries resulting from the assembly of specific ORF pools contain approximately a number of sequence combinations corresponding to the number of 5' ORFs× the number of 3' ORFs×2. For example, if 1000 5' ORFs are combined with 1000 3' ORFs there are 2 million total combinations. Typically, the goal of a screening project is to screen 3× as many clones or transformants as the library complexity to achieve a >90% chance that each combination is represented among the transformants, assuming equal sequence representation among the DNA pools. With the example given above that means that 6 million transformants are needed for selection or screening.

The pooled libraries containing randomized in-frame fusion polynucleotides are transformed into laboratory strains of *E. coli*, selected for presence of the plasmids, and allowed to express the encoded randomized fusion peptides or polypeptides. Transformants are plated on solid media in the presence of IPTG or lactose to induce expression of randomized in-frame fusion polynucleotides from the lac promoter. The growth of colonies on plates is monitored, allowing for screening or selection of colonies with altered growth and resistance properties. Traits that that can be selected or screened for on solid media include, but not limited to: growth rate (rate of increase of either cell number or cell mass or both), growth yield (final cell density or final cell mass after the culture reaches stationary phase), stress tolerance (ability to grow or survive under conditions of high or low temperatures or high osmotic strength) and product tolerance (ability to grow or survive in the presence of organic solvents such as ethanol and butanol or toxic chemicals).

Alternatively, transformants are cultured in bulk in liquid culture under conditions selecting for various types of growth and resistance properties of the cells. Traits that that can be selected or screened for on solid media include, but not limited to: growth rate (rate of increase of either cell number or cell mass or both), stress tolerance (ability to grow or survive under conditions of high or low temperatures or high osmotic strength) and product tolerance (ability to grow or survive in the presence of organic solvents such as ethanol and butanol or toxic chemicals). Examples of selections and screens using solid and liquid media are given below.

For selections and screens on solid media, following transformation of the randomized fusion polypeptide library, transformants are pre-cultured in liquid media lacking antibiotics for 1 hour at 37° C. Antibiotics and IPTG are then added to the liquid culture to select for presence of the plasmid and induce expression of the randomized in-frame fusion polynucleotides, and the transformants are cultured for an additional hour. The culture is then diluted appropriately to allow for manageable numbers of transformants per plate (approximately 2000-20000 colonies per 10 cm plate depending on the trait selected or screened for). The culture is plated on solid medium whose composition depending on the trait being selected for, for example LB agar, or LB agar containing the additives listed in Table 1. The plates are incubated at for 12 hours to several days and colonies are selected at that time for colony picking, plasmid isolations, phenotype validation and characterization of active randomized in-frame fusion polynucleotides (see below). Colony selections are either made based on colony size (reflective of growth rate and growth yield, used to identify polynucleotides affecting growth rate, low temperature growth and growth yield traits) or on positive selection i.e. in the cases where the majority of transformants fail to grow on the plate and only those that grow contain a randomized in-frame fusion polynucleotide of interest (used to identify randomized fusion polynucleotides affecting tolerance of high temperatures, salt or organic solvents).

Because screens on solid media allow visualization of individual clones or transformants, they are particularly flexible for identifying transformants expressing randomized in-frame fusion polynucleotides contributing to rapid growth which are clearly visible as larger colonies. A difference as little as a few percent in doubling time can lead to a measurable difference in colony size prior to stationary phase. For example, a 12 hour growth period for a strain with an average doubling time of 30 minutes would allow 24 doublings, while a strain with a 5% faster average doubling time of 28.5 minutes would double 25.3 times, leading to a 2.5-fold difference in cell number which is clearly reflected in colony size. Such screens can be performed with any media conditions, for example it is possible to screen for growth rate in the presence of sub-lethal amounts of inhibiting agents such as salt, ethanol or butanol, or in sub-lethal high or low temperatures.

Selections and screens in liquid media are generally performed as bulk selections. Following transformation of the randomized in-frame fusion polynucleotide library into competent cells, transformants are pre-cultured in liquid media lacking antibiotics for 1 hour at 37° C. Antibiotics and IPTG are then added to the culture to select for presence of the plasmid and induce expression of the randomized in-frame fusion polynucleotides. The culture is then diluted 2-10× in fresh medium containing antibiotics and IPTG and containing selective agents such as those listed in Table 1 if appropriate. The culture is allowed to grow either at 37° C. or at a selective temperature for an additional 12 hours to several days, depending on the type of selection imposed on the cells. At that time, the cells are harvested by centrifugation, plasmid DNA containing the randomized in-frame fusion polynucleotide is extracted using standard mini-prep plasmid isolation procedures, the plasmid is then introduced into a fresh batch of competent cells, and the selection is repeated. Two to 10 cycles of batch selection can be performed in this manner before a transformation is plated on solid media allowing selection of individual transformants, followed by colony picking, plasmid isolations, phenotype validation and characterization of active fusion polynucleotides (see below).

Selections in liquid can be done either as survival selections or as selections for rapidly-dividing cells. Survival selections are performed in the presence of a lethal concentration of a selective agent (salt, ethanol or butanol, in this example) or at a lethal high or low temperatures, and for a specific period of time (generally 6-12 hours). Following the selective period, the selective culture is diluted in fresh, non-selective medium, or the temperature is returned to 37° C. to allow any surviving cells to resume normal growth. This culture containing surviving cells is grown up, plasmid extracted and the batch selection repeated if necessary, as described above.

Alternatively, a selection in liquid culture is performed to select for rapid growth in the presence of a sub-lethal concentration of a selective agent (salt, ethanol or butanol, in this example) or at a sub-lethal high or low temperatures. In this case, a liquid culture of transformants maintained under selective conditions is allowed to grow to mid-log phase only (generally 6-24 hours of growth, depending on the severity of selective conditions). At that point, the majority of cells in the culture are expected to be alive, but the culture is enriched for cells capable of normal, rapid growth under the selective conditions. The cells are pelleted by centrifugation, plasmid is extracted and the batch selection repeated if necessary.

TABLE 1

Examples of media and growth conditions for isolating polynucleotides affecting growth and resistance traits in E. coli

| Selection type | Solid or liquid medium | Incubation temperature | Media additives | Incubation time | Colony selection based on: |
|---|---|---|---|---|---|
| High temperature | solid | 45-55° C. | none | 2-3 days | Colonies growing on plates |
| Low temperature | solid | 5-10° C. | none | 5-10 days | Colony size |
| Salt | solid | 37° C. | 0.5-2.0M NaCl | 2-3 days | Colonies growing on plates |
| Ethanol | solid | 37° C. | 10-15% | 2-3 days | Colonies growing on plates |
| Butanol | solid | 37° C. | 1.5-2.0% | 2-3 days | Colonies growing on plates |
| Growth rate | solid | 37° C. | any | 12 hours | Colony size |
| Growth yield | solid | 37° C. | any | 24 hours | Colony size |
| High temperature | liquid | 45-55° C. | none | 12 h-2 days | Surviving cells |
| Low temperature | liquid | 5-10° C. | none | 3-5 days | Surviving cells |
| Salt | liquid | 37° C. | 1.5-3.0M NaCl | 6-24 hours | Surviving cells |
| Ethanol | liquid | 37° C. | 5-10% | 6-24 hours | Surviving cells |
| Butanol | liquid | 37° C. | 1.0-1.5% | 6-24 hours | Surviving cells |
| Growth rate | liquid | 37° C. | any | 4-8 hours | Surviving cells |

Plasmid Isolations and Phenotype Validation of Active Randomized in Frame Fusion Polynucleotides Following isolations of clones containing randomized in-frame fusion polynucleotides conferring desirable growth or tolerance phenotypes, individual colonies are placed into small cultures, grown, and plasmid isolated from them. This is possible to do in individual tubes containing small cultures (1-5 ml) or in 96-well plates containing 100-2000 µl of liquid medium. Plasmid DNA is extracted from each clone using standard plasmid isolation procedures. Plasmid DNA is characterized by restriction digestion gel electrophoresis, if necessary, to confirm the plasmid structure and presence of a randomized in-frame fusion polynucleotide insert. Candidate plasmids are then re-transformed into *E. coli* to validate their phenotype. Re-transformation can occur either into the same bacterial strain used for the selections or into a different strain. The re-transformations can be performed in 96-well or 384-well format to same time and reagents.

The re-transformations are then tested for growth or tolerance phenotypes. For growth rate and growth yield traits, this involves plating the transformants at low cell density and observing the sizes of the resulting colonies compared to a control transformant, or alternatively comparing doubling times or cell pellet size in liquid culture, with or without selective conditions, to the rate of growth of a control strain. For resistance phenotypes (temperature, ethanol and butanol), the re-screen involves replica plating of transformants (i.e. replicated from a 96-well plate onto a plate using a 96-pin tool) on to solid media and growth under selective conditions to compare the extent of growth of each transformation to controls. Alternatively, the transformations are exposed to selective conditions in liquid culture, followed by replicating by pin-tool on to non-selective solid media to assess the degree of cell survival in each culture, reflected in the number of surviving colonies.

A specific candidate randomized in-frame fusion polynucleotide can be tested either for conferral of the phenotype that it was originally selected for, or for another phenotype. Various phenotypes related to cell growth and stress tolerance can cross-react. For example, a randomized in-frame fusion polynucleotide selected for conferral of temperature tolerance can also confer salt tolerance, etc. By extensively cross-testing randomized in-frame fusion polynucleotides under various conditions it is possible to find randomized in-frame fusion polynucleotides with a broad ability to advance cell growth under various conditions of abiotic stress.

As noted above, the screens described in this example are based on use of high-copy number plasmids, such as those containing the pMB1 origin of replication. However, other plasmid systems are also suitable for this work; for maximum applicability of the polynucleotides discovered here it is useful to test them with other plasmid types. For example an F'-based plasmid such as pBeloBAC11 (Shizuya 1992) can be used to express randomized in-frame fusion polynucleotides using the same promoters as used on high-copy plasmids or a different set of promoters.

Characterization of Positive Clones and Additional Screens

Randomized in-frame fusion polynucleotide expression constructs conferring the most dramatic or broad phenotypes are sequenced to identify the active polynucleotides. The results are tabulated and the best fusion polynucleotides chosen for future work. Sequences identified repeatedly within distinct randomized in-frame fusion polynucleotides are used in future screens as part of the ORF collection. ORF collections containing randomized in-frame fusion polynucleotides already known to contain ORFs capable of conferring a desirable phenotype may be smaller than the whole-genome ORF collections described above for *E. coli*.

There are many advantages to limiting the size of an ORF collection, the most important of which is the smaller number of pairwise combinations that are represented in the resulting library of randomized in-frame fusion polynucleotides. Lower-complexity libraries can be screened faster and less expensively than more complex libraries, and are amenable to screening for more complex phenotypes than those listed above that involve visual screens and positive selections. Lower-complexity libraries are also amenable to testing in organisms with lower transformation efficiencies where it may not be realistic or reasonably possible to screen libraries containing tens of millions of sequence combinations (resulting from ORF collections numbering in the thousands), but which may be suitable for screening libraries containing hundreds of thousands of sequence combinations (resulting from ORF collections numbering in the hundreds).

Example 2: Isolation of Randomized in-Frame Fusion Polynucleotides Capable of Conferring Heat, Salt, UV and Butanol Tolerance to *Saccharomyces cerevisiae*

Product tolerance traits of production microbes are important factors that contribute to maximal yields and titers of fermentation products (Ding 2009, Jia 2009, Dunlop 2011). The ability of a microbe to resist and continue to grow in the presence of toxic compounds is genetically complex, dependent on a large suite of genes in multiple pathways (Liu 2009, Dunlop 2011). Previous efforts of engineering product tolerances in bacteria, cyanobacteria and yeasts have met with mixed success (Alper 2006, Tomas 2003, Atsumi 2010, Dunlop 2011a, Liu 2012, Tian 2013). Resistance traits are inherently difficult to create, and some of the resulting resistant strains suffer from lower yields (Baer 1987, Zhao 2003, Atsumi 2010). This compounds the complexity of the problem and underscores the need for a pipeline of solutions for product tolerance, that can be tested first individually and then in combination to determine their effects on cell growth and product titers. Butanol is featured as a target of this example because it is representative of medium-chain fuels and chemicals, many of which have high toxicity and whose production is being attempted and optimized in microbes (Dunlop 2011, Jang 2012, Lee 2012). Butanol is a chemical feedstock used for the production of many other chemicals (Mascal 2012).

Sequence Identification and PCR Primer Design:

A complete collection of *Saccharomyces cerevisiae* gene sequences are generated based on the reference sequence of yeast strain S288C, available on the yeastgenome web site. The sequence annotation of this genome, also available on the yeastgenome web page, is used for identifying the start and stop codons of each gene.

This particular annotation lists 6607 total protein coding genes, of which 5820 are 2,598 bp or shorter. The length of genes used as input sequences is capped at 2502 bp, preferably at 2598 bp, which increases the likelihood of successful PCR amplification and correct folding of the resultant in-frame fusion polypeptides or proteins. In preliminary analysis, all transposable element genes, pseudogenes, ORFs marked as 'dubious' in the annotation and ORFs less than 102 bp in length, preferably less than 90 bp in length, are eliminated. Duplicated ORFs are eliminated based on the presence of identical sequence in the first 24 bp starting at the ATG start codon and the final 24 bp ending at the stop codon. Internal homology is not considered in the elimination of duplicates, since the objective is to include as many yeast ORFs as possible while avoiding redundant synthesis of multiple, identical PCR primer pairs.

Figure 5:
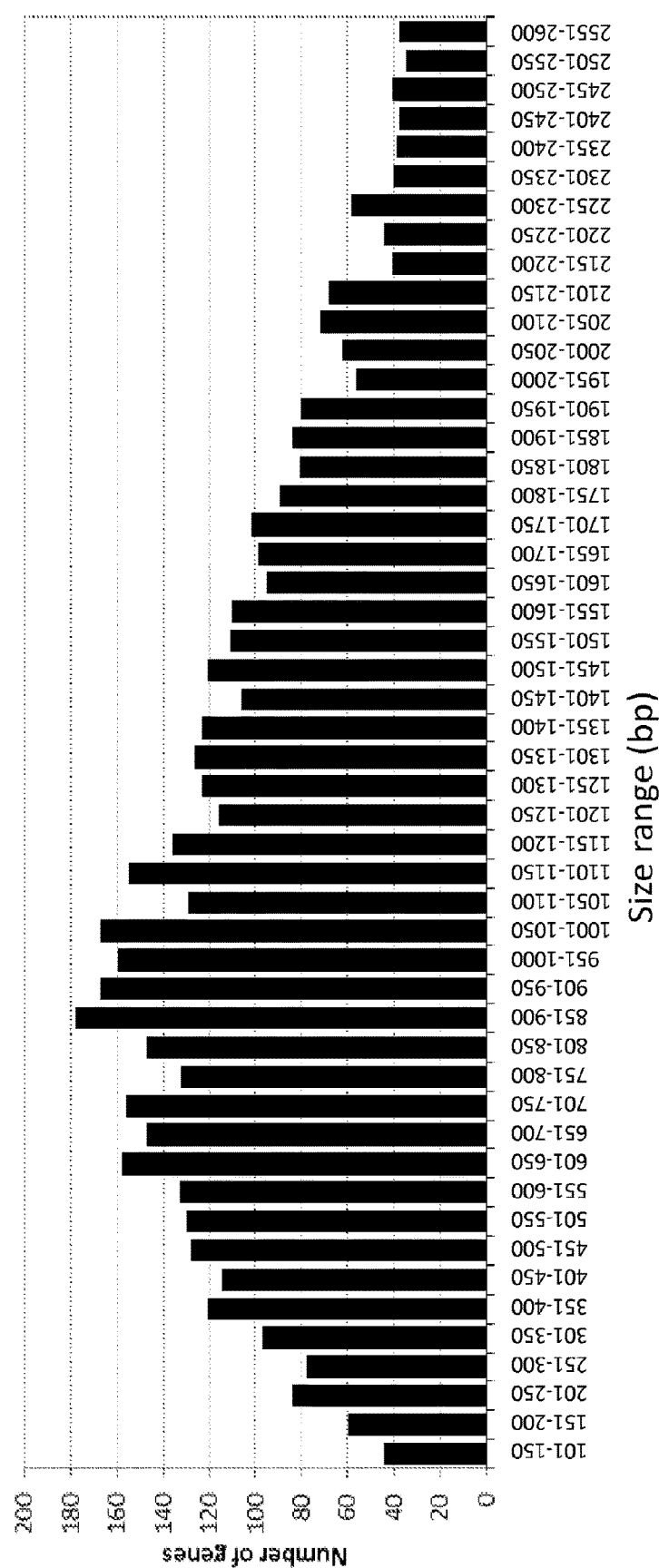
FIG. 5: Size distribution of selected *Saccharomyces cerevisiae* genes, 102-2598 bp in length, used as a starting collection of sequences for a randomized in-frame polynucleotide fusion library.

The result is a final collection of 5,095 ORFs for PCR amplification. The average length of this sequence collection is 1146 bp and the median length is 1074 bp. The size distribution of these ORFs is shown in FIG. 5. The ORFs are listed in SEQ ID NO: 1 to SEQ ID NO: 5019.

PCR primers are designed based on the known start and stop codons of each ORF, including 24 bp of coding sequence from each end. ATG start codons are added to the few yeast ORFs that, based on the annotation of yeast strain S288C, available on the yeastgenome web site, lack ATGs at the 5' ends of the coding region. Two different sets of primers are designed for each ORF, so that two different PCR products are generated, one for cloning the ORF into the 5' position of the fusion gene and the other for placing it 3'.

Each primer contains 16 bases of conserved sequence at the 5' end that serves two purposes. First, the extra sequence allows efficient PCR amplification of pools of ORFs using conserved PCR primer sequences that are able to amplify all the ORFs in a collection without biasing the representation of different ORFs with respect to one another (Dahl 2005, Myllykangas 2011, Natsoulis 2011). Second, they contain homology to the expression vector (a derivative of the yeast expression vector p426-GAL1 (Funk 2002, SEQ ID NO: 25096) and to the conserved sequences at the ends of the randomized in-frame fusion polynucleotide partner, enabling rapid and efficient, homology-dependent assembly of the randomized in-frame fusion polynucleotides in the vector (see FIG. 3). The two amplicons for each ORF only differ in the presence of a stop codon (occurring only in the ORFs destined for the 3' position of the randomized in-frame fusion polynucleotide library) and in their conserved flanking sequences.

The conserved sequence added to all 5' PCR primer of ORFs destined for the 5' position in a fusion gene is GGATCCAGCTAGCAAA (SEQ ID NO: 25099). The conserved sequence added to all 3' PCR primer of ORFs destined for the 5' position in a fusion gene is CAGGAGCTGCACTTCC (SEQ ID NO: 25100). The conserved sequence added to all 5' PCR primer of ORFs destined for the 3' position in a fusion gene is TGGAAGTGGTTCAGGA (SEQ ID NO: 25101). The conserved sequence added to all 3' PCR primers of ORFs destined for the 3' position in a fusion gene is AATTACATGACTCGAG (SEQ ID NO: 25102).

The 5' primers used for amplifying all the 5' ORFs are listed, in the same order as the ORFs, in SEQ ID NO: 5020 to SEQ ID NO: 10038. The 3' primers used for amplifying all the 5' ORFs are listed, in the same order as the ORFs, in SEQ ID NO: 10039 to SEQ ID NO: 15057. The 5' primers used for amplifying all the 3' ORFs are listed, in the same order as the ORFs, in SEQ ID NO: 15058 to SEQ ID NO: 20076. The 3' primers used for amplifying all the 3' ORFs are listed, in the same order as the ORFs, in SEQ ID NO: 20077 to SEQ ID NO: 25095. Thus, the ORF listed in SEQ ID NO: 1 can be PCR amplified with the primers of SEQ ID NO: 5020 and SEQ ID NO: 10039 when amplified for the 5' position; the same ORF can be PCR amplified with the primers of SEQ ID NO: 15058 and SEQ ID NO: 20077 when amplified for the 3' position. The ORF listed in SEQ ID NO: 2 can be PCR amplified with the primers of SEQ ID NO: 5021 and SEQ ID NO: 10040 when amplified for the 5' position; the same ORF can be PCR amplified with the primers of SEQ ID NO: 15059 and SEQ ID NO: 20078 when amplified for the 3' position. The ORF listed in SEQ ID NO: 3 can be PCR amplified with the primers of SEQ ID NO: 5022 and SEQ ID NO: 10041 when amplified for the 5' position; the same ORF can be PCR amplified with the primers of SEQ ID NO: 15060 and SEQ ID NO: 20079 when amplified for the 3' position. And so on.

The 5'-terminal 16 nucleotides in the 3' PCR primer of ORFs destined for the 5' position in a fusion gene, and the 5'-terminal 16 nucleotides in the 5' PCR primer of ORFs destined for the 3' position in a fusion gene, form part of a linker sequence that separates the two ORFs. This 60 bp linker sequence, (SEQ ID NO: 25103), encodes a 20 amino acid peptide (SEQ ID NO: 25104) rich in glycine, serine and alanine, which is loosely based on sequences used by others when connecting two ORFs in a fusion gene (Arai 2001, Eldridge 2009, Wang 2010). This linker sequence is fully encoded in the second or conserved stage of PCR amplification (see below), resulting in the addition of conserved coding sequences to the 3' ends of the ORFs destined for the 5' position of the randomized in-frame fusion polynucleotides and the 5' end of the ORFs destined for the 3' position in the randomized in-frame fusion polynucleotides.

Because two entire sets of yeast ORFs need to be generated, one for the 5' position in the fusion genes and the other for the 3' position, all procedures described below are performed in duplicate for the two ORF positions.

Genomic DNA for PCR Amplifications:

The chosen *Saccharomyces cerevisiae* genes are PCR amplified from strain S288C. This strain is available from the American Type Culture Collection (ATCCError! Hyperlink reference not valid. on the World Wide Web), and is used as a source of high-purity genomic DNA from which genes and polynucleotides of interest can be amplified.

To generate high-purity genomic DNA, commercially available yeast genomic DNA purification kits are used, such as the Zymo Research Corporation YeaStar™ Genomic DNA Kit, with additional cleanup steps to generate genomic DNA of sufficient purity. A 50 ml culture of *S. cerevisiae* strain S288C is generated by inoculating 50 ml YPD medium (per Liter of medium: 20 g Difco Bacto™ Peptone, 10 g Bacto™ yeast extract and 20 g glucose) with S288C cells from a plate or liquid culture and is grown for 2 days with shaking at 30° C. The cells are centrifuged at 3000 g for 5 minutes, and resuspended in 3.5 ml YD Digestion Buffer supplied with the kit; 150 µl Zymolyase solution supplied with the kit are then added and the cell suspension is mixed. The cell suspension is incubated at 37° C. for 1.5 hours without shaking. Then 3.5 ml YD Lysis Buffer (and here) is added and the solution mixed thoroughly.

An organic extraction is performed by adding 7.5 ml chloroform to the cell lysate, mixing vigorously for 2 minutes and centrifuging for 5 minutes at 4000 rpm. The supernatant is removed into a fresh 50 ml tube and distributed among 10 spin columns from the Zymo Research Corporation YeaStar™ Genomic DNA Kit inserted into a QIAGEN® QIAvac 24 Plus vacuum manifold. A vacuum is used to draw the lysate through the columns which are then washed twice with 300 µl DNA Wash Buffer. The spin columns are removed from the manifold, inserted into catch tubes and centrifuged at 14,000 rpm for 1 minute to remove residual ethanol. The genomic DNA is eluted in 100 µl TE buffer (10 mM Tris pH 8.0, 0.25 mM EDTA), and all eluates are pooled (~1.0 ml total). The DNA prep is further purified by extracting once with an equal volume of 25:24:1 phenol:chloroform:isoamyl alcohol and once with an equal volume of chloroform. The genomic DNA is precipitated by addition of 1/10 volume 3M sodium acetate pH 5.0 and 2.5 volumes ethanol. The tubes are centrifuged at 14000 rpm for 10 minutes, the pellets washed 1× with 800 µl of 70% ethanol and centrifuged again for 5 minutes; the supernatant is removed by aspiration and the pellets dissolved in 200 µl TE buffer. The DNA concentration is determined spectrophotometrically, and the DNA concentration adjusted to 10 ng/µl by addition of TE buffer.

Gene Amplification:

To save time and reagents, the ORFs are PCR amplified in 192 pools of 26-27 ORFs each (192 pools×26.14 ORFs on average=5019 ORFs total; this corresponds to 27 pools containing 27 primer pairs each, and 165 pools containing 26 primer pairs each). Because the efficiency of PCR amplification is strongly size dependent, and because the PCR extension time depends on the size of the amplicon, the ORFs are grouped into the pools by size. The average ORF size of each multiplex pool is as shown below in Table 2.

TABLE 2

Average ORF lengths of *Saccharomyces cerevisiae* multiplex ORF pools

| Multiplex pool # | Average ORF length (bp) |
|---|---|
| 1 | 117 |
| 2 | 149 |
| 3 | 171 |
| 4 | 191 |
| 5 | 207 |
| 6 | 222 |
| 7 | 239 |
| 8 | 260 |
| 9 | 279 |
| 10 | 296 |
| 11 | 310 |
| 12 | 324 |
| 13 | 337 |
| 14 | 351 |
| 15 | 364 |
| 16 | 373 |
| 17 | 384 |
| 18 | 396 |
| 19 | 410 |
| 20 | 424 |
| 21 | 436 |
| 22 | 446 |
| 23 | 455 |
| 24 | 465 |
| 25 | 474 |
| 26 | 485 |
| 27 | 496 |
| 28 | 507 |
| 29 | 519 |
| 30 | 528 |
| 31 | 538 |
| 32 | 547 |
| 33 | 556 |
| 34 | 568 |
| 35 | 581 |
| 36 | 591 |
| 37 | 598 |
| 38 | 606 |
| 39 | 613 |
| 40 | 621 |
| 41 | 630 |
| 42 | 638 |
| 43 | 646 |
| 44 | 653 |
| 45 | 661 |
| 46 | 669 |
| 47 | 677 |
| 48 | 688 |
| 49 | 698 |
| 50 | 706 |
| 51 | 714 |
| 52 | 721 |
| 53 | 730 |
| 54 | 739 |
| 55 | 749 |
| 56 | 756 |
| 57 | 765 |
| 58 | 773 |
| 59 | 784 |
| 60 | 796 |
| 61 | 806 |
| 62 | 815 |
| 63 | 824 |
| 64 | 832 |
| 65 | 842 |
| 66 | 850 |
| 67 | 858 |
| 68 | 866 |
| 69 | 874 |
| 70 | 881 |
| 71 | 887 |
| 72 | 895 |
| 73 | 903 |
| 74 | 911 |
| 75 | 919 |
| 76 | 928 |
| 77 | 933 |
| 78 | 939 |
| 79 | 947 |
| 80 | 954 |
| 81 | 962 |
| 82 | 969 |
| 83 | 979 |
| 84 | 986 |
| 85 | 996 |
| 86 | 1006 |
| 87 | 1015 |
| 88 | 1023 |
| 89 | 1030 |
| 90 | 1037 |
| 91 | 1044 |
| 92 | 1053 |
| 93 | 1063 |
| 94 | 1073 |
| 95 | 1084 |
| 96 | 1094 |
| 97 | 1101 |
| 98 | 1108 |
| 99 | 1118 |
| 100 | 1128 |
| 101 | 1135 |
| 102 | 1145 |
| 103 | 1153 |
| 104 | 1162 |
| 105 | 1177 |
| 106 | 1184 |
| 107 | 1192 |
| 108 | 1202 |
| 109 | 1213 |
| 110 | 1223 |
| 111 | 1234 |
| 112 | 1245 |
| 113 | 1256 |
| 114 | 1268 |
| 115 | 1279 |
| 116 | 1290 |
| 117 | 1299 |
| 118 | 1307 |
| 119 | 1316 |
| 120 | 1329 |
| 121 | 1340 |
| 122 | 1352 |
| 123 | 1362 |
| 124 | 1372 |

TABLE 2-continued

Average ORF lengths of *Saccharomyces cerevisiae* multiplex ORF pools

| Multiplex pool # | Average ORF length (bp) |
|---|---|
| 125 | 1382 |
| 126 | 1393 |
| 127 | 1403 |
| 128 | 1414 |
| 129 | 1427 |
| 130 | 1441 |
| 131 | 1453 |
| 132 | 1464 |
| 133 | 1473 |
| 134 | 1481 |
| 135 | 1494 |
| 136 | 1506 |
| 137 | 1517 |
| 138 | 1530 |
| 139 | 1542 |
| 140 | 1553 |
| 141 | 1566 |
| 142 | 1576 |
| 143 | 1586 |
| 144 | 1600 |
| 145 | 1618 |
| 146 | 1632 |
| 147 | 1645 |
| 148 | 1656 |
| 149 | 1667 |
| 150 | 1680 |
| 151 | 1693 |
| 152 | 1706 |
| 153 | 1718 |
| 154 | 1730 |
| 155 | 1744 |
| 156 | 1758 |
| 157 | 1769 |
| 158 | 1784 |
| 159 | 1807 |
| 160 | 1822 |
| 161 | 1835 |
| 162 | 1852 |
| 163 | 1867 |
| 164 | 1881 |
| 165 | 1898 |
| 166 | 1916 |
| 167 | 1931 |
| 168 | 1948 |
| 169 | 1972 |
| 170 | 1992 |
| 171 | 2012 |
| 172 | 2034 |
| 173 | 2056 |
| 174 | 2071 |
| 175 | 2090 |
| 176 | 2112 |
| 177 | 2129 |
| 178 | 2150 |
| 179 | 2180 |
| 180 | 2210 |
| 181 | 2243 |
| 182 | 2266 |
| 183 | 2286 |
| 184 | 2310 |
| 185 | 2347 |
| 186 | 2380 |
| 187 | 2415 |
| 188 | 2444 |
| 189 | 2478 |
| 190 | 2510 |
| 191 | 2546 |
| 192 | 2583 |

PCR amplification is performed in three steps: 1) an initial amplification using gene-specific primers followed by 2) bulk-up of each ORF pool using conserved primers, followed by further pooling, size selection on gels and 3) a third amplification step resulting in the final length PCR products. The three amplification steps are referred to as $1^{st}$ stage, $2^{nd}$ stage and $3^{rd}$ stage amplifications, respectively.

All PCR amplifications are performed using Phusion™ Hot Start II thermostable high-fidelity polymerase (Thermo Scientific™). The enzyme is supplied with a 5×HF amplification buffer which is used for all reactions. Amplifications are performed in 204 or 50 µl reaction volumes, as noted below. All amplifications are performed on T100 thermal cyclers (Bio-Rad Laboratories) containing 96-well blocks. The deoxynucleotide triphosphates (dNTPs) used in all amplifications are a stock containing 10 mM of each dNTP, also obtained from Thermo Scientific®. Deionized water is used in all reactions and to make all solutions not supplied with the polymerase.

All PCR Amplifications Follow the Same General Procedure:

1. A PCR mix as described below is prepared for each stage of the PCR reaction, and is kept cold until inserted into the thermal cycler.

2. The samples are mixed thoroughly and then centrifuged at 4000 rpm for 1 minute to bring the reaction contents to the bottom of the tube or well in a plate.

3. The plates or tubes are inserted into a thermal cycler.

$1^{st}$ Stage Amplification:

First stage amplifications are conducted using pools of sequence-specific PCR primers as noted above. Each amplification is performed in 20 µl total volume, using 2 µL of 10 ng/µL *Saccharomyces cerevisiae* strain S288C genomic template DNA per reaction. To each reaction are added 2.5 µL primer pools from 100 µM stocks to provide a total final primer concentration of 12.5 µM. Each primer pool contains either 26 or 27 primer pairs; and final individual primer concentrations are approximately 0.23-0.24 µM.

The 1st stage PCR reaction mix is set up in 20 µl total volume and is mixed from the following components: 4 µl 5× Phusion® HF Buffer, 0.4 µl 10 mM dNTPs, 10.7 µl deionized H$_2$O, 2 µl 10 ng/µl yeast genomic template DNA, 2.5 µL primer pools (100 µM), 0.4 µl Phusion™ Hot Start II thermostable polymerase (2 units/µl). The PCR cycling conditions are as follows: initial denaturation at 98° C. for 45 sec, 10 cycles consisting of three steps each (98° C. for 10 seconds, 60° C. for 30 seconds and 72° C. for 3 minutes), a final extension step at 72° C. for 3 minutes and a soak at 4° C. until removal of the samples from the thermal cycler. After the PCR amplification is complete, the samples are removed from the thermal cycler, mixed thoroughly, and centrifuged at 4000 rpm for 1 minute to provide the $1^{st}$ Stage amplification product.

$2^{nd}$ Stage Amplification:

The primers used in $2^{nd}$ stage amplifications are single primers with homology to the conserved portions of the $1^{st}$ stage amplification primers. The $2^{nd}$ stage primers used to amplify the ORFs destined for the 5' position in the fusion genes are PG0085 (SEQ ID NO: 25105) and PG0095 (SEQ ID NO: 25106). The $2^{nd}$ stage primers used to amplify the ORFs destined for the 3' position in the fusion genes are PG0096 (SEQ ID NO: 25107) and PG0088 (SEQ ID NO: 25108). The $2^{nd}$ stage primers are prepared as pairwise mixes, each containing equimolar amounts of the two primers and containing a total primer concentration of 20 µM. The 5' ORF primer mix contains primers PG0085 and PG0095; the 3' ORF primer mix contains primers PG0096 and PG0088 as listed above.

The 2$^{nd}$ stage PCR reaction mix is set up in 50 µl total volume and is mixed from the following components: 10 µl 5× Phusion® HF Buffer, 1 µl 10 mM dNTPs, 22 µl deionized H$_2$O, 10 µl 1$^{st}$ stage reaction product, 6 µl 2$^{nd}$ stage primer mix (20 µM) and 1 µl Phusion™ Hot Start II thermostable polymerase (2 units/µl). The PCR cycling conditions are as follows: initial denaturation at 98° C. for 45 sec, 25 cycles consisting of two steps each (98° C. for 20 seconds and 72° C. for 3 minutes), a final extension step at 72° C. for 3 minutes and a soak at 4° C. until removal from the thermal cycler.

After the PCR amplification is complete, the samples are removed from the thermal cycler, mixed thoroughly, and centrifuged at 4000 rpm for 1 minute.

To allow more efficient downstream processing of the samples, the 192 multiplex PCR samples are consolidated into 24 larger pools by pooling 8 samples into one. The amount of product in each multiplex PCR reaction is first quantitated to allow equimolar pooling of the different sized fragment collections. This is done either by conducting gel electrophoresis on each multiplex reaction and quantitating the fluorescence in each band of expected size, or by capillary electrophoresis, such as an Applied Biosystems® 3730 DNA analyzer or a QIAGEN® QIAxcel® instrument. The concentration of desirable product in each multiplex reaction is used to calculate the relative amounts of each multiplex PCR reaction that are to be pooled together to result in equimolar amounts of each product added to the pool, taking the average size of each multiplex pool into consideration. Products are grouped and pooled by size to minimize amplification biases in downstream PCR amplifications.

The 192 multiplex reactions are combined into 24 larger pools as follows. Large Pool 1: multiplex pools 1-8; Large Pool 2: multiplex pools 9-16; Large Pool 3: multiplex pools 17-24; Large Pool 4: multiplex pools 25-32; Large Pool 5: multiplex pools 33-40; Large Pool 6: multiplex pools 41-48; Large Pool 7: multiplex pools 49-56; Large Pool 8: multiplex pools 57-64; Large Pool 9: multiplex pools 65-72; Large Pool 10: multiplex pools 73-80; Large Pool 11: multiplex pools 81-88; Large Pool 12: multiplex pools 89-96; Large Pool 13: multiplex pools 97-104; Large Pool 14: multiplex pools 105-112; Large Pool 15: multiplex pools 113-120; Large Pool 16: multiplex pools 121-128; Large Pool 17: multiplex pools 129-136; Large Pool 18: multiplex pools 137-144; Large Pool 19: multiplex pools 145-152; Large Pool 20: multiplex pools 153-160; Large Pool 21: multiplex pools 161-168; Large Pool 22: multiplex pools 169-176; Large Pool 23: multiplex pools 177-184; and Large Pool 24: multiplex pools 185-192. The resulting average ORF sizes (without added primer sequences) of each Large Pool is listed in Table 3 below.

Once pooling has been completed, an amount of each ORF Large Pool corresponding to 10 µg of total desirable product are purified using a silica resin column or plate such as the Macherey Nagel NucleoSpin® 96 PCR cleanup kit, following the manufacturer's recommendations After elution of the purified PCR product, each sample is mixed thoroughly and its concentration determined spectrophotometrically. FIG. 7 shows an agarose gel with each of the 48 purified *Saccharomyces cerevisiae* 5' and 3' ORF Larger Pools.

To eliminate unwanted size products and primer dimers from the 48 Large Pools, 2 µg of each pool is electrophoresed on a 1% agarose gel and stained with ethidium bromide, the bands visualized under UV or blue light, and gel fragments corresponding to the correct size of each larger pool are excised from the gel. The gel fragments are weighed and DNA is purified from them using silica resin gel purification methods such as the Macherey Nagel NucleoSpin® Gel and PCR clean-up kit, following the manufacturer's recommendations. When the purification is complete, the concentrations of all samples are determined spectrophotometrically, and the concentration of each purified 2$^{nd}$ stage Large Pool amplification product is adjusted to 10 ng/µL for 3$^{rd}$ Stage Amplification.

3$^{rd}$ Stage Amplification:

The 3$^{rd}$ stage amplification adds the final sequences to each PCR product to allow efficient assembly by end homology and to increase the amount of each Large Pool. The primers used in 3$^{rd}$ stage amplifications are single primers with homology to the conserved portions of the 1$^{st}$ and 2$^{nd}$ stage amplification primers. The 3$^{rd}$ stage primers used to amplify the ORFs destined for the 5' position in the fusion genes are PG0055 (SEQ ID NO: 25109) and PG0003 (SEQ ID NO: 25110). The 3$^{rd}$ stage primers used to amplify the ORFs destined for the 3' position in the fusion genes are PG0004 (SEQ ID NO: 25111) and PG0006 (SEQ ID NO: 25112). The 3$^{rd}$ stage primers are prepared as pairwise mixes, each containing equimolar amounts of the two primers and containing a total primer concentration of 20 µM. The 5' ORF primer mix contains primers PG0055 and PG0003 while the 3' ORF primer mix contains primers PG0004 and PG0006 as listed above.

The 3$^{rd}$ stage PCR reaction mix is set up in 50 µl total volume and is mixed from the following components: 10 µl 5× Phusion® HF Buffer, 1 µl 10 mM dNTPs, 22 µl deionized H$_2$O, 10 µl gel-purified, pooled 2$^{nd}$ stage reaction product (10 ng/µl), 6 µl 3$^{rd}$ stage primer mix (20 µM) and 1 µl Phusion® Hot Start II thermostable polymerase (2 units/µl). The PCR cycling conditions are as follows: initial denaturation at 98° C. for 45 sec, 25 cycles consisting of two steps each (98° C. for 20 seconds and 72° C. for 3 minutes), a final extension step at 72° C. for 3 minutes and a soak at 4° C. until removal from the thermal cycler.

After the 3$^{rd}$ stage amplification is complete, the samples are mixed thoroughly, centrifuged, and purified using a silica resin purification, such as the Macherey Nagel NucleoSpin® 96 PCR clean-up kit, following the manufacturer's recommendations. After elution, each sample is mixed thoroughly and its concentration is determined spectrophotometrically.

For more efficient downstream processing, the 24 Large Pools are then consolidated into 5 "Superpools", by combining the 4 smallest Large Pools into one Superpool and combining successive sets of 5 Large Pools to form additional Superpools. The relative amounts of each Large Pool added to each Superpool is calculated, by considering the final concentrations of each large pool after 3$^{rd}$ stage amplification and purification, and the final average size of each Large Pool (including sequences added by primers), with the goal of adding equimolar amounts of each Large Pool to each Superpool. Table 3 lists the average size of ORFs in each of the Large Pools and Superpools. ORF sizes are given both as pure ORF sizes and as the final PCR fragment sizes which include the sequences added by the primers during PCR amplification.

TABLE 3

Average ORF sizes in *Saccharomyces cerevisiae* ORF Large Pools and Superpools

| Large Pool number | Average Large Pool ORF length (bp) | Average Large Pool ORF length + primers (bp) | Superpool number | Average Superpool ORF length (bp) | Average Superpool ORF length + primers (bp) |
|---|---|---|---|---|---|
| LP-1  | 195  | 312  | SP-1 | 365  | 482  |
| LP-2  | 329  | 446  |      |      |      |
| LP-3  | 427  | 544  |      |      |      |
| LP-4  | 511  | 628  |      |      |      |
| LP-5  | 592  | 709  | SP-2 | 729  | 846  |
| LP-6  | 658  | 775  |      |      |      |
| LP-7  | 727  | 844  |      |      |      |
| LP-8  | 800  | 917  |      |      |      |
| LP-9  | 869  | 986  |      |      |      |
| LP-10 | 929  | 1046 | SP-3 | 1064 | 1181 |
| LP-11 | 992  | 1109 |      |      |      |
| LP-12 | 1060 | 1177 |      |      |      |
| LP-13 | 1131 | 1248 |      |      |      |
| LP-14 | 1209 | 1326 |      |      |      |
| LP-15 | 1293 | 1410 | SP-4 | 1472 | 1589 |
| LP-16 | 1377 | 1494 |      |      |      |
| LP-17 | 1467 | 1584 |      |      |      |
| LP-18 | 1559 | 1676 |      |      |      |
| LP-19 | 1662 | 1779 |      |      |      |
| LP-20 | 1767 | 1884 | SP-5 | 2077 | 2194 |
| LP-21 | 1891 | 2008 |      |      |      |
| LP-22 | 2042 | 2159 |      |      |      |
| LP-23 | 2222 | 2339 |      |      |      |
| LP-24 | 2463 | 2580 |      |      |      |

Amplified pools of PCR products are analyzed by multiplexed short-read sequencing, for example using high-throughput Illumina® or Ion Torrent® sequencing systems, to determine relative abundances of the ORFs in each amplification reaction.

In this particular example, to determine relative abundances of individual ORFs resulting from $1^{st}$ stage and $2^{nd}$ stage multiplex PCR amplification, test amplifications of 3' ORFs were performed on 16 multiplex pools (pools #8, 17, 28, 41, 56, 70, 86, 101, 113, 125, 136, 146, 156, 164, 171, 178) comprising a total of 418 ORFs, and test amplifications of 5' ORFs were performed on 16 multiplex pools (pools #7, 16, 27, 40, 55, 69, 85, 100, 112, 124, 135, 145, 155, 163, 170, 177) comprising a total of 419 ORFs. The $2^{nd}$ stage amplification products of each group of 16 multiplex pools were prepared as described above, and were combined and sequenced using an Ion Torrent™ Ion 318™ Chip. The results were analyzed by aligning the sequences obtained from each combination of 16 multiplex pools to the target ORF sequences in these pools, using CLC Genomic Workbench sequence analysis software (CLC Bio®). In the 3' ORF multiplex pools, 395/418 (94%) of the ORFs were detected by at least a single sequence reaction, and 374/418 ORFs (89%) were represented at reasonable levels, after excluding outliers that were covered by very small numbers of reads. In the 5' ORF multiplex pools, 405/419 (97%) of the ORFs were detected by at least a single sequence reaction, and 386/419 ORFs (92%) were represented at reasonable levels, after excluding outliers that were covered by very small numbers of reads. As expected from a multiplex PCR strategy, the representation of individual ORFs in each pool fluctuated: the average standard deviation among 3' ORF multiplex pools was 75% of the average read number, and this number dropped to 62% when excluding outliers. The average standard deviation among 5' ORF multiplex pools was 69% of the average read number, and among the 5' ORFs this percentage dropped to 60% of the average read number when excluding outliers. These results indicate successful multiplex amplification of a high percentage of the ORFs within each sample, ensuring representation of a correspondingly high percentage of the ORFs in the fusion gene libraries made from these ORF collections.

Randomized in Frame Fusion Polynucleotide Library Construction

The yeast centromeric expression plasmid p416-GAL1 (Funk 2002) is used for all randomized in-frame fusion polynucleotide cloning and expression work. This plasmid expression vector uses the GAL1 galactose inducible promoter to direct expression of all randomized in-frame fusion polynucleotides. The entire expression vector (5538 bp) is amplified by PCR using the PCR primers PG0089 (SEQ ID NO: 25113) and PG0090 (SEQ ID NO: 25114). The amplified, linear vector is used for cloning complex libraries of randomized in-frame fusion polynucleotides as described below. Alternatively, the vector is amplified as two separate fragments; a 4295 bp first fragment amplified with primers PG0089 (SEQ ID NO: 25113)+PG0097 (SEQ ID NO: 25115) and a 1626 bp second fragment amplified with primers PG0090 (SEQ ID NO: 25114)+PG0098 (SEQ ID NO: 25116). These two fragments share 383 bp of end homology within the URA3 gene present in the vector sequence. Use of two vector fragments as opposed to a single vector fragment can have the advantage of lowering the background of colonies obtained with vector alone, and can give higher rates of fusion gene assembly.

Because the efficiency of the randomized in-frame fusion polynucleotide library construction step is also expected to be dependent on insert size, the sequences continue to be segregated based on length, see Table 3. For assembly of randomized libraries of in-frame fusion genes, the ORFs in each 5' Superpool are combined with the ORFs in each 3' Superpool for a total of 25 Superpool combinations. The average insert size ranges expected for the 25 libraries formed in the randomized in-frame fusion polynucleotide library assembly step are the sums of the average amplicon sizes for each of the Superpools shown in Table 3.

One-step assembly of two ORFs into an expression vector molecule is directed by conserved/homologous sequences that are located at the 5' and 3' ends of each fragment and that specify the structure of the circular, assembled product, shown in FIG. 3. A large number of methods exist that can be used to accomplish such homology-dependent assembly (Lobban 1973), including In-Fusion cloning (Zhu 2007, Irwin 2012), Sequence and Ligation-Independent Cloning (SLIC, Li 2007, Li 2012), FastCloning (Li 2011), Circular Polymerase Extension Cloning (Quan 2009, Quan 2011), the Gibson assembly method (Gibson 2009, Gibson 2010), Quick and Clean Cloning (Thieme 2011), direct assembly in yeast (Ma 1987, Degryse 1995, Raymond 1999, Raymond 2002, Shao 2009, Wingler 2011, Eckert 2012, Kuijpers 2013) and others (Vroom 2008).

In this particular example, two different assembly methods are used: direct assembly in yeast (Kuijpers 2013) and a modification of homology-dependent in vitro assembly methods (Gibson 2010, Li 2012).

Library Assembly and Cloning in *E. coli*

Library assembly is performed in vitro with each combination of the five 5' and the five 3' ORF superpools, for a total of 25 assembly reactions. In each reaction, 150 fmol of the 5'ORF superpool DNA and 150 fmol of the 3'ORF superpool DNA (molar concentrations based on average size, see Table 3) are combined with 75 fmol of the PCR-amplified single fragment vector DNA (5538 bp). The volume of the DNA mixture is adjusted to 10 µl, to which is added 10 µl of assembly mix (200 mM Tris pH 8.0, 20 mM $MgCl_2$, 0.4 mM each of dATP, dCTP, dGTP and dTTP, 20 mM dithiothreitol, 2 mM nicotinamide adenine dinucleotide, 0.02 units/µl T5 exonuclease, 0.05 units/µl PHUSION thermostable DNA polymerase, 0.4 units/µl Taq ligase). The reaction is mixed gently and incubated at 50° C. for 1-2 hours. The reaction is then kept on ice or frozen before use for *E. coli* transformations.

The assembly reactions are transformed into *E. coli* by electroporation by mixing 1 µl of the assembly reaction with 25 µl electrocompetent DH10B cells (Life Technologies Corporation) or EC100 cells (Epicentre Technologies) on ice. The cell/DNA mixture is then transferred into a 1 mm gap width electroporation cuvette and electroporated at 1.5 kV using a Bio-Rad Micropulser electroporator. The cells are suspended in 1 ml LB broth, cultured in a 10 ml culture tube for 1 hour at ° C. shaking at 250 rpm, and plated on LB agar containing 50-100 µg/µl carbenicillin. Transformation efficiencies can be improved by desalting the assembly reaction, either by DNA precipitation with ethanol, or by microdialysis, or by centrifugation through a Bio-Rad Micro Bio-Spin P6 gel column following the manufacturer's recommendation.

The quality of this assembly method was assessed by picking and sequencing twenty random clones from an assembly of 5' Superpool SP-3 with 3' Superpool SP-3 and the p416-GAL1 vector (SEQ ID NO: 25096). Out of the 20 clones, 12 showed full-length 5' and 3' ORFs fused in-frame, with all cloning junctions perfect and separated by a perfect linker sequence, with no ORFs found more than once. The remaining 8 clones contained either intact 5' or 3' ORFs, but showed rearrangements, frameshifts or unknown sequences within the second ORF. These results indicate that in vitro assembly followed by cloning in *E. coli* can produce libraries which are substantially composed of fusion genes consisting of random ORFs fused in-frame.

The transformation efficiency of each assembly reaction is tested in pilot electroporations by plating out small volumes of the transformation mixture and counting colonies the next day. The electroporations are then scaled up to allow generation of 1 million or more library clones per ORF pool combination. A total of 5 electroporations were performed for each ORF superpool combination when cloning of the *S. cerevisiae* Function Generator library in *E. coli*, yielding the clone numbers listed in Table 4, for a total library complexity of over 65 million clones.

TABLE 4

*E. coli* cloning of in vitro assembled Function Generator library

| ORF combination | 5' ORF superpool | 3' ORF superpool | Culture volume (ml) | Colony numbers (200 µl) | Total # of transformants |
|---|---|---|---|---|---|
| 1 | 5' SP-1 | 3' SP-1 | 500 | 95 | 237,500 |
| 2 | 5' SP-2 | 3' SP-1 | 500 | 1488 | 3,720,000 |
| 3 | 5' SP-3 | 3' SP-1 | 500 | 1360 | 3,400,000 |
| 4 | 5' SP-4 | 3' SP-1 | 500 | 1056 | 2,640,000 |
| 5 | 5' SP-5 | 3' SP-1 | 500 | 1060 | 2,650,000 |
| 6 | 5' SP-1 | 3' SP-2 | 500 | 988 | 2,470,000 |
| 7 | 5' SP-2 | 3' SP-2 | 500 | 948 | 2,370,000 |
| 8 | 5' SP-3 | 3' SP-2 | 500 | 1012 | 2,530,000 |
| 9 | 5' SP-4 | 3' SP-2 | 500 | 948 | 2,370,000 |
| 10 | 5' SP-5 | 3' SP-2 | 500 | 1348 | 3,370,000 |
| 11 | 5' SP-1 | 3' SP-3 | 500 | 1000 | 2,500,000 |
| 12 | 5' SP-2 | 3' SP-3 | 500 | 1000 | 2,500,000 |
| 13 | 5' SP-3 | 3' SP-3 | 500 | 1000 | 2,500,000 |
| 14 | 5' SP-4 | 3' SP-3 | 500 | 1000 | 2,500,000 |
| 15 | 5' SP-5 | 3' SP-3 | 500 | 1000 | 2,500,000 |
| 16 | 5' SP-1 | 3' SP-4 | 500 | 1000 | 2,500,000 |
| 17 | 5' SP-2 | 3' SP-4 | 500 | 1440 | 3,600,000 |
| 18 | 5' SP-3 | 3' SP-4 | 500 | 1000 | 2,500,000 |
| 19 | 5' SP-4 | 3' SP-4 | 500 | 560 | 1,400,000 |
| 20 | 5' SP-5 | 3' SP-4 | 500 | 1440 | 3,600,000 |
| 21 | 5' SP-1 | 3' SP-5 | 500 | 1000 | 2,500,000 |
| 22 | 5' SP-2 | 3' SP-5 | 500 | 1000 | 2,500,000 |
| 23 | 5' SP-3 | 3' SP-5 | 500 | 1000 | 2,500,000 |
| 24 | 5' SP-4 | 3' SP-5 | 500 | 1440 | 3,600,000 |
| 25 | 5' SP-5 | 3' SP-5 | 500 | 1440 | 3,600,000 |
| Total | | | | | 66,557,500 |

After electroporation, each ORF superpool combination listed in Table 4 is allowed to recover for 1 hour at 37° C. shaking at 250 rpm, and the cells are then diluted into 500 ml LB broth containing 0.3% ultra lowmelt agarose (Lonza SeaPrep agarose) for library amplification in soft gel (Elsaesser 2004). The 500 ml cell suspension for each ORF superpool combination is distributed among three 2.5 cm deep 15 cm petri plates and incubated at 4° C. for 1 hour to allow the agarose to form a semi-solid gel. The plates are then transferred to 37° C. and allowed to grow for 16 hours. The cells are then harvested by centrifugation at 10,000 g for 30 minutes. Each cell pellet is resuspended in 12 ml Resuspension Buffer A1 used for Machery Nagel NcucleoSpin 96 plasmid purification kits (Clontech). For each ORF superpool combination, 0.25 ml of cell suspension are then processed using the kit, following the manufacturer's recommendations. The remaining cells are frozen at −80° C. for future use.

Figure 8:
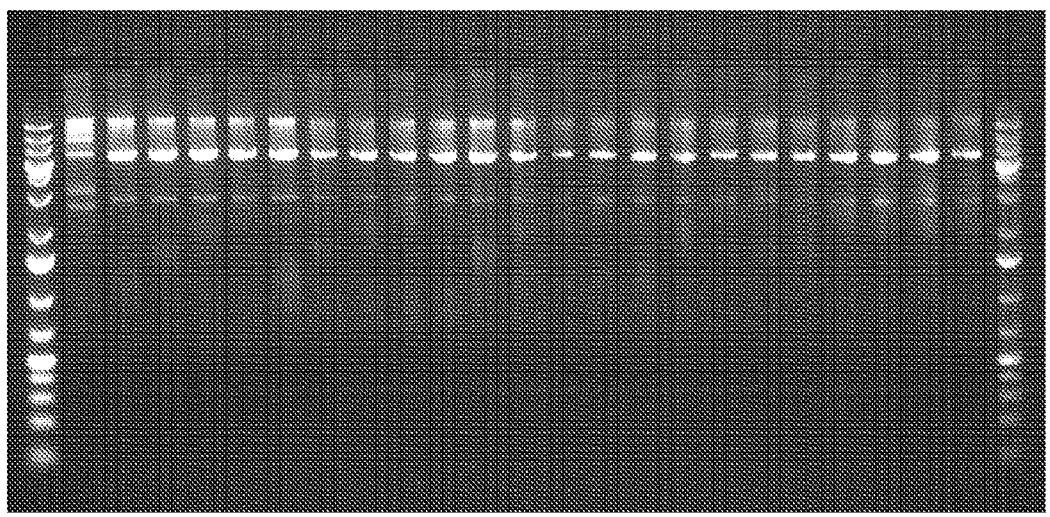
FIG. 8: 1% agarose gel showing the ORF Superpool combinations 1-17 and 19-24 after in vitro assembly into a fusion gene library and cloning in *E. coli*. Each lane represents 1 µg of library DNA digested with NheI, XhoI and PflMI restriction enzymes. NheI restricts the fully assembled fusion gene plasmid upstream of the 5' ORF; Xho I restricts downstream of the 3' ORF and PflMI restricts between the two ORFs. Thus, each ORF is excised from the fusion gene construct in the process. Each lane shows a characteristic smear indicating that many DNA fragments of varying size are present, which is characteristic of a DNA library. The major vector band is clearly visible at the top of the gel (5538 bp). Also visible is a smaller band of about 3 kb that represents a rearranged vector which arose with some regularity in the assembly reactions. The fuzzy band at the top of the gel is *E. coli* chromosomal DNA. The first and last lanes contain marker DNA of the following sizes (from bottom, in bp): 75, 200, 300, 400, 500, 700, 1000, 1500, 2000, 3000, 4000, 5000, 7000, 10000, 20000.

Following elution, the plasmid DNA is quantitated by spectrophotometric measurement. To check the library quality, 1 µg of DNA from each superpool combination is digested by NheI, PflMI and XhoI, restriction enzymes that cut upstream of the 5' ORF, between the two ORFs, and 3' of the 3' ORF in the fully assembled fusion gene vector, thus excising both fusion genes in the process. FIG. 8 shows the result for this digest for 23 of the 25 ORF combinations.

To transform yeast, the in vitro assembled and *E. coli* cloned library can either be transformed as separate superpool combinations or as a single pool with all combinations mixed together. Because of the size of the final fusion gene plasmids is dominated by the vector DNA (5538 bp), size differences between difference superpools result in less of a size bias than when working with the individual ORFs and as a result it is safe to pool all superpool combinations into a single sample for yeast transformation.

To verify that yeast transformants generated by transformation with either assembly method described above contain fusion genes consisting of random ORFs fused in-frame, 11 random yeast clones transformed with the randomized in-frame fusion gene library generated in vitro and cloned in *E. coli*, and 10 random yeast clones transformed with separate 5' and 3' ORF pools and vector fragment for assembly in yeast, were further analyzed by rescuing the plasmids contained in the yeast transformants into *E. coli* (Ward 1990, and as described below) and sequencing the inserts of these plasmids to confirm their structure. The results of this analysis confirmed that 4 out of 11 yeast clones generated by transformation with the randomized in-frame fusion gene library generated in vitro and cloned in *E. coli*, and 6 out of 10 yeast clones generated by transformation with separate 5' and 3' ORF pools and vector fragment for assembly in yeast, contained fusion genes containing 2 intact, full-length yeast ORFs fused in-frame and separated by an intact linker sequence. The remaining clones contained truncated 5' ORFs of unknown origin that appear to arise at some frequency when using either assembly method, as well as intact and full-length linker sequences and 3' ORFs. None of the ORFs observed in these 21 clones occurred more than once. These results confirm that both assembly methods described above result in a substantial proportion of yeast transformants which contain fusion genes consisting of pairs of random ORFs fused in-frame.

Library Assembly in Yeast and Library Transformations into Yeast

The yeast strain BY4741 (mat a his3D1 leu2D0 met15D0 ura3D0) is used for all transformations and screens (Brachmann 1998). To achieve assembly of a fusion gene library in yeast, this yeast strain is transformed separately with each of the 25 combinations of 5' and 3' ORF superpools. In each transformation, 200 fmol of a 5' ORF superpool is combined with 200 fmol of a 3' ORF superpool and with either 100 fmol of the single vector PCR fragment (5538 bp) or with 100 fmol each of the two vector fragments (4295 and 1626 bp) overlapping within the URA3 gene as described above. Each of the 25 combination is pre-mixed prior to transformation into yeast. Such transformations typically yield 4000-5000 colonies of yeast per transformation as described below, of which >90% contain fusion genes correctly assembled into the p416-GAL1 vector. For transformation with a library already cloned and expanded in *E. coli*, the transformations procedure summarized below yield about 250,000-300,000 transformants per microgram of cloned plasmid library DNA. Because each of the two approaches (in vitro assembly and library cloning in *E. coli* vs library assembly by transformation of yeast) is expected to result in different sequence biases (i.e. some ORFs preferentially incorporated into a collection of clones or transformants compared to others), it is advantageous to use both methods when screening for a specific phenotype. Nevertheless, because of the 50-60× higher transformation efficiency of yeast of the in vitro assembled and *E. coli* cloned library, this method is preferred for generating a very high number of transformants.

Yeast transformations are performed by the lithium acetate—heat shock method (Gietz 2002, Gietz 2006, Gietz 2007). The yeast strain BY4741 (Brachmann 1998) from a plate or an overnight culture is inoculated into 50 ml of YPD medium (20 g Bacto Peptone, 10 g Bacto Yeast Extract and 20 g Glucose per liter) at 30° C. on a shaker at 225 rpm from a starting density of 5×10$^6$ cells/ml to 2×10$^7$ cells/ml. The cells are harvested by centrifuging them at 3000 g for 5 min, the cells are then resuspended in 25 ml of sterile deionized water, centrifuged again, resuspended in 1 ml of sterile water, transferred to a 1.5 ml microcentrifuge tube, centrifuged for 30 sec at 3000 rpm and the supernatant aspirated. The cell pellet is then resuspended in 0.4 ml of sterile deionized water. The cell suspension is combined with 3.26 ml of transformation mix (2.4 ml of 50% w/v PEG 3350, 360 µl 1M Lithium acetate and 500 µl 10 mg/ml sheared, boiled salmon sperm DNA) and mixed well. Aliquots of DNA (100 ng-1 µg) are pipetted into separate 1.5 ml microcentrifuge tubes and combined with 360 µl of the cell suspension in transformation mix. The cell/DNA mixture is mixed thoroughly and is incubated at 42° C. on a shaker at 250 rpm for 40 minutes. The transformations are then centrifuged for 1 minute at 3000 rpm in a microcentrifuge, the supernatant aspirated and each cell aliquot resuspended in 0.5-1 ml sterile deionized water. Depending on the desired density of colonies, 10 µl to 1 ml of the cell suspension are plated with sterile 4 mm glass beads onto one 10 cm or 15 cm plate containing synthetic complete uracil dropout medium containing glucose as a carbon source (for 1 L, 6.7 g yeast nitrogen base, 0.77 g uracil dropout mix, 15 g Bacto agar, 120 µl 1 ON NaOH to bring the pH to 5.6-5.8, and 20 g glucose) synthetic complete medium uracil dropout medium with galactose as a carbon source (for 1 L, 6.7 g yeast nitrogen base, 0.77 g uracil dropout mix, 120 µl 10N NaOH to bring the pH to 5.6-5.8, 15 g Bacto Agar and, added after autoclaving, 100 ml sterile-filtered 20% galactose). The plates are opened on a benchtop to allow the liquid to dry and are then covered and incubated at 30° C. or at a selective temperature for several days.

The total possible number of sequence combinations resulting from random pairwise assembly of 5019 ORFs equals the square of this number=25.2 million. Typically, the goal of a screening project is to screen through 3× as many clones as the library complexity to have a >90% chance that each combination is represented among the transformants (assuming equal sequence representation among the DNA pools). In our case this corresponds to roughly 74 million transformants, which is possible in yeast assuming transformation efficiencies approaching 10$^6$ transformants per µg of DNA, which are routinely achievable with some protocol optimizations for a specific strain (Gietz 2007), especially when using a library that has been assembled in vitro and cloned in *E. coli*.

Screening for Fusion Genes Conferring Heat and Salt Tolerance

Following transformation, the cells are centrifuged for 1 minute at 5000 rpm and the supernatant is aspirated. The pellet is resuspended in 1 ml synthetic complete medium containing glucose as a carbon source (for 1 L, 6.7 g yeast nitrogen base, 0.77 g uracil dropout mix, 120 µl 10N NaOH to bring the pH to 5.6-5.8, and 20 g glucose), and each transformation is cultured for 2-3 hours at 30° C. on a shaker at 250 rpm followed by centrifugation of the cells, resuspension in 1 ml sterile deionized water, and plating on the appropriate selective medium.

For heat selection, cells are plated on synthetic complete medium uracil dropout medium with galactose as a carbon source (for 1 L, 6.7 g yeast nitrogen base, 0.77 g uracil dropout mix, 120 μl 10N NaOH to bring the pH to 5.6-5.8, 15 g Bacto Agar and, added after autoclaving, 100 ml sterile-filtered 20% galactose). The cells are spread on the plate using 10-15 4 mm sterile glass beads. The plates are left open to dry and are incubated at 30° C. for 24 hours followed by incubation at 40° C. for four days. Individual colonies that are able to resist the high temperature are visible 5 days after plating.

For salt selection, cells placed on a rotating shaker for 1.5 hours at 30° C., and are then plated on synthetic complete uracil dropout medium with galactose as a carbon source and containing 1M NaCl (for 1 L, 6.7 g yeast nitrogen base, 0.77 g uracil dropout mix, 120 μl 10N NaOH to bring the pH to 5.6-5.8, 15 g Bacto Agar, 58.44 g NaCl and, added after autoclaving, 100 ml sterile-filtered 20% galactose). The cells are spread on the plate using 10-15 4 mm sterile glass beads. The plates are left open to dry and are incubated at 30° C. for five days. Individual colonies that are able to resist the high salt are visible 5 days after plating.

Colonies that arise under selective growth conditions are picked and re-streaked on synthetic complete uracil dropout medium containing glucose as a carbon source (for 1 L, 6.7 g yeast nitrogen base, 0.77 g uracil dropout mix, 15 g Bacto agar, 120 μl 10N NaOH to bring the pH to 5.6-5.8, and 20 g glucose). After several days of growth at 30° C., the clones showing growth are picked into 1 ml synthetic complete uracil dropout liquid medium containing glucose as a carbon source (for 1 L, 6.7 g yeast nitrogen base, 0.77 g uracil dropout mix, 120 μl 10N NaOH to bring the pH to 5.6-5.8, and 20 g glucose) in a deep-well 96-well plate, and are grown on a shaker at 800 rpm at 30° C. for 2 days. The cells are then pelleted by centrifugation at 4000 rpm for 5 minutes in a benchtop centrifuge, the supernatant is poured off, and yeast plasmid DNA is purified using a commercial kit (for example the Zymoprep yeast plasmid miniprep kit from Zymo Research), following the manufacturer's instructions. The resuspended DNA is introduced into the DH10B (Life Technologies) or EC100 (Epicentre Technologies) strain of *E. coli* by electroporation by combining 2 μl DNA with 20 μl electrocompetent cells on ice, transferring into a 1 mm gap size electroporation cuvette, electroporating at 1.5 kV using a Bio-Rad MicroPulser electroporator, suspending the cells in 0.5 ml LB broth, allowing the cells to recover for 1 hour at 37° C. on a shaker and plating 0.2 ml aliquots of transformed cells onto a 10 cm plate containing LB agar medium with 50 μg/ml carbenicillin.

Bacterial colonies arising on the plate are picked, 2 colonies for each yeast clone used for DNA isolation, and are grown up and plasmid DNA prepared from them using standard methods (Sambrook 1989). The plasmid DNA is digested with restriction enzymes cutting 5' of the 5' ORF (NheI), 3' of the 3' ORF (XhoI) and in between the two ORFs (PflMI) to verify that the rescued plasmid contains a fusion protein.

The cloned plasmid DNA is re-introduced into yeast by lithium acetate—heat shock transformation as described above (Gietz 2006), individual colonies arising from the transformation are picked, suspended in deionized water and 5 μl aliquots spotted in serial 10× dilutions on synthetic complete uracil dropout medium with galactose as a carbon source, or on YPGal rich medium containing galactose as a carbon source (20 g Bacto Peptone, 10 g Bacto Yeast Extract and 20 g galactose per liter), and incubated at 40° C. to verify heat tolerance, or spotted in serial 10× dilutions on the same media with galactose as a carbon source and containing 1M NaCl and incubated at 30° C. to verify salt tolerance.

Yeast clones transformed with candidate fusion gene constructs are compared to transformants with the p416-GALL empty vector for growth under selective conditions to establish the activity of the fusion gene constructs.

Figure 10:
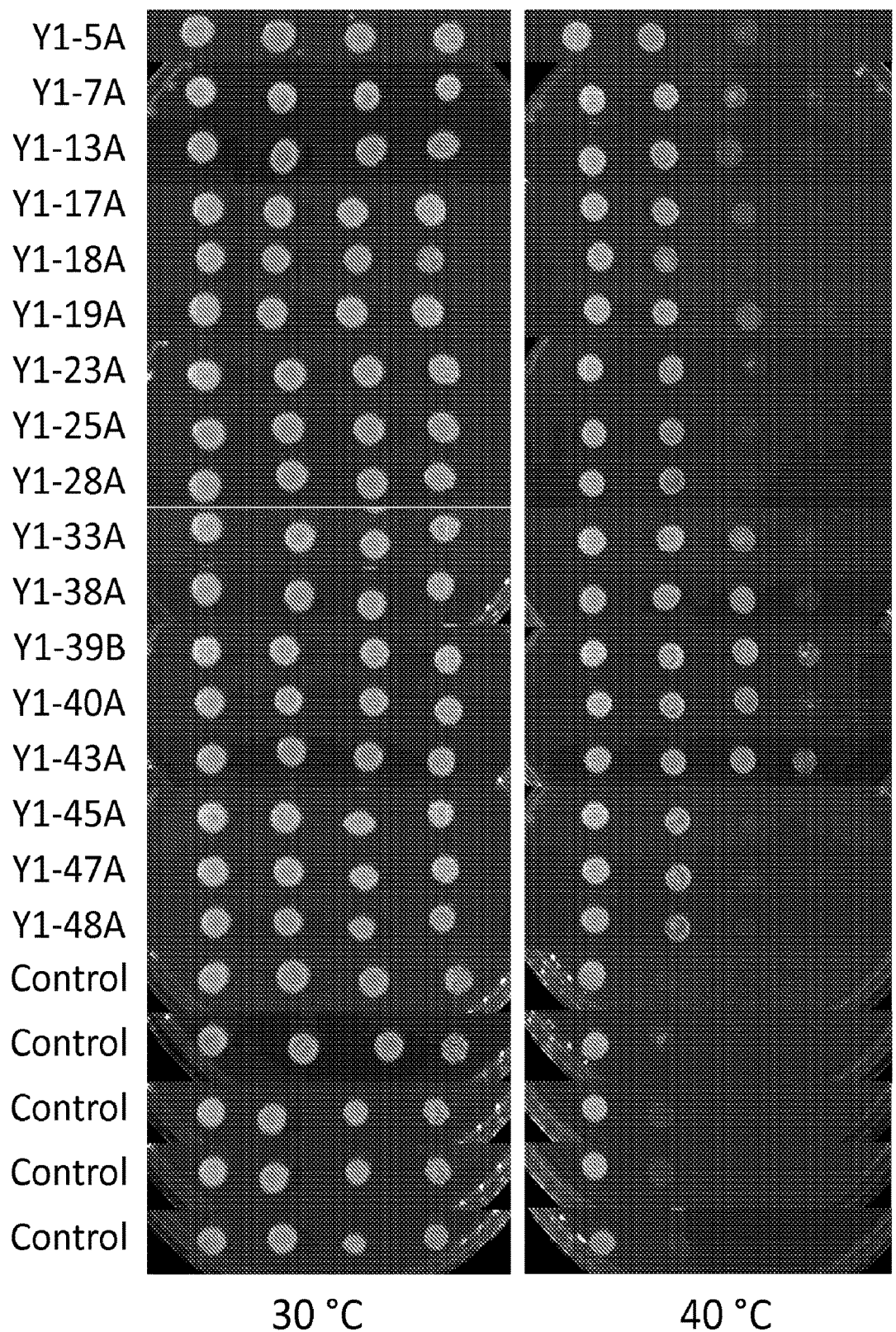
FIG. 10: Composite images of spot assays demonstrating heat tolerance of the fusion genes listed in FIG. 9. Each fusion gene was re-transformed into yeast strain BY4741 and selected for presence of the plasmid. Transformed cells were suspended in deionized water, adjusted for uniform cell density, and spotted in 4 serial 10× dilutions, on duplicate plates with synthetic complete uracil dropout medium containing galactose as a carbon source. The plates were incubated at 30° C. and 40° C. as indicated in the figure. The fusion gene names are indicated to the left of each row of spots. Heat tolerance is visible by enhanced growth at 40° C. compared to the control (strain BY4741 transformed with plasmid p416-GAL1). Multiple controls are shown, from multiple plates from which the composite image originated.

Examples of fusion genes isolated from a screen for heat tolerance (ability to grow at 40° C.) are listed in FIG. 9, and the ability of yeast cells transformed with these clones to grow at elevated temperature is demonstrated in FIG. 10. The cells spotted on the plates shown in FIG. 10 represent re-transformants of strain BY4741 with the fusion gene clones listed in FIG. 9, and confirm their ability to confer heat tolerance.

Screening for Fusion Genes Conferring Butanol Tolerance Phenotypes:

The pooled libraries containing randomized in-frame fusion polynucleotide are transformed into laboratory strains of yeast and then grown under conditions that select for the presence of the plasmids and expression of the randomized in-frame fusion polypeptides encoded by the randomized in-frame fusion polynucleotide is induced. Four different approaches are used to select or screen for butanol-tolerant transformants. Two of these involve survival selections, using lethal concentrations of butanol to isolate cells with the ability to survive the alcohol. The other two approaches aim to isolate cells with improved growth properties in the presence of sub-lethal concentrations of butanol. On selection each of the two survival selections and the two growth tolerance selections involve growth and selection on solid medium while the other uses growth in liquid medium followed by selection or screens on solid medium. The three selection and screening approaches are summarized in Table 5, with the concentration ranges of butanol based on published information (Knoshaug 2008).

TABLE 5

Media and growth conditions for isolating butanol-tolerant *S. cerevisiae* transformants

| Selection type | Solid or liquid medium | Butanol concentration | Incubation time | Selection based on: |
| --- | --- | --- | --- | --- |
| Survival | solid | Lethal: 2.5-3.0% butanol | 5-10 days | Colonies growing on plates |
| Growth tolerance | solid | Sub-lethal: 1.5-2.5% butanol | 5-10 days | Colony size |
| Survival | liquid | Lethal: 2.5-3.0% butanol | 12-24 hours | Surviving cells |
| Growth tolerance | liquid | Sub-lethal: 1.5-2.5% butanol | 24-72 hours | Colony size |

The four selection schemes are preceded by careful titration, under the exact plating or culturing conditions and cell densities used later with bulk yeast transformants to arrive at the optimal butanol concentration for each selection. Mock transformations, containing yeast cells combined with carrier DNA and otherwise treated as in a real transformation, are used for these titration experiments. All cultures are grown at 30° C. under carefully controlled, constant conditions to maintain uniformity in the selections.

For survival selection on solid medium, yeast cultures at specific, optimal growth densities re harvested and transformed with randomized in-frame fusion polynucleotide library DNA. The transformed cultures are grown in uracil dropout medium in liquid culture containing galactose for 2 hours following transformation to allow the cells to recover from transformation shock and begin inducing expression of the encoded randomized in-frame fusion polypeptides. The cell density is then determined and the cells are plated at a constant cell density and an expected colony density of roughly 50,000 transformants per 15 cm selective plate containing solid minimal medium lacking the specific nutrients used to select for presence of the centromeric plasmid, and containing galactose and butanol. Small aliquots of the transformation are plated on the plates with the same medium, but lacking butanol as controls. The plates are sealed and incubated at 30° C. until surviving colonies become visible.

Alternatively, yeast cells are transformed with fusion gene library DNA in the same manner as described above. Cells are plated on synthetic complete uracil dropout medium containing glucose as a carbon source (for 1 L, 6.7 g yeast nitrogen base, 0.77 g uracil dropout mix, 20 g Bacto agar, 120 µl 1 ON NaOH to bring the pH to 5.6-5.8, and 20 g glucose), and are incubated at 30° C. until transformed colonies become visible. The cells are then removed from the plates by scraping or by using glass beads to suspend the colonies in liquid added to the top of the plates. The cells are diluted to an OD600 of 0.1 and grown for 4 h in liquid synthetic complete uracil dropout medium containing raffinose as a carbon source (for 1 L, 6.7 g yeast nitrogen base, 0.77 g uracil dropout mix, 120 µl 10N NaOH to bring the pH to 5.6-5.8, and 20 g raffinose) to allow the cells to metabolize the remaining glucose, and to remove the catabolic repression of the GAL1 promoter. The cells are then diluted again to a density of OD600=0.1 into YPGal rich medium containing galactose as a carbon source and grown for 2 hours on a shaker at 30° C. to induce the expression of the fusion genes through the GAL1 promoter. The cell density of the resulting suspension is determined by counting with a hemocytometer, and cells are plated at a density of $2.5 \times 10^7$ cells per 15 cm plate (roughly 150,000 cells per sq cm) on YPGal agar medium containing 2-3% butanol, 2% being sub-lethal and 3% being lethal. The plates are incubated at 30° C. for 4-10 days and are then examined for colonies (when using lethal concentrations of butanol in the plates) or for colonies larger than the background (when using sub-lethal concentrations of butanol in the plates).

Because screens on solid media allow visualization of individual clones or transformants, they are particularly useful for identifying transformants expressing genes contributing to rapid growth which are clearly visible as larger colonies. A difference as little as a few percent in doubling time can lead to a measurable difference in colony size. For example, a 48 hour growth period for a strain with an average doubling time of 2 hours allows 24 doublings, while a strain with a 5% faster average doubling time of 114 minutes doubles 25.3 times, leading to a 2.5-fold difference in cell number which is clearly reflected in colony size. Thus, plating on solid media containing sub-lethal concentrations of butanol allows identification of transformants that have a growth advantage in the presence of butanol, indicative of butanol tolerance. Such screens have been used by others for isolation of genes contributing to ethanol tolerance (Hong 2010).

For resistance selection in liquid medium, yeast cultures are transformed with fusion gene library DNA in the same manner as described above. Cells are plated on synthetic complete uracil dropout medium containing glucose as a carbon source (for 1 L, 6.7 g yeast nitrogen base, 0.77 g uracil dropout mix, 20 g Bacto agar, 120 µl 10N NaOH to bring the pH to 5.6-5.8, and 20 g glucose), and are incubated at 30° C. until transformed colonies become visible. The cells are removed from the plates by scraping or by using glass beads to suspend the colonies in liquid added to the top of the plates, and are then diluted to an OD600 of 0.1 and grown for 4 h in liquid synthetic complete uracil dropout medium containing raffinose as a carbon source (for 1 L, 6.7 g yeast nitrogen base, 0.77 g uracil dropout mix, 120 µl 10N NaOH to bring the pH to 5.6-5.8, and 20 g raffinose) to allow the cells to metabolize the remaining glucose, and to remove the catabolic repression of the GAL1 promoter. The cells are then diluted again to a density of OD600=0.1 into YPGal rich medium containing galactose as a carbon source and grown for 2 hours on a shaker at 30° C. to induce the expression of the fusion genes through the GAL1 promoter. Butanol is then added to the cultures to 3%, the culture is capped to prevent evaporation and grown at 30° C. with gentle shaking for an additional 2-7 days. The cells remaining at the end of the selection period are then spun down and their plasmid DNA isolated for cloning into *E. coli* and re-transformation into yeast and another cycle of selection, or cells are plated on synthetic complete uracil dropout medium containing glucose as a carbon source to isolate surviving cells.

Colonies arising on selective plates are picked, or pools of yeast cells surviving selection in liquid medium are collected by centrifugation, expanded in selective medium if necessary, and used for plasmid extractions and plasmid propagation in *E. coli*. Two *E. coli* colonies are picked for each yeast transformant and 20 *E. coli* colonies are picked for each pool of surviving yeast cells from liquid selections, the DNA isolated and checked by restriction digestion. The plasmid DNA is then re-introduced into yeast for phenotype confirmation.

For simplicity, all plasmids are checked using two standard butanol-tolerance assays conducted in 96-well formats. The two assays use lethal and sublethal concentrations of butanol, respectively, in liquid culture. After a period of culture under lethal conditions, or several passages of growth under sublethal conditions, the cultures are serially diluted and replica-plated onto solid media to assess the density of surviving cells. These assays allow rapid and uniform testing of all isolated plasmids with the necessary controls, and allow rapid validation of randomized in-frame fusion polynucleotide conferring survival or growth advantages in the presence of butanol.

Characterization of Positive Clones

Randomized in-frame fusion polynucleotide expression constructs conferring the most dramatic or broad phenotypes are sequenced to identify the active genes. The results are tabulated and the best randomized in-frame fusion polynucleotide chosen for future work. Sequences identified repeatedly within distinct randomized in-frame fusion polynucleotide are used in future screens or as part of ORF collections. ORF collections containing randomized in-frame fusion polynucleotide already known to confer a desirable phenotype may be smaller than the whole-genome ORF collections described above for *E. coli*, which has many advantages including smaller library size, less expensive and faster screens, and amenability in organisms with lower transformation efficiencies, including algae and plants.

Example 3: Isolation of Randomized in-Frame Fusion Polynucleotides Capable of Conferring Higher Biomass, Accelerated Growth Rate or Alcohol Resistance to Cyanobacteria i.e. *Synechococcus elongatus*

Introduction:

Cyanobacteria have been engineered to produce a variety of chemicals, including ethanol (Deng 1999, Dexter 2009, Gao 2012), isobutyraldehyde (Atsumi 2009), isobutanol (Atsumi 2009), n-butanol (Lan 2011, Lan 2012), 1,3-butanediol (Oliver 2013), acetone (Zhou 2012), ethylene (Takahama 2003), isoprene (Lindberg 2010), fatty acids and fatty alcohols (Liu 2011, Tan 2011) and sugars (Ducat 2011, Ducat 2012), in some cases with promising results (i.e. Ducat 2011, Oliver 2013). Because of their relative genetic simplicity compared to plants and eukaryotic algae, low input requirements for their cultivation, ability to resist stresses, and amenability to genetic manipulation, cyanobacteria are among the photosynthetic organisms that will play a major role in this global shift towards biological production (Ducat 2011, Robertson 2011, Ruffing 2011).

Cyanobacteria are also of interest because of their high inherent rates of growth and carbon fixation; as a result, these organisms hold much promise as sources of biomass that can serve as feedstocks for fuel and chemical production. Nevertheless, biomass productivity is genetically complex and poorly understood, and therefore difficult to engineer. Increasing the rates of biomass accumulation in industrially promising cyanobacterial species is one of the obstacles faced by the nascent cyanobacterial biotechnology industry in its attempts to develop cyanobacteria into economical production organisms.

This example describes engineering of higher biomass, accelerated growth rate or alcohol resistance in the *cyanobacterium Synechococcus elongatus* using randomized in-frame polynucleotide fusions. *S. elongatus* is an important experimental *cyanobacterium* that is fast-growing and easily cultured, easily and efficiently transformable (Golden 1987, Tsinoremas 1994, Elhai 1994, Vioque 2007, Clerico 2007, Flores 2008, Heidorn 2011).

Sequence Identification and PCR Primer Design:

A complete collection of *Synechococcus elongatus* gene sequences are generated based on the reference sequence of *S. elongatus* strain PCC7942 available from the J. Craig Venter Institute (JCVI) Comprehensive Microbial Resource genome data collection (available on the CMR-JCVI web site on the internet). The sequence annotation of this genome is used for identifying the start and stop codons of each gene.

Figure 6:
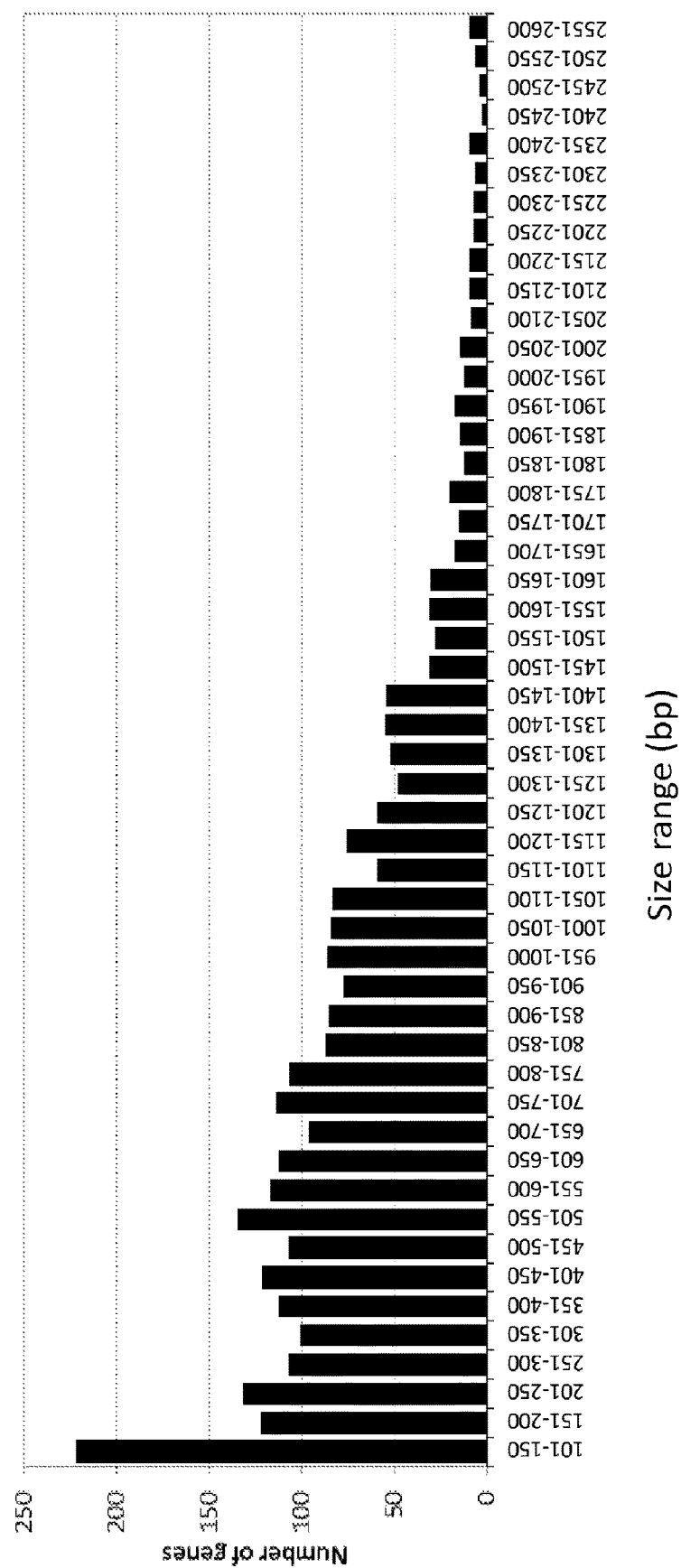
FIG. 6: Size distribution of selected *Synechococcus elongatus* genes, 101-2598 bp in length, used as a starting collection of sequences for a randomized in-frame polynucleotide fusion library.

The JCVI annotation lists 2991 total protein coding genes, ranging in length between 21 bp, encoding a protein of 7 amino acids, and 4,785 bp, encoding a protein of 1595 amino acids. Of these ORFs, 2958 are between 100 bp and 3,000 bp in length. The length of genes used as input sequences is capped at 3000 bp, preferentially 2604 bp, which increases the likelihood of successful PCR amplification and correct folding of the resultant in-frame fusion polypeptides or proteins. The result is a final collection of 2,925 ORFs for PCR amplification, that are between 100 and 2604 bp in length. The average length of this sequence collection is 785 bp and the median length is 693 bp. The size distribution of these *S. elongatus* ORFs is shown in FIG. 6.

PCR primers are designed based on the known start and stop codons of each ORF, including 24 bp of coding sequence from each end. Two different sets of primers are designed for each ORF, so that two different PCR products are generated, one for cloning the ORF into the 5' position of the fusion gene and the other for placing it 3'. The two amplicons for each ORF only differ in the presence of a stop codon (occurring only in the ORFs destined for the 3' position of the randomized in-frame fusion polynucleotide library) and in their conserved flanking sequences.

Each primer contains 16 bases of conserved sequence at the 5' end that serves two purposes. First, the extra sequence allows efficient PCR amplification of pools of ORFs using conserved PCR primer sequences that are able to amplify all the ORFs in a collection without biasing the representation of different ORFs with respect to one another (Dahl 2005, Myllykangas 2011, Natsoulis 2011). Second, they contain homology to the expression vector (see details below) and to the conserved sequences at the ends of the randomized in-frame fusion polynucleotide partner, enabling rapid and efficient, homology-dependent assembly of the randomized in-frame fusion polynucleotides in the vector (see FIG. 3).

The 5'-terminal 16 nucleotides in the 3' PCR primer of ORFs destined for the 5' position in a fusion gene, and the 5'-terminal 16 nucleotides in the 5' PCR primer of ORFs destined for the 3' position in a fusion gene, form part of a linker sequence that separates the two ORFs. This 60 bp linker sequence encodes a 20 amino acid peptide (SEQ ID NO: 25104) rich in glycine, serine and alanine, which is loosely based on sequences used by others when connecting two ORFs in a fusion gene (Arai 2001, Eldridge 2009, Wang 2010). This linker sequence is fully encoded in the second or conserved stage of PCR amplification (see below), resulting in the addition of conserved coding sequences to the 3' ends of the ORFs destined for the 5' position of the randomized in-frame fusion polynucleotides and the 5' end of the ORFs destined for the 3' position in the randomized in-frame fusion polynucleotides.

Because two entire sets of cyanobacterial ORFs need to be generated, one for the 5' position in the fusion genes and the other for the 3' position, all procedures described below are performed in duplicate for the two ORF positions.

Cyanobacterial Strains and Genomic DNA Preparation:

The chosen *Synechococcus elongatus* genes are PCR amplified from strain PCC7942. This strain is available from the Institut Pasteur Culture Collection of Cyanobacteria, and can be used as a source of high-purity genomic DNA from which genes of interest can be amplified.

The cyanobacterial strain that serves as the source of ORFs is grown in liquid culture using standard growth conditions (Bustos 1992, Kulkarni 1997, Mutsuda 2003, Clerico 2007) in BG11 medium or modified BG11 medium. Modified BG-11 liquid medium (BG11M, Clerico 2007) is made up as follows: 1.5 g/L NaNO3, 0.039 g/L K2HPO4, 0.075 g/L MgSO4.7H2O, 0.02 g/L Na2CO3, 0.027 g/L CaCl2, 0.001 g/L EDTA, 0.012 g/L FeNH4 citrate, and 1 mL of the following microelement solution: 2.86 g/L H3B03, 1.81 g/L MnC12.4H2O, 0.222 g/L ZnSO4.7H2O, 0.391 g/L Na2MoO4, 0.079 g/L CuSO4.5H2O, and 0.0494 g/L Co(NO3)2.6H2O. Solid medium is made by combining equal volumes of twice concentrated BG-11M liquid medium and Difco agar solution (3% in sterile water) autoclaved separately and mixed together; filter-sterilized Na2SO3 is added to 1 mM final concentration.

Cells are pelleted by centrifugation and then resuspended in 1/10 of the original culture volume using 20 mM Tris pH 8.0, 10 mM EDTA and 100 mM glucose. The cells are lysed by adding 1/100 volume 10 mg/ml hen egg lysozyme dissolved in 10 mM Tris pH 8.0, 10 mM EDTA and adding 1/20 volume 10 mg/ml DNA-se free RNAse A, mixing well and incubating at room temperature for 15 minutes. Cell lysis and release of genomic DNA is completed by treatment with proteinase K. To the lysed cells is added 1/10 volume of 1M Tris, 0.5M EDTA, pH 9.5 and 1/100 volume of a 20 mg/ml solution of proteinase K. The lysed cells are mixed gently by capping the tube and inverting it, and the mixture is incubated at 50° C. for 2 hours with occasional gentle mixing. The DNA is then extracted twice with an equal volume of phenol-chloroform (pH 7.0) followed by one additional extraction with an equal volume of chloroform. The DNA is precipitated by the addition of 1/10 volume 3M sodium acetate pH 5.5 and 2.5 volumes ethanol (or 1 volume isopropanol). The tube is immediately inverted after addition of the alcohol, and the DNA is visible as a stringy white precipitate. To avoid co-precipitating other impurities from the cell (residual protein or carbohydrates), the precipitated DNA is removed from the alcohol solution using a clean pipet tip or a pasteur pipet and is transferred to a clean tube containing 70% ethanol. The tube is capped and inverted multiple times to remove salts from the DNA precipitate. The pellet is collected by centrifugation, the ethanol removed by aspiration and the pellet is dried in an air flow hood to remove excess ethanol. The pellet is dissolved in 1×TE (10 mM Tris pH 8.0, 0.1 mM EDTA). Further purification of the DNA can be performed using column chromatography or cesium chloride density centrifugation (Sambrook 1989).

Other DNA preparation methods, yielding equivalent results to the one described here, have been described in the literature (Clerico 2007, Heidorn 2011).

Expression Vectors

A simple and standard expression vector is used to express all fusion proteins. The S. elongatus $P_{trc}$ promoter inducible by isopropyl-β-D-thiogalactopyranoside (IPTG, Geerts 1995, Kutsuna 1998) is frequently used and effective for the expression of genes in S. elongatus. In addition, the expression vector contains the NS1 or NS2 neutral site elements that direct site-specific integration into the S. elongatus chromosome (Mutsuda 2003), a suitable terminator (Wang 2012), antibiotic resistance marker gene(s) and the high-copy pMB1 plasmid replicon from pUC19 (Yanish-Perron 1985). The pUC19 vector is a convenient source of a plasmid backbone (pMB1 replicon), an antibiotic-resistance polynucleotide (e.g. β-lactamase from Tn3 conferring ampicillin resistance) and the E. coli lac promoter/operator and terminator sequences. These sequences are PCR amplified from pUC19 and used as a source of the plasmid backbone for cloning and expression of randomized in-frame fusion polynucleotides as illustrated in FIG. 3. For example, the PCR primers 5'-agctgtttcctgtgtgaaattgtt-3' and 5'-ttaagccagccccgacacccgcca-3' can be used to PCR amplify such a fragment from pUC19. The regions of homology to this expression vector fragment that are included in the 5' end of the 5' ORF and in the 3' end of the 3' ORF (see FIG. 3) correspond to the same DNA sequences specified by these two PCR primers.

As an alternative to the $P_{trc}$ promoter system for expression of randomized in-frame fusion polynucleotides, other cyanobacterial promoters can be used as described in the literature (Ruffing 2011, Wang 2012). Alternatively, synthetic promoters can be developed from partially randomized sequences containing the consensus elements for bacterial expression (Jensen 1998a, Jensen 1998b, Hammer 2006, De May 2007).

To test a candidate promoter for suitability for the expression of randomized in-frame fusion polynucleotides, the selected promoters and their associated 5'UTRs are synthesized as 250 bp DNA fragments and cloned upstream of the E. coli lacZ beta-galactosidase gene in a vector containing a selectable marker (Heidorn 2011, Ruffing 2011). Terminators are placed upstream of the promoter fragments to prevent read-through transcription from promoters present elsewhere on the plasmid. The resulting constructs are transformed into S. elongatus and the transformants assayed for beta-galactosidase activity (Bustos 1991). Firefly luciferase is also suitable as an assayable marker gene and can be used for promoter testing instead of lacZ (Kondo 1993, Andersson 2000).

The plasmids described here for expression of randomized in-frame fusion polynucleotides are based on high-copy number plasmids such as those containing the pMB1 origin of replication. However, other plasmid systems are also suitable for this work. For example an F'-based plasmid such as pBeloBAC11 (Shizuya 1992) or broad-host-range plasmid systems (Heidorn 2011) can be used to clone randomized in-frame fusion polynucleotides using the same promoters as described above, or using a different set of promoters. Any plasmid backbone that allows cloning and propagation of sequences of interest in any suitable host cell can be used for transformation of S. elongatus after cloning and plasmid purification (Heidorn 2011).

Fusion Gene Design:

For example, a hypothetical polynucleotide sequence A, coding for a peptide or protein, can be part of a starting collection of polynucleotides intended to be used for the construction of a collection of randomized in-frame fusion polynucleotides. The goal of generating the collection of randomized in-frame fusion polynucleotides is to have each polynucleotide in the starting collection, including polynucleotide A, present at the 5' position of a series of randomized in-frame fusion polynucleotides, and to have the same sequence present in the 3' position of a different series of randomized in-frame fusion polynucleotides. In each of these two series of randomized in-frame fusion polynucleotides, the polynucleotide A is fused with as many other members of the starting collection as feasible with the available methods for generating such fusions. In order to enable these separate series of fusions, with polynucleotide A in a 5' or in a 3' position with respect to the other polynucleotides present in the starting collection, two different versions of the polynucleotide sequence A are generated. The version of polynucleotide sequence A intended for use in the 5' position does not contain a stop codon and has 5' homology (or other sequence compatibility for cloning purposes) to the promoter region of the expression vector. The version of polynucleotide sequence A intended for use in the 3' position does contain a stop codon and has 3' homology (or other sequence compatibility for cloning purposes) to the terminator region of the expression vector.

The sequence separating the two ORFs in a randomized in-frame fusion polynucleotide (labeled as 'linker sequence' in FIG. 3) encodes a short peptide that is rich in glycine and serine residues. Such a peptide is expected to be unstructured and will provide a flexible protein spacer separating the two members of a randomized fusion protein while being relatively resistant to proteolysis. Examples of suitable linker peptide sequences are GGGGSGGSGGSGGGS (SEQ ID NO: 25117) or SGGSSAAGSGSG (SEQ ID NO: 25118) or SAGSSAAGSGSG (SEQ ID NO: 25119, Wang 2010). Alternatively, alpha-helical linker sequences can be used, for example the sequence A(EAAAAK)$_n$A, n=2-5 (SEQ ID NO:S 25120 to 25123, Arai 2001).

Sequence Amplification:

Each ORF is PCR amplified with polynucleotide-specific primers containing 24 polynucleotide-specific bases at the 3' end and 16 bp of conserved sequences at the 5' ends. The amplification is performed for each polynucleotide individually, or for pools of polynucleotides simultaneously.

For individual amplification, the two primers, each at a final concentration of 0.5-5 μM, are combined with 10-1000 ng of E. coli genomic DNA, PCR buffer and thermostable polymerase in a total reaction volume of 1-50 μl. A high-fidelity thermostable polymerase such as Phusion® polymerase can be used. For Phusion® polymerase, the PCR amplicons are generated by 2 minutes denaturation at 95° C. followed by 10-35 cycles of 20 seconds at 95° C., 20 seconds at 60° C. and 1 min/kb at 72° C. (minimally 30 seconds at 72° C.). The efficiency of formation of the PCR product is measured by agarose electrophoresis or by fluorescent spectroscopy using a fluorometer such as a Qubit® fluorometer (Life Technologies). Successful PCR reactions can be purified using silica resins suitable for DNA purification. Unsuccessful reactions are repeated by varying the $Mg^{+2}$ concentrations in the PCR reaction and/or other reaction conditions. Following successful amplification of each ORF, the concentration of each PCR product is normalized, and products corresponding to specific size ranges are pooled for cloning.

Individual amplification has the advantage that the amplification of each ORF is performed and monitored separately, allowing approximately equivalent representation of each ORF in the final pool of ORFs. It has the disadvantage that a large number of PCR reactions need to be performed and assayed in parallel, requiring robotics and optimization of a large number of amplifications.

For pooled amplification, ORFs are pooled by size, because the efficiency of PCR amplification is strongly size dependent, and because the PCR conditions (extension time at 72° C., see above) depend on the size of the amplicon. The ORFs are separated into any number of size pools. A smaller number of size pools has the advantage that the amplification can be done in a smaller number of samples, saving time and reagents. A large number of size pools has the advantage that the complexity of each pool is lower, implying higher concentrations of each primer pair and thus a higher likelihood of successful amplification of each polynucleotide.

A plausible and convenient number of pools to use for gene amplification is 96 pools of 30-31 genes each, filling one 96-well plate (96 pools×30.81 genes on average=2958 genes total). To arrive at the assignment of each gene to a pool, the genes and their corresponding primer pairs are sorted based on gene size and primers assigned to each pool from contiguous sets of primers from the sorted list. When subdividing the total number of amplifications into 96 pools, 31 genes of identical or similar size=62 primers are assigned to each of 78 pools, and the remaining 18 pools each contain 60 primers corresponding to 30 genes.

Each ORF is PCR amplified with polynucleotide-specific primers containing 20-30 polynucleotide-specific bases at the 3' end and the conserved sequences at the 5' ends. The amplification is performed for each polynucleotide individually, or for pools of polynucleotides simultaneously.

For individual amplification, the two primers, each at a final concentration of 0.5-5 µM, are combined with 10-1000 ng of *E. coli* genomic DNA, PCR buffer and thermostable polymerase in a total reaction volume of 1-50 µl. A high-fidelity thermostable polymerase such as Phusion® polymerase can be used. For Phusion® polymerase, the PCR amplicons are generated by 2 minutes denaturation at 95° C. followed by 10-35 cycles of 20 seconds at 95° C., 20 seconds at 60° C. and 1 min/kb at 72° C. (minimally 30 seconds at 72° C.). The efficiency of formation of the PCR product is measured by agarose electrophoresis or by fluorescent spectroscopy using a fluorometer such as a Qubit® fluorometer (Life Technologies). Successful PCR reactions can be purified using silica resins suitable for DNA purification. Unsuccessful reactions are repeated by varying the $Mg^{+2}$ concentrations in the PCR reaction and/or other reaction conditions. Following successful amplification of each ORF, the concentration of each PCR product is normalized, and products corresponding to specific size ranges are pooled for cloning.

Individual amplification has the advantage that the amplification of each ORF is performed and monitored separately, allowing approximately equivalent representation of each ORF in the final pool of ORFs. It has the disadvantage that a large number of PCR reactions need to be performed and assayed in parallel, requiring robotics and optimization of a large number of amplifications.

For pooled amplification, ORFs are pooled by size, because the efficiency of PCR amplification is strongly size dependent, and because the PCR conditions (extension time at 72° C., see above) depend on the size of the amplicon. The ORFs are separated into any number of size pools. A smaller number of size pools has the advantage that the amplification can be done in a smaller number of samples, saving time and reagents. A large number of size pools has the advantage that the complexity of each pool is lower, implying higher concentrations of each primer pair and thus a higher likelihood of successful amplification of each polynucleotide. A convenient number of size pools corresponds to the number of wells in one or two 96-well plates. For example, 192 pools of 15-16 ORFs each (192 pools×15.23 ORFs on average=2925 ORFs total; this corresponds to 45 pools containing 16 primer pairs each, and 147 pools containing 15 primer pairs each).

Pooled PCR amplification is performed in three steps: 1) an initial amplification using gene-specific primers followed by 2) bulk-up of each ORF pool using conserved primers, followed by further pooling, size selection on gels and 3) a third amplification step resulting in the final length PCR products. The three amplification steps are referred to as $1^{st}$ stage, $2^{nd}$ stage and $3^{rd}$ stage amplifications, respectively.

All PCR amplifications are performed using Phusion™ Hot Start II thermostable high-fidelity polymerase (Thermo Scientific™). The enzyme is supplied with a 5×HF amplification buffer which is used for all reactions. Amplifications are performed in 20 µL or 50 µL reaction volumes, as noted below. All amplifications are performed on T100 thermal cyclers (Bio-Rad Laboratories) containing 96-well blocks. The deoxynucleotide triphosphates (dNTPs) used in all amplifications are a stock containing 10 mM of each dNTP, also obtained from Thermo Scientific®. Deionized water is used in all reactions and to make all solutions not supplied with the polymerase.

All PCR Amplifications Follow the Same General Procedure:

1. A PCR mix as described below is prepared for each stage of the PCR reaction, and is kept cold until inserted into the thermal cycler.

2. The samples are mixed thoroughly and then centrifuged at 4000 rpm for 1 minute to bring the reaction contents to the bottom of the tube or well in a plate.

3. The plates or tubes are inserted into a thermal cycler.

$1^{st}$ Stage Amplification:

First stage amplifications are conducted using pools of sequence-specific PCR primers as noted above. Each amplification is performed in 20 µl total volume, using 2 µL of 10 ng/µL *Synechococcus elongatus* strain PCC7942 genomic template DNA per reaction. To each reaction are added 2.5 µL primer pools from 100 µM stocks to provide a total final primer concentration of 12.5 µM. Each primer pool contains either 15 or 16 primer pairs; and final individual primer concentrations are approximately 0.39-0.42 µM.

The 1st stage PCR reaction mix is set up in 20 µl total volume and is mixed from the following components: 4 µl 5× Phusion® HF Buffer, 0.4 µl 10 mM dNTPs, 10.7 µl deionized $H_2O$, 2 µl 10 ng/µl genomic template DNA, 2.5 µL primer pools (100 µM), 0.4 µl Phusion™ Hot Start II thermostable polymerase (2 units/µl). The PCR cycling conditions are as follows: initial denaturation at 98° C. for 45 sec, 10 cycles consisting of three steps each (98° C. for 10 seconds, 60° C. for 30 seconds and 72° C. for 3 minutes), a final extension step at 72° C. for 3 minutes and a soak at 4° C. until removal of the samples from the thermal cycler. After the PCR amplification is complete, the samples are removed from the thermal cycler, mixed thoroughly, and centrifuged at 4000 rpm for 1 minute to provide the $1^{st}$ Stage amplification product.

2nd Stage Amplification:

The primers used in $2^{nd}$ stage amplifications are single primers with homology to the conserved portions of the $1^{st}$ stage amplification primers. The $2^{nd}$ stage primers are prepared as pairwise mixes, each containing equimolar amounts of the two primers and containing a total primer concentration of 20 µM.

The $2^{nd}$ stage PCR reaction mix is set up in 50 µl total volume and is mixed from the following components: 10 µl 5× Phusion® HF Buffer, 1 µl 10 mM dNTPs, 22 µl deionized $H_2O$, 10 µl $1^{st}$ stage reaction product, 6 µl $2^{nd}$ stage primer mix (20 µM) and 1 µl Phusion™ Hot Start II thermostable polymerase (2 units/µl). The PCR cycling conditions are as follows: initial denaturation at 98° C. for 45 sec, 25 cycles consisting of two steps each (98° C. for 20 seconds and 72° C. for 3 minutes), a final extension step at 72° C. for 3 minutes and a soak at 4° C. until removal from the thermal cycler.

After the PCR amplification is complete, the samples are removed from the thermal cycler, mixed thoroughly, and centrifuged at 4000 rpm for 1 minute.

To allow more efficient downstream processing of the samples, the 192 multiplex PCR samples are consolidated into 24 larger pools by pooling 8 samples into one. The amount of product in each multiplex PCR reaction is first quantitated to allow equimolar pooling of the different sized fragment collections. This is done either by conducting gel electrophoresis on each multiplex reaction and quantitating the fluorescence in each band of expected size, or by capillary electrophoresis, such as an Applied Biosystems® 3730 DNA analyzer or a QIAGEN® QIAxce® instrument. The concentration of desirable product in each multiplex reaction is used to calculate the relative amounts of each multiplex PCR reaction that are to be pooled together to result in equimolar amounts of each product added to the pool, taking the average size of each multiplex pool into consideration. Products are grouped and pooled by size to minimize amplification biases in downstream PCR amplifications.

The 192 multiplex reactions are combined into 24 larger pools as follows. Large Pool 1: multiplex pools 1-8; Large Pool 2: multiplex pools 9-16; Large Pool 3: multiplex pools 17-24; Large Pool 4: multiplex pools 25-32; Large Pool 5: multiplex pools 33-40; Large Pool 6: multiplex pools 41-48; Large Pool 7: multiplex pools 49-56; Large Pool 8: multiplex pools 57-64; Large Pool 9: multiplex pools 65-72; Large Pool 10: multiplex pools 73-80; Large Pool 11: multiplex pools 81-88; Large Pool 12: multiplex pools 89-96; Large Pool 13: multiplex pools 97-104; Large Pool 14: multiplex pools 105-112; Large Pool 15: multiplex pools 113-120; Large Pool 16: multiplex pools 121-128; Large Pool 17: multiplex pools 129-136; Large Pool 18: multiplex pools 137-144; Large Pool 19: multiplex pools 145-152; Large Pool 20: multiplex pools 153-160; Large Pool 21: multiplex pools 161-168; Large Pool 22: multiplex pools 169-176; Large Pool 23: multiplex pools 177-184; and Large Pool 24: multiplex pools 185-192. The resulting average ORF sizes (with and without added primer sequences) of each Large Pool is calculated based on the sizes of its component ORFs.

Once pooling has been completed, an amount of each ORF Large Pool corresponding to 10 µg of total desirable product are purified using a silica resin column or plate such as the Macherey Nagel NucleoSpin® 96 PCR cleanup kit, following the manufacturer's recommendations After elution of the purified PCR product, each sample is mixed thoroughly and its concentration determined spectrophotometrically.

To eliminate unwanted size products and primer dimers from the 48 Large Pools, 2 µg of each pool is electrophoresed on a 1% agarose gel and stained with ethidium bromide, the bands visualized under UV or blue light, and gel fragments corresponding to the correct size of each larger pool are excised from the gel. The gel fragments are weighed and DNA is purified from them using silica resin gel purification methods such as the Macherey Nagel NucleoSpin® Gel and PCR clean-up kit, following the manufacturer's recommendations. When the purification is complete, the concentrations of all samples are determined spectrophotometrically, and the concentration of each purified $2^{nd}$ stage Large Pool amplification product is adjusted to 10 ng/µL for $3^{rd}$ Stage Amplification.

$3^{rd}$ Stage Amplification:

The $3^{rd}$ stage amplification adds the final sequences to each PCR product to allow efficient assembly by end homology and to increase the amount of each Large Pool. The primers used in $3^{rd}$ stage amplifications are single primers with homology to the conserved portions of the $1^{st}$ and $2^{nd}$ stage amplification primers. The $3^{rd}$ stage primers are prepared as pairwise mixes, each containing equimolar amounts of the two primers and containing a total primer concentration of 20 µM.

The $3^{rd}$ stage PCR reaction mix is set up in 50 µl total volume and is mixed from the following components: 10 µl 5× Phusion® HF Buffer, 1 µl 10 mM dNTPs, 22 µl deionized $H_2O$, 10 µl gel-purified, pooled $2^{nd}$ stage reaction product (10 ng/µl), 6 µl $3^{rd}$ stage primer mix (20 µM) and 1 µl Phusion® Hot Start II thermostable polymerase (2 units/µl). The PCR cycling conditions are as follows: initial denaturation at 98° C. for 45 sec, 25 cycles consisting of two steps each (98° C. for 20 seconds and 72° C. for 3 minutes), a final extension step at 72° C. for 3 minutes and a soak at 4° C. until removal from the thermal cycler.

After the $3^{rd}$ stage amplification is complete, the samples are mixed thoroughly, centrifuged, and purified using a silica resin purification, such as the Macherey Nagel NucleoSpint 96 PCR clean-up kit, following the manufacturer's recommendations. After elution, each sample is mixed thoroughly and its concentration is determined spectrophotometrically.

For more efficient downstream processing, the 24 Large Pools are then consolidated into 5 "Superpools", by combining the 4 smallest Large Pools into one Superpool and combining successive sets of 5 Large Pools to form additional Superpools. The relative amounts of each Large Pool added to each Superpool is calculated, by considering the final concentrations of each large pool after $3^{rd}$ stage amplification and purification, and the final average size of each Large Pool (including sequences added by primers), with the goal of adding equimolar amounts of each Large Pool to each Superpool.

As in previous steps in this example, Superpools are prepared based on ORF size, with similarly sized ORF Larger Pools grouped into the same Superpool. To minimize cloning biases based on insert size, size fractions are cloned separately into the expression vectors, by combining each size pool of the 5' ORFs with each size pool of the 3' ORFs pairwise, in each case together with the cloning vector.

Randomized in Frame Fusion Polynucleotide Library Construction

After amplification, the relative concentrations of the ORFs are normalized for molar concentrations of DNA molecules (as opposed to mass concentrations). Specific ORFs, including ORFs from cloned polynucleotides or ORFs from other organisms that are added to an ORF collection generated by individual or pooled PCR amplification as described above, can be added to the ORF collection in varying amounts. For example, specific ORFs are added in molar amounts corresponding to the concentrations of other ORFs, or in lower or higher amounts that change their representation within the final randomized in-frame fusion polynucleotide library. For example, if a polynucleotide encoding a specific protein that confers stress tolerance is suspected to have a particularly high chance of conferring stress tolerance in *S. elongatus*, it is possible to over-represent this sequence in the ORF collection to ensure that most or all randomized in-frame fusion polynucleotide combinations are tested along with this prioritized sequence.

Randomized in Frame Fusion Polynucleotide Library Construction

After amplification and pooling into Superpools, the relative concentrations of the ORFs are normalized for molar concentrations of DNA molecules (as opposed to mass concentrations). Specific ORFs, including ORFs from cloned polynucleotides or ORFs from other organisms that are added to an ORF collection generated by individual or pooled PCR amplification as described above, can be added to the ORF collection in varying amounts. For example, specific ORFs are added in molar amounts corresponding to the concentrations of other ORFs, or in lower or higher amounts that change their representation within the final randomized in-frame fusion polynucleotide library. For example, if a polynucleotide encoding a specific protein that confers stress tolerance is suspected to have a particularly high chance of conferring stress tolerance in *E. coli*, it is possible to over-represent this sequence in the ORF collection to ensure that most or all randomized in-frame fusion polynucleotide combinations are tested along with this prioritized sequence.

One-step assembly of two ORFs into a pUC19 expression vector molecule is directed by conserved/homologous sequences that are located at the 5' and 3' ends of each fragment and that specify the structure of the circular, assembled product, shown in FIG. 3. Any one of a large number of methods can be used to accomplish this homology-dependent assembly, all of which are derived from cloning methods that are based on the annealing of homologous, single-stranded DNA ends, such as linker tailing methods (Lathe 1984) or methods dependent on complementary homopolymeric single-stranded tails at the ends of DNA molecules (Lobban 1973). In addition, modern homology-dependent cloning techniques are conceptually related to the ligation-independent cloning methods described in the early 1990s (Aslanidis 1990, Aslanidis 1994). Such homology-dependent cloning methods include but are not limited to: In-Fusion cloning (Zhu 2007, Irwin 2012), Sequence and Ligation-Independent Cloning (SLIC, Li 2007, Li 2012), FastCloning (Li 2011), Circular Polymerase Extension Cloning (Quan 2009, Quan 2011), the Gibson assembly method (Gibson 2009, Gibson 2010), Quick and Clean Cloning (Thieme 2011), and others (Vroom 2008).

Library assembly is performed in vitro with each combination of the five 5' and the five 3' ORF superpools, for a total of 25 assembly reactions. In each reaction, 150 fmol of the 5'ORF superpool DNA and 150 fmol of the 3'ORF superpool DNA (molar concentrations based on average size) are combined with 75 fmol of the PCR-amplified single fragment pUC19 vector DNA (SEQ ID 25126). The volume of the DNA mixture is adjusted to 10 µl, to which is added 10 µl of assembly mix (200 mM Tris pH 8.0, 20 mM $MgCl_2$, 0.4 mM each of dATP, dCTP, dGTP and dTTP, 20 mM dithiothreitol, 2 mM nicotinamide adenine dinucleotide, 0.02 units/µl T5 exonuclease, 0.05 units/µl Phusion® thermostable DNA polymerase, 0.4 units/µl Taq ligase). The reaction is mixed gently and incubated at 50° C. for 1-2 hours. The reaction is then kept on ice or frozen before use for *E. coli* transformations.

This in vitro assembly procedure can be performed as described, or with other enzymes with exonuclease activity that may be suitable for this procedure, such as T4 DNA polymerase, Exonuclease III, lambda exonuclease, T5 exonuclease or T7 exonuclease. Exonucleases with 5' to 3' directionality of their activity (i.e. T4 polymerase, lambda exonuclease, T5 exonuclease or T7 exonuclease) are preferred as they result in higher numbers of base pairs of annealed sequence between the two nicks at each cloning junction, thus stabilizing the desired product. The procedure can be performed without the addition of Taq DNA ligase, with satisfactory results. The reaction may also be supplemented with polyethylene glycol (molecular weight 4000-10000) at a final concentration of 5-10% to promote annealing of single-stranded DNA ends. However, given sufficiently high DNA concentrations as noted above, PEG is not necessary.

The assembly reactions are transformed into *E. coli* by electroporation by mixing 1 µl of the assembly reaction with 25 µl electrocompetent DH10B cells (Life Technologies Corporation) or EC100 cells (Epicentre Technologies) on ice. The cell/DNA mixture is then transferred into a 1 mm gap width electroporation cuvette and electroporated at 1.5 kV using a Bio-Rad Micropulser electroporator. The cells are suspended in 1 ml LB broth, cultured in a 10 ml culture tube for 1 hour at ° C. shaking at 250 rpm, and plated on LB agar containing 50-100 µg/µl carbenicillin. Transformation efficiencies can be improved by desalting the assembly reaction, either by DNA precipitation with ethanol, or by microdialysis, or by centrifugation through a Bio-Rad Micro Bio-Spin P6 gel column following the manufacturer's recommendation.

Library Transformation and Screening

The *S. elongatus* strains PCC7942 or PCC7002, which are used industrially as well as for research purposes (Ruffing 2011) are used for all transformations and screens.

Following assembly, the different libraries are either be used directly to generate *S. elongatus* transformants or are first amplified by transformation into *E. coli*.

The total possible number of sequence combinations resulting from random pairwise assembly of 2925 ORFs equals the square of this number=8.6 million. Typically, the goal of a screening project is to screen through 3× as many clones as the library complexity to have a >90% chance that each combination is represented. In this example, this would correspond to roughly 26 million transformants, which is possible in *S. elongatus* due to high transformation efficiencies that have been achieved in various laboratory strains. Generating 10 million *S. elongatus* transformants corresponds to performing roughly 1000 transformations using cells grown in 10 liters of culture medium.

Because plasmid assembly reactions using homology-dependent cloning methods can be highly efficient (Li 2007, Quan 2009, Gibson 2010, Li 2011, Quan 2011, Thieme 2011, Li 2012), resulting in a high percentage of the input DNA assembled into the correct product, S. elongatus can be transformed directly with the FG pool DNA. Assuming a S. elongatus transformation rate of 1E6 transformants per μg of DNA, this requires >10 μg of assembled FG pool DNA, which is an attainable number, considering that each assembly reaction contains a total of about 0.5 μg of DNA. Pilot S. elongatus transformation experiments are used to measure the number of transformants that can be generated from FG pool DNA, and whether these transformants contain integrated sequences of the correct structure.

If the observed S. elongatus transformation efficiency is limiting for generating a sufficient number of transformants directly from FG pool DNA, the FG pools can first be amplified in E. coli. A single 20 μl homology-mediated assembly reaction can yield roughly 2 million E. coli transformants, which can be amplified either in liquid gel medium (Elsaesser 2004) or by a combination of liquid growth and amplification with phi29 polymerase (Fullwood 2008). The plasmid amplification is performed separately for each of the 25 assembly pools, maintaining proportionality of the sequence combinations represented in each pool.

Transformation is achieved using the following procedure (Clerico 2007). S. elongatus cells are grown in 100 mL of liquid BG-11M to an OD750 of 0.7. 15 mL of the cyanobacterial cell suspension is harvested by centrifugation for 10 min at 6000 g. The cell pellet is resuspended in 10 mL of 10 mM NaCl and pelleted again by centrifugation for 10 min at 6000 g. The cell pellet is resuspended in 0.3 mL of BG-11M and transfer to a microcentrifuge tube. To each aliquot of 0.3 mL of cells, between 50 ng and 2 μg of DNA are added in a volume of 1-20 μL. The tubes are wrapped in aluminum foil to shield the cells from light and incubated overnight at 30° C. with gentle agitation. The entire 0.3-mL cell suspension is plated on a BG-11M plate containing the appropriate antibiotic or selective agent. The plates are incubated at 30° C. in constant light for approximately 5 days until single colonies appear.

Bacterial conjugation between E. coli and S. elongatus can also be used as an efficient way to deliver the library of fusion protein genes into S. elongatus (Tsinoremas 1994, Elhai 1994).

Isolated colonies can be re-streaked or grown in liquid culture in the presence of the antibiotic to continue selecting for the insertion. The transformed cells can be grown in the presence of inducer to activate expression of the fusion proteins (i.e. in the presence of IPTG when using the $P_{trc}$ promoter).

Screening for Rapid Growth/High-Biomass Phenotypes:

The pooled libraries containing fused genes are transformed into the PCC7942 laboratory strains of S. elongatus (Ruffing 2011) and then grown under conditions that select for presence of the plasmids and induce expression of the fusion proteins. All cultures are grown under carefully controlled, constant conditions in lighted racks and lighted orbital platform shakers to maintain uniformity in the selections.

Two different approaches are used to select or screen for transformants with higher growth rates and/or higher rates or biomass accumulation. One of these involves screening transformation plates for larger-sized colonies, while the other uses FACS sorting to isolate cyanobacterial microcolonies encapsulated and grown in alginate beads.

Larger colonies: Because screens on solid media allow visualization of individual clones or transformants, they are particularly useful for identifying transformants expressing genes contributing to rapid growth which are clearly visible as larger colonies, which can easily be picked out of large numbers of colonies, even at high plating densities. A difference as little as a few percent in doubling time can lead to a measurable difference in colony size. For example, a 6 day=144 hour growth period for a strain with an average doubling time of 6 hours=360 minutes would allow 24 doublings, while a strain with a 5% faster average doubling time of 342 minutes would double 25.3 times, leading to a 2.5-fold difference in cell number which is clearly reflected in colony size. Such screens have been used by others for isolation of genes contributing to ethanol tolerance in yeast (Hong 2010).

When screening for larger colonies, it is possible for false positives will arise in which the colony size is altered for reasons other than an increased rate of cell division or an increase in average cell size. Examples of such false positive are altered colony morphologies that result in flatter colonies, or colonies containing cells with higher mobility that tend to spread out from the edges of the colony. To rapidly eliminate these false positives, each candidate colony is lifted or scraped from the screening plate with a wire or plastic loop and suspended in a small amount of liquid medium. Half of the cell suspension is counted with a flow cytometer to determine the cell number and light scattering properties of the cell that are indicative of cell size. Only colonies with cell numbers that are 2 standard deviations above the average cell number found in 10 control colonies, or colonies containing cells with a proportionally similar increase in cell size, are retained for further characterization and validations.*

Encapsulation in gel microbeads: Encapsulation in alginate or agarose gel microbeads or microdrops has been successfully used for isolation of microbes capable of growth in a variety of environmental conditions, for culturing microbes that are unable to grow in high nutrient concentrations, or for performing growth assays of microbial strains or mixtures of microbes. Individual microbes encapsulated within a gel microbead form microcolonies within the bead as they grow and can be separated by fluorescent activated cell sorting based on the side scattering properties of the microbeads which reflect the size of the microcolonies within them.

Cyanobacterial transformants are removed from plates by wetting the plate with liquid medium and using the spreading action of 4-5 mm glass beads to separate colonies from the agar matrix. The suspended transformed cells are pooled corresponding to the sub-library that was used to produce them, and parts of each pool will be cryopreserved. Individual cyanobacterial cells are encapsulated in gel microdrops using published protocols and encapsulation materials and equipment sold by One Cell Systems Inc. The microdrop composition is adjusted to allow uniform growth of S. elongatus cells within them at normal rates of cell division.

The cells are grown at a density of $10^7$ microdrops per 50 ml in lighted bioreactors or growth flasks with constant shaking. To reduce the probability of multiple cells encapsulated within the same microdrop, the cell density is adjusted so that approximately 10% of microdrops contain a cell, requiring approximately $3 \times 10^8$ microdrops (in 1.5 L total volume of medium) to represent the entire library of $10^7$ transformants at >90% confidence of representation.

After several days' growth, the gel microbeads are collected by centrifugation and sorted by fluorescence activated cell sorting. Gel microdroplets containing microcolonies that are 2 standard deviations above the mean in side scattering are isolated, returned to liquid culture and grown for an additional several days to allow the cyanobacterial cells to overgrow the microdroplets and burst out of them. DNA is isolated from such cultures and used for plasmid rescue in *E. coli* (Dolganov 1993). Rescued plasmid are purified as populations of molecules and re-introduced into *S. elongatus* and the encapsulation, growth and sorting process will be repeated.

Characterization and Validation of Active Fusion Genes for Biomass and Growth Rate Colonies or populations of cells with phenotypes of interest arising on plates or in microdrop cultures are picked, expanded and used for plasmid rescue in *E. coli* (Dolganov 1993). Four *E. coli* colonies will be picked for each *S. elongatus* transformant, or 200 *E. coli* colonies are picked from each population of microdroplets. The DNA is isolated and checked by restriction digestion. The plasmid DNA is then be re-introduced into *S. elongatus* for phenotype confirmation.

For simplicity, all plasmids isolated in this fashion are validated using a standard growth rate and biomass assay conducted in 96-well format. Cells from each *S. elongatus* transformant to be verified are counted using an automated flow cytometer, and diluted to the same, standard cell density. 100 µl aliquots of each cell culture are added to a well in a 96-well plate which is covered and incubated with mild shaking under lights under conditions minimizing evaporation. After several days of growth, a small aliquot of each culture is analyzed by flow cytometry to determine the cell density and average cell size. The remainder of each culture is washed with water to remove salts, the cell pellet is dried and weighed to determine dry weight. The results are tabulated to allow selection of the most promising fusion gene constructs with the greatest effect on cell number, cell size of dry weight of the resulting culture.

Screening for Alcohol-Resistance

Four different approaches are used to select or screen for butanol- or ethanol-tolerant transformants. Two of these involve survival selections, using lethal concentrations of butanol to isolate cells with the ability to survive the alcohol. The other two approaches aim to isolate cells with improved growth properties in the presence of sub-lethal concentrations of butanol or ethanol. The selections/screens either involve growth and selection on solid medium or combine growth in liquid medium with screens on solid medium. The selection and screening approaches are summarized for butanol as an example in Table 6, with the concentration ranges of butanol estimated based on published information for isobutanol and n-butanol (Atsumi 2009, Kämäräinen 2012). The column 'incubation time' refers to the amount of time the transformants are cultured time in the presence of butanol. The same methods used to isolate alcohol-resistant or alcohol-tolerant cells can also be used to select and screen for tolerance to other toxic compounds such as butyraldehyde, or to other conditions of abiotic stress such as high salt and high temperature.

Alternatively, transformants are cultured in bulk in liquid culture under conditions selecting for various types of growth and resistance properties of the cells. The four selection schemes are preceded by careful titration, under the exact plating or culturing conditions and cell densities to be used later with bulk *S. elongatus* transformants, to arrive at the optimal butanol concentration for each selection. All cultures are grown under carefully controlled, constant conditions to maintain uniformity in the selections.

TABLE 6

Selections and screens for butanol-tolerant *S. elongatus* transformants

| Selection type | Solid or liquid medium | Butanol concentration | Incubation time | Selection based on: |
|---|---|---|---|---|
| Survival | solid | Lethal: 1.5-2.5% butanol | 10-20 days | Colonies growing on plates |
| Growth tolerance | solid | Sub-lethal: 1-2% butanol | 10-20 days | Colony size |
| Survival | liquid | Lethal: 1.5-2.5% butanol | 24-48 hours | Surviving cells |
| Growth tolerance | Liquid/solid | Sub-lethal: 1-2% butanol | 48-96 hours (liquid) 10-20 days (solid) | Colony size |

For selections and screens on solid media, following transformation of the randomized fusion polypeptide library, transformants are pre-cultured in liquid media lacking antibiotics for 6 hours at 30° C. under light. Antibiotics and IPTG are then added to the liquid culture to select for presence of the plasmid and induce expression of the randomized in-frame fusion polynucleotides, and the transformants are cultured for an additional hour. The culture is then diluted appropriately to allow for manageable numbers of transformants per plate (approximately 2000-20000 colonies per 10 cm plate depending on the trait selected or screened for). The culture is plated on solid medium whose composition depending on the trait being selected for, for example BG11M agar containing butanol see Table 6. The plates are incubated at 30° C. for several days and colonies are selected at that time for colony picking, plasmid isolations, phenotype validation and characterization of active randomized in-frame fusion polynucleotides (see below). Colony selections are either made based on colony size (reflective of growth rate and growth yield, used to identify polynucleotides affecting growth rate, low temperature growth and growth yield traits) or on positive selection i.e. in the cases where the majority of transformants fail to grow on the plate and only those that grow contain a randomized in-frame fusion polynucleotide of interest (used to identify randomized fusion polynucleotides affecting tolerance of high temperatures, salt or organic solvents).

Because screens on solid media allow visualization of individual clones or transformants, they are particularly useful for identifying transformants expressing randomized in-frame fusion polynucleotides contributing to rapid growth which are clearly visible as larger colonies. A difference as little as a few percent in doubling time can lead to a measurable difference in colony size. For example, a 6 day=144 hour growth period for a strain with an average doubling time of 6 hours=360 minutes would allow 24 doublings, while a strain with a 5% faster average doubling time of 342 minutes would double 25.3 times, leading to a 2.5-fold difference in cell number which is clearly reflected in colony size. Such screens can be performed with any media conditions, for example it is possible to screen for growth rate in the presence of sub-lethal amounts of inhibiting agents such as salt, ethanol or butanol, or in sub-lethal high or low temperatures. Similar screens have been used by others for isolation of genes contributing to ethanol tolerance (Hong 2010).

Selections and screens in liquid media are generally performed as bulk selections. Following transformation of the randomized in-frame fusion polynucleotide library into competent cells, transformants are pre-cultured in liquid media lacking antibiotics for 6 hours at 30° C. under light. Antibiotics and IPTG are then added to the liquid culture to select for presence of the plasmid and induce expression of the randomized in-frame fusion polynucleotides, and the transformants are cultured for an additional hour. The culture is then diluted 2-10× in fresh medium containing antibiotics and IPTG and containing selective agents such as butanol as listed in Table 6. The culture is allowed to grow at 30° C. or for an additional 24 hours to several days, depending on the type of selection imposed on the cells. At that time, the cells are harvested by centrifugation, DNA containing the randomized in-frame fusion polynucleotide is extracted using chromosomal DNA isolation procedures (Clerico 2007), the plasmids are cloned in E. coli, prepped in bulk, and the transformation and selection of S. elongatus is repeated. Two or more cycles of batch selection can be performed in this manner before a transformation is plated on solid media allowing selection of individual transformants, followed by colony picking, plasmid isolations, phenotype validation and characterization of active fusion polynucleotides (see below).

Selections in liquid can be done either as survival selections or as selections for rapidly-dividing cells. Survival selections are performed in the presence of a lethal concentration of a selective agent (i.e. salt, ethanol or butanol, in this example) or at a lethal high or low temperatures, and for a specific period of time (generally 12 hours or longer). Following the selective period, the selective culture is diluted in fresh, non-selective medium, or the temperature is returned to 37° C. to allow any surviving cells to resume normal growth. This culture containing surviving cells is grown up, chromosomal DNA is extracted, the plasmids cloned in E. coli and the batch selection repeated if necessary, as described above.

Alternatively, a selection in liquid culture is performed to select for rapid growth in the presence of a sub-lethal concentration of a selective agent (i.e. salt, ethanol or butanol, in this example) or at a sub-lethal high or low temperatures. In this case, a liquid culture of transformants maintained under selective conditions is allowed to grow to mid-log phase only (generally 2-5 days of growth, depending on the severity of selective conditions). At that point, the majority of cells in the culture are expected to be alive, but the culture is enriched for cells capable of normal, rapid growth under the selective conditions. The cells are pelleted by centrifugation, chromosomal DNA is extracted, the plasmids cloned in E. coli and the batch selection repeated if necessary. Alternatively, the cells harvested from the sub-lethal growth conditions can be plated on solid medium containing lethal or sub-lethal concentrations of butanol or another selective agent to allow visual selection of colonies capable of growth or with accelerated of growth in the presence of selective agent.

Characterization of Active Fusion Genes for Alcohol Tolerance

Colonies with butanol-resistant phenotypes arising on selective plates are picked, expanded and used for plasmid rescue in E. coli (Dolganov 1993). Four E. coli colonies are picked for each S. elongatus transformant, the DNA isolated and checked by restriction digestion. The plasmid DNA is then re-introduced into S. elongatus for phenotype confirmation.

For simplicity, all plasmids are checked using two standard butanol-tolerance assays that are conducted in 96-well formats. The two assays use lethal and sublethal concentrations of butanol, respectively, in liquid culture. After a period of culture under lethal conditions, or several passages of growth under sublethal conditions, the cultures are serially diluted and spotted onto solid media to assess the density of surviving cells. These assays allow rapid and uniform testing of all isolated plasmids with the necessary controls, and allow rapid validation of fusion genes conferring survival or growth advantages in the presence of butanol.

Re-transformations of active plasmids are also tested more broadly for growth or tolerance phenotypes. For growth rate and growth yield traits, this involves plating the transformants at low cell density and observing the sizes of the resulting colonies compared to a control transformant, or alternatively comparing doubling times or cell pellet size in liquid culture, with or without selective conditions, to the rate of growth of a control strain. For resistance phenotypes (temperature, ethanol and butanol), the re-screen involves replica plating of transformants (i.e. replicated from a 96-well plate onto a plate using a 96-pin tool) on to solid media and growth under selective conditions to compare the extent of growth of each transformation to controls. Alternatively, the transformations are exposed to selective conditions in liquid culture, followed by replicating by pin-tool on to non-selective solid media to assess the degree of cell survival in each culture, reflected in the number of surviving colonies.

A specific candidate randomized in-frame fusion polynucleotide can be tested either for conferral of the phenotype that it was originally selected for, or for another phenotype. Various phenotypes related to cell growth and stress tolerance can cross-react. For example, a randomized in-frame fusion polynucleotide selected for conferral of butanol tolerance can also confer ethanol tolerance, temperature tolerance, salt tolerance, etc. By extensively cross-testing randomized in-frame fusion polynucleotides under various conditions it is possible to find randomized in-frame fusion polynucleotides with a broad ability to advance cell growth under various conditions of abiotic stress.

Fusion gene expression constructs conferring the most dramatic or broad phenotypes are sequenced to identify the active genes. The results are tabulated and the best fusion genes chosen for future work. Sequences identified repeatedly within distinct fusion genes can be used in future screens as part of ORF collections. ORF collections containing genes already known to confer a desirable phenotype may be smaller than the whole-genome ORF collections described in this proposal, with many resulting advantages including smaller library size, less expensive and more rapid screens, and applicability to organisms with more complex genomes and lower transformation efficiencies, including eukaryotic algae and plants.

There are many advantages to limiting the size of an ORF collection, the most important of which is the smaller number of pairwise combinations that are represented in the resulting library of randomized in-frame fusion polynucleotides. Lower-complexity libraries can be screened faster and less expensively than more complex libraries, and are amenable to screening for more complex phenotypes than those listed above that involve visual screens and positive selections. Lower-complexity libraries are also amenable to testing in organisms with lower transformation efficiencies where it may not be realistic or reasonably possible to screen libraries containing tens of millions of sequence combinations (resulting from ORF collections numbering in the thousands), but which may be suitable for screening libraries containing hundreds of thousands of sequence combinations (resulting from ORF collections numbering in the hundreds).

Evaluation of Results and Conclusions

When implementing this approach to constructing and testing randomized in-frame fusion polynucleotides, it is possible to compare the results to those obtained from simple overexpression of the same gene collection used to construct the randomized in-frame fusion polynucleotides libraries. The data generated in the course of such experiments allows comparison of the number of active genes isolated with each approach, the frequency of an active gene (i.e. per 1000 genes screened) and the quality of the phenotypes produced. These three metrics are critical in determining whether the randomized in-frame fusion polynucleotides technology holds promise for engineering useful phenotypes in cyanobacteria.

REFERENCES

Alper H, Moxley J, Nevoigt E, Fink G R, Stephanopoulos G (2006). Engineering yeast transcription machinery for improved ethanol tolerance and production. Science 314: 1565-1568.

Andersson C R, Tsinoremas N F, Shelton J, Lebedeva N V, Yarrow J, Min H, Golden S S (2000). Application of bioluminescence to the study of circadian rhythms in cyanobacteria. Methods Enzymol. 305:527-542.

Arai R, Ueda H, Kitayama A, Kamiya N, Nagamune T (2001). Design of the linkers which effectively separate domains of a bifunctional fusion protein. Protein Engineering 14 (8): 529-532

Ashby M K, Houmard J (2006). Cyanobacterial two-component proteins: structure, diversity, distribution, and evolution. Microbiol Mol Biol Rev. 70(2):472-509.

Aslanidis C, DeJong P J (1990). Ligation-independent cloning of PCR products (LI-PCR). Nucl Acids Res 18 (20): 6069-6074

Aslanidis C, de Jong P J, Schmitz G. (1994). Minimal length requirement of the single-stranded tails for ligation-independent cloning (LIC) of PCR products. PCR Methods Appl. 4(3): 172-177.

Atsumi S, Wu T-Y, Machado I M P, Huang W-C, Chen P-Y, Pellegrini M, Liao J C (2010). Evolution, genomic analysis, and reconstruction of isobutanol tolerance in Escherichia coli. Mol Syst Biol 6:449.

Atsumi S, Higashide W, Liao J C. (2009). Direct photosynthetic recycling of carbon dioxide to isobutyraldehyde. Nat Biotechnol. 27(12):1177-1180.

Babushok D V, Ostertag E M, Kazazian H H Jr (2007). Current topics in genome evolution: molecular mechanisms of new gene formation. Cell Mol Life Sci. 64(5): 542-54.

Baer S, Blaschek H, Smith T (1987). Effect of butanol challenge and temperature on lipid composition and membrane fluidity of butanol tolerant Clostridium acetobutylicum. Appl Environ Microbiol 53:2854-2861.

Beekwilder J, Rakonjac J, Jongsma M, Bosch D (1999). A phagemid vector using the E. coli phage shock promoter facilitates phage display of toxic proteins. Gene 228(1-2): 23-31.

Belyaeva T, Griffiths L, Minchin S, Cole J, Busby S (1993). The Escherichia coli cysG promoter belongs to the 'extended-10' class of bacterial promoters. Biochem. J. (1993) 296 (Pt 3): 851-857

Brachmann C B, Davies A, Cost G J, Caputo E, Li J, Hieter P, Boeke J D (1998). Designer deletion strains derived from Saccharomyces cerevisiae S288C: a useful set of strains and plasmids for PCR-mediated gene disruption and other applications. Yeast 14(2):115-132.

Brissette J L, Russel M, Weiner L, Model P (1990). Phage shock protein, a stress protein of Escherichia coli. Proc Natl Acad Sci USA. 87(3): 862-866.

Brissette J L, Weiner L, Ripmaster T L, Model P (1991). Characterization and sequence of the Escherichia coli stress-induced psp operon. J Mol Biol. 220(1): 35-48.

Bustos S A, Golden S S (1991). Expression of the psbDII gene in Synechococcus sp. strain PCC 7942 requires sequences downstream of the transcription start site. J Bacteriol. 173(23):7525-7533.

Bustos S A, Golden S S (1992). Light-regulated expression of the psbD gene family in Synechococcus sp. strain PCC 7942: evidence for the role of duplicated psbD genes in cyanobacteria. Mol Gen Genet. 232(2):221-230.

Chenna R, Sugawara H, Koike T, Lopez R, Gibson T J, Higgins D G, Thompson J D (2003). Multiple sequence alignment with the Clustal series of programs. Nucleic Acids Res. 31(13):3497-3500.

Clerico E M, Ditty J L, Golden S S (2007). Specialized techniques for site-directed mutagenesis in cyanobacteria. Methods Mol Biol. 362:155-171.

Dahl F, Gullberg M, Stenberg J, Landegren U, Nilsson M (2005). Multiplex amplification enabled by selective circularization of large sets of genomic DNA fragments. Nucleic Acids Res. 33(8): e71.

De Mey M, Maertens J, Lequeux G J, Soetaert W K, Vandamme E J (2007). Construction and model-based analysis of a promoter library for E. coli: an indispensable tool for metabolic engineering BMC Biotechnol. 7:34

Degryse E, Dumas B, Dietrich M, Laruelle L, Achstetter T (1995). In vivo cloning by homologous recombination in yeast using a two-plasmid-based system. Yeast 11(7):629-640.

Deng M D, Coleman J R (1999). Ethanol synthesis by genetic engineering in cyanobacteria. Appl Environ Microbiol. 65(2):523-528.

Dexter J, Fu P (2009). Metabolic engineering of cyanobacteria for ethanol production. Energy Environ. Sci. 2(8): 857-864.

Ding J, Huang X, Zhang L, Zhao N, Yang D, Zhang K (2009). Tolerance and stress response to ethanol in the yeast Saccharomyces cerevisiae. Appl Microbiol Biotechnol. 85(2):253-263.

Dismukes G C, Carrieri D, Bennette N, Ananyev G M, Posewitz M C (2008). Aquatic phototrophs: efficient alternatives to land-based crops for biofuels. Curr Opin Biotechnol. 19(3):235-240.

Dolganov N, Grossman A R (1993). Insertional inactivation of genes to isolate mutants of Synechococcus sp. strain PCC 7942: isolation of filamentous strains. J Bacteriol. 175(23):7644-7651.

Ducat D C, Way J C, Silver P A (2011). Engineering cyanobacteria to generate high-value products. Trends Biotechnol. 29(2):95-103.

Ducat D C, Avelar-Rivas J A, Way J C, Silver P A (2012). Rerouting carbon flux to enhance photosynthetic productivity. Appl Environ Microbiol. 78(8):2660-2668.

Dunlop M J (2011). Engineering microbes for tolerance to next-generation biofuels. Biotechnol Biofuels 4:32

Dunlop M J, Dossani Z Y, Szmidt H L, Chu H C, Lee T S, Keasling J D, Hadi M, Mukhopadhyay A (2011a). Engineering microbial biofuel tolerance and export using efflux pumps. Mol Syst Biol 7:487.

Eisenbeis S, Hocker B (2010). Evolutionary mechanism as a template for protein engineering. J Pept Sci. 16(10): 538-544.

Eldridge B, Cooley R N, Odegrip R, McGregor D P, Fitzgerald K J, Ullman C G (2009). An in vitro selection strategy for conferring protease resistance to ligand binding peptides. Protein Eng Des Sel. 22(11):691-8.

Elhai J (1994). Genetic techniques appropriate for the biotechnological exploitation of cyanobacteria. J. Appl. Phycol. 6(2):177-186.

Elsaesser R, Paysan J. (2004). Liquid gel amplification of complex plasmid libraries. Biotechniques 37(2):200-202.

Elsharawy A, Warner J, Olson J, Forster M, Schilhabel M B, Link D, Rose-John S, Schreiber S, Rosenstiel P, Brayer J, Franke A (2012). Accurate variant detection across non-amplified and whole genome amplified DNA using targeted next generation sequencing. BMC Genomics 13(1): 500.

Flores E, Muro-Pastor A M, Meeks J C (2008). Gene transfer to cyanobacteria in the laboratory and in nature. In: Herrero A, Flores E, eds. The cyanobacteria: molecular biology, genomics and evolution. Norfolk, UK: Caister Academic Press. pp 45-57.

Fullwood M J, Tan J J, Ng P W, Chiu K P, Liu J, Wei C L, Ruan Y (2008). The use of multiple displacement amplification to amplify complex DNA libraries. Nucleic Acids Res. 36(5):e32.

Funk M, Niedenthal R, Mumberg D, Brinkmann K, Rönicke V, Henkel T (2002). Vector systems for heterologous expression of proteins in *Saccharomyces cerevisiae*. Methods Enzymol. 350:248-57.

Gao Z, Zhao H, Li Z, Tan X, Lu X (2012). Photosynthetic production of ethanol from carbon dioxide in genetically engineered cyanobacteria. Energy Environ. Sci. 5(12): 9857-9865.

Geerts D, Bovy A, de Vrieze G, Borrias M, Weisbeek P (1995). Inducible expression of heterologous genes targeted to a chromosomal platform in the *cyanobacterium Synechococcus* sp. PCC 7942. Microbiology 141(4):831-841.

Gibson D G, Young L, Chuang R Y, Venter J C, Hutchison C A 3rd, Smith H O (2009). Enzymatic assembly of DNA molecules up to several hundred kilobases. Nat Methods. 6(5):343-345

Gibson D G, Smith H O, Hutchison C A 3rd, Venter J C, Merryman C. (2010). Chemical synthesis of the mouse mitochondrial genome. Nat Methods. 7(11):901-903.

Gietz R D, Woods R A (2002). Transformation of yeast by lithium acetate/single-stranded carrier DNA/polyethylene glycol method. Methods Enzymol. 350:87-96.

Gietz R D, Woods R A (2006). Yeast transformation by the LiAc/SS Carrier DNA/PEG method. Methods Mol Biol. 313:107-120.

Gietz R D, Schiestl R H (2007). High-efficiency yeast transformation using the LiAc/SS carrier DNA/PEG method. Nat Protocols 2(1):31-34.

Gilbert W (1978). Why genes in pieces? Nature 271(5645): 501.

Golden S S, Brusslan J, Haselkorn R (1987). Genetic engineering of the cyanobacterial chromosome. Methods Enzymol. 153:215-231.

Hammer K, Mijakovic I, Jensen P R (2006). Synthetic promoter libraries—tuning of gene expression. Trends Biotechnol. 24 (2): 53-55

Haun R S, Serventi I M, Moss J (1992). Rapid, reliable ligation-independent cloning of PCR products using modified plasmid vectors. Biotechniques, 13(4): 515-518.

Heidorn T, Camsund D, Huang H H, Lindberg P, Oliveira P, Stensjo K, Lindblad P (2011). Synthetic biology in cyanobacteria engineering and analyzing novel functions. Methods Enzymol. 497:539-579.

Hong M E, Lee K S, Yu B J, Sung Y J, Park S M, Koo H M, Kweon D H, Park J C, Jin Y S (2010). Identification of gene targets eliciting improved alcohol tolerance in *Saccharomyces cerevisiae* through inverse metabolic engineering. J Biotechnol. 149(1-2):52-59.

Inaki K, Liu E T (2012). Structural mutations in cancer: mechanistic and functional insights. Trends Genet. 28(11):550-559.

Irwin C R, Farmer A, Willer D O, Evans D H (2012). In-fusion® cloning with vaccinia virus DNA polymerase. Methods Mol Biol. 890:23-35.

Ishiura M, Kutsuna S, Aoki S, Iwasaki H, Andersson C R, Tanabe A, Golden S S, Johnson C H, Kondo T (2000). Expression of a gene cluster kaiABC as a circadian feedback process in cyanobacteria. Science 281(5382): 1519-1523.

Jang Y S, Kim B, Shin J H, Choi Y J, Choi S, Song C W, Lee J, Park H G, Lee S Y (2012). Bio-based production of C2-C6 platform chemicals. Biotechnol Bioeng. 109(10): 2437-2459.

Jensen P R, Hammer K (1998a). Artificial promoters for metabolic optimization. Biotechnol. Bioengineering 58 (2-3): 191-195

Jensen, P R; Hammer, K (1998b). The sequence of spacers between the consensus sequences modulates the strength of prokaryotic promoters. Appl. Environ. Microbiol. 64 (1): 82-87.

Jia, Kaizhi; Zhang, Yanping; Li, Yin (2009). Systematic engineering of microorganisms to improve alcohol tolerance. Engineering in Life Sciences 10(5): 422-429

Jovanovic G, Weiner L, Model P (1996). Identification, nucleotide sequence, and characterization of PspF, the transcriptional activator of the *Escherichia coli* stress-induced psp operon. J. Bacteriol. 178 (7): 1936-1945

Kämäräinen J, Knoop H, Stanford N J, Guerrero F, Akhtar M K, Aro E M, Steuer R,

Jones P R (2012). Physiological tolerance and stoichiometric potential of cyanobacteria for hydrocarbon fuel production. J Biotechnol. 162(1):67-74.

Knoshaug E P, Zhang M (2008). Butanol tolerance in a selection of microorganisms. Appl Biochem Biotechnol. 153(1-3):13-20.

Kuijpers N G, Solis-Escalante D, Bosman L, van den Broek M, Pronk J T, Daran J M, Daran-Lapujade P (2013). A versatile, efficient strategy for assembly of multi-fragment expression vectors in Saccharomyces cerevisiae using 60 bp synthetic recombination sequences. Microb Cell Fact. 12:47.

Kondo T, Strayer C A, Kulkarni R D, Taylor W, Ishiura M, Golden S S, Johnson C H (1993). Circadian rhythms in prokaryotes: luciferase as a reporter of circadian gene expression in cyanobacteria. Proc Natl Acad Sci USA 90(12):5672-5676.

Kulkarni R D, Golden S S (1997). mRNA stability is regulated by a coding-region element and the unique 5' untranslated leader sequences of the three Synechococcus psbA transcripts. Mol Microbiol. 24(6):1131-1142.

Kutsuna S, Kondo T, Aoki S, Ishiura M (1998). A period-extender gene, pex, that extends the period of the circadian clock in the cyanobacterium Synechococcus sp. strain PCC 7942. J Bacteriol. 180(8):2167-2174.

Lan E I, Liao J C (2011). Metabolic engineering of cyanobacteria for 1-butanol production from carbon dioxide. Metab Eng. 13(4):353-63.

Lan E I, Liao J C (2012). ATP drives direct photosynthetic production of 1-butanol in cyanobacteria. Proc Natl Acad Sci USA. 109(16):6018-6023.

Lee J W, Na D, Park J M, Lee J, Choi S, Lee S Y (2012). Systems metabolic engineering of microorganisms for natural and non-natural chemicals. Nat Chem Biol. 8(6): 536-546.

Li M Z, Elledge S J. (2007). Harnessing homologous recombination in vitro to generate recombinant DNA via SLIC. Nat Methods. 4(3): 251-256.

Li C, Wen A, Shen B, Lu J, Huang Y, Chang Y. (2011). FastCloning: a highly simplified, purification-free, sequence- and ligation-independent PCR cloning method. BMC Biotechnol. 11:92.

Li M Z, Elledge S J. (2012). SLIC: a method for sequence- and ligation-independent cloning. Methods Mol Biol. 852:51-59.

Liang S T, Bipatnath M; Xu Y C, Chen S L, Dennis P, Ehrenberg M, Brehmer H (1999). Activities of constitutive promoters in Escherichia coli. J. Mol. Biol. 292 (1): 19-37

Lindberg P, Park S, Melis A (2010). Engineering a platform for photosynthetic isoprene production in cyanobacteria, using Synechocystis as the model organism. Metab Eng. 12(1):70-79.

Liu S, Qureshi N (2009). How microbes tolerate ethanol and butanol. New Biotechnol. 26(3-4):117-121.

Liu X, Sheng J, Curtiss R III (2011). Fatty acid production in genetically modified cyanobacteria. Proc Natl Acad Sci USA. 108(17):6899-6904.

Liu J, Chen L, Wang J, Qiao J, Zhang W (2012). Proteomic analysis reveals resistance mechanism against biofuel hexane in Synechocystis sp. PCC 6803. Biotechnol Biofuels. 5(1):68.

Lobban P E, Kaiser A D (1973). Enzymatic end-to end joining of DNA molecules. J Mol Biol. 78(3): 453-471.

Ma H, Kunes S, Schatz P J, Botstein D (1987). Plasmid construction by homologous recombination in yeast. Gene 58(2-3):201-216.

Machado I M, Atsumi S (2012). Cyanobacterial biofuel production. J Biotechnol. 162(1):50-56.

Marschalek R (2011). Mechanisms of leukemogenesis by MLL fusion proteins. Br J Haematol. 152(2):141-154.

Mascal M (2012). Chemicals from biobutanol: technologies and markets. Biofuels, Bioprod. Bioref. 6(4):483-493.

Melo J V (1996). *The diversity of BCR-ABL fusion proteins and their relationship to leukemia phenotype*. Blood 88(7):2375-2384.

Menart V, Jevševar S., Vilar M, Trobiš A, Pavko A (2003). Constitutive versus thermoinducible expression of heterologous proteins in Escherichia coli based on strong $P_R, P_L$ promoters from phage lambda. Biotechnology and Bioengineering 83 (2): 181-190.

Mitelman F, Johansson B, Mertens F (2004). Fusion genes and rearranged genes as a linear function of chromosome aberrations in cancer. Nat Genet. 36(4):331-334.

Mitelman F, Johansson B, Mertens F (2007). The impact of translocations and gene fusions on cancer causation. Nat Rev Cancer 7(4):233-245.

Model P, Jovanovic G, Dworkin J (1997). The Escherichia coli phage-shock-protein (psp) operon. Mol Microbiol. 24(2):255-61.

Mutsuda M, Michel K P, Zhang X, Montgomery B L, Golden S S (2003). Biochemical properties of CikA, an unusual phytochrome-like histidine protein kinase that resets the circadian clock in Synechococcus elongatus PCC 7942. J Biol Chem 278(21): 19102-19110

Myllykangas S, Natsoulis G, Bell J M, Ji H P (2011). Targeted sequencing library preparation by genomic DNA circularization. BMC Biotechnol. 11:122.

Natsoulis G, Bell J M, Xu H, Buenrostro J D, Ordonez H, Grimes S, Newburger D, Jensen M, Zahn J M, Zhang N, Ji H P (2011). A flexible approach for highly multiplexed candidate gene targeted resequencing. PLoS One 6(6):e21088.

Newburger D E, Natsoulis G, Grimes S, Bell J M, Davis R W, Batzoglou S, Ji H P (2012). The Human OligoGenome Resource: a database of oligonucleotide capture probes for resequencing target regions across the human genome. Nucleic Acids Res. 40(Database issue):D1137-1143.

Oliver J W, Machado I M, Yoneda H, Atsumi S (2013). Cyanobacterial conversion of carbon dioxide to 2,3-butanediol. Proc Natl Acad Sci USA. 110(4):1249-1254.

Quan J, Tian J (2009). Circular polymerase extension cloning of complex gene libraries and pathways. PLoS One. 4(7): e6441.

Quan J, Tian J (2011). Circular polymerase extension cloning for high-throughput cloning of complex and combinatorial DNA libraries. Nat Protoc. 6(2):242-251

Rabbitts T H (2009). Commonality but diversity in cancer gene fusions. Cell 137(3):391-395.

Raymond C K, Pownder T A, Sexson S L (1999). General method for plasmid construction using homologous recombination. Biotechniques 26(1):134-8, 140-1.

Raymond C K, Sims E H, Olson M V (2002). Linker-mediated recombinational subcloning of large DNA fragments using yeast. Genome Res. 12(1):190-197.

Robertson D E, Jacobson S A, Morgan F, Berry D, Church G M, Afeyan N B (2011). A new dawn for industrial photosynthesis. Photosynth Res. 107(3):269-277.

Ruffing A M. (2011). Engineered cyanobacteria: teaching an old bug new tricks. Bioeng Bugs. 2(3):136-149.

Sambrook, J., Fritsch, E. F., and Maniatis, T. (1989) Molecular Cloning: A Laboratory Manual, Second Ed., Cold Spring Harbor Laboratory Press, Plainview, N.Y.

Sawyers C L (1992). The bcr-abl gene in chronic myelogenous leukaemia. Cancer Surv. 15:37-51.

Shao Z, Zhao H, Zhao H (2009). DNA assembler, an in vivo genetic method for rapid construction of biochemical pathways. Nucleic Acids Res. 37(2):e16.

Shizuya H, Birren B, Kim U J, Mancino V, Slepak T, Tachiiri Y, Simon M (1992). Cloning and stable maintenance of 300-kilobase-pair fragments of human DNA in *Escherichia coli* using an F-factor-based vector. Proc Natl Acad Sci USA 89(18): 8794-8797.

Steen E J, Chan R, Prasad N, Myers S, Petzold C J, Redding A, Ouellet M, Keasling J D (2008). Metabolic engineering of *Saccharomyces cerevisiae* for the production of n-butanol. Microb Cell Fact. 2008 7:36.

Stemmer W P (1994). Rapid evolution of a protein in vitro by DNA shuffling. Nature 370(6488):389-391.

Stemmer W P (1994a). DNA shuffling by random fragmentation and reassembly: in vitro recombination for molecular evolution. Proc Natl Acad Sci USA 91(22):10747-10751.

Takahama K, Matsuoka M, Nagahama K, Ogawa T (2003). Construction and analysis of a recombinant *cyanobacterium* expressing a chromosomally inserted gene for an ethylene-forming enzyme at the psbAI locus. J Biosci Bioeng. 95(3):302-305.

Tan X, Yao L, Gao Q, Wang W, Qi F, Lu X. (2011). Photosynthesis driven conversion of carbon dioxide to fatty alcohols and hydrocarbons in cyanobacteria. Metab Eng. 13(2):169-176.

Tewhey R, Warner J B, Nakano M, Libby B, Medkova M, David P H, Kotsopoulos S K, Samuels M L, Hutchison J B, Larson J W, Topol E J, Weiner M P, Harismendy O, Olson J, Link D R, Frazer K A (2009). Microdroplet-based PCR enrichment for large-scale targeted sequencing. Nat Biotechnol. 27(11):1025-1031.

Thieme F, Engler C, Kandzia R, Marillonnet S (2011). Quick and clean cloning: a ligation-independent cloning strategy for selective cloning of specific PCR products from non-specific mixes. PLoS One 6(6): e20556

Tian X, Chen L, Wang J, Qiao J, Zhang W. (2013). Quantitative proteomics reveals dynamic responses of *Synechocystis* sp. PCC 6803 to next-generation biofuel butanol. J Proteomics 78:326-345.

Tomas C, Welker N, Papoutsakis E (2003). Overexpression of groESL in *Clostridium acetobutylicum* results in increased solvent production and tolerance, prolonged metabolism, and changes in the cell's transcriptional program. Appl Environ Microbiol 69:4951-4965.

Tsinoremas N F, Kutach A K, Strayer C A, Golden S S (1994). Efficient gene transfer in *Synechococcus* sp. strains PCC 7942 and PCC 6301 by interspecies conjugation and chromosomal recombination. J Bacteriol. 176 (21):6764-6768.

Vieira J, Messing J (1982). The pUC plasmids, an M13mp7-derived system for insertion mutagenesis and sequencing with synthetic universal primers. Gene 19(3):259-268.

Vioque A. (2007). Transformation of cyanobacteria. Adv Exp Med Biol. 616:12-22.

Vroom J A, Wang C L (2008). Modular construction of plasmids through ligation-free assembly of vector components with oligonucleotide linkers. Biotechniques 44(7): 924-926.

Wang R, Xue Y, Wu X, Song X, Peng J (2010). Enhancement of engineered trifunctional enzyme by optimizing linker peptides for degradation of agricultural by-products. Enzyme and Microb. Technol. 47 (5): 194-199

Wang B, Wang J, Zhang W, Meldrum D R (2012). Application of synthetic biology in cyanobacteria and algae. Front Microbiol. 3:344.

Ward A C (1990). Single-step purification of shuttle vectors from yeast for high frequency back-transformation into *E. coli*. Nucleic Acids Res. 8(17):5319.

Weiner L, Brissette J L, Model P (1991). Stress-induced expression of the *Escherichia coli* phage shock protein operon is dependent on 6-54 and modulated by positive and negative feedback mechanisms Genes Dev. 5(10): 1912-1923

Weiner L, Brissette J L, Ramani N, Model P. (1995). Analysis of the proteins and cis-acting elements regulating the stress-induced phage shock protein operon. Nucleic Acids Res. 23(11): 2030-2036.

Whitworth D E, Cock P J (2009). Evolution of prokaryotic two-component systems: insights from comparative genomics. Amino Acids 37(3):459-66.

Wingler L M, Cornish V W (2011). Reiterative Recombination for the in vivo assembly of libraries of multigene pathways. Proc Natl Acad Sci USA. 108(37):15135-15140.

Zhang W, Fisher J F, Mobashery S. (2009). The bifunctional enzymes of antibiotic resistance. Curr Opin Microbiol. 12(5):505-511.

Zhao Y, Hindorff L, Chuang A, Monroe-Augustus M, Lyristis M, Harrison M, Rudolph F, Bennett G (2003). Expression of a cloned cyclopropane fatty acid synthase gene reduces solvent formation in *Clostridium acetobutylicum* ATCC 824. Appl Environ Microbiol, 69:2831-2841.

Zhou J, Zhang H, Zhang Y, Li Y, Ma Y (2012). Designing and creating a modularized synthetic pathway in *cyanobacterium Synechocystis* enables production of acetone from carbon dioxide. Metab Eng. 14(4):394-400.

Zhou J, Li Y (2012a). Engineering cyanobacteria for fuels and chemicals production. Protein Cell. 1(3):207-210. Lathe R, Kieny M P, Skory S, Lecocq J P (1984). Linker tailing: unphosphorylated linker oligonucleotides for joining DNA termini. DNA 3(2): 173-182

Zhu B, Cai G, Hall E O, Freeman G J (2007). In-fusion assembly: seamless engineering of multidomain fusion proteins, modular vectors, and mutations. BioTechniques 43:354-359.

All publications, databases, GenBank sequences, patents and patent applications cited in this Specification are herein incorporated by reference as if each was specifically and individually indicated to be incorporated by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10093922B2). An electronic copy of the "Sequence Listing" will also be available from the USPTO upon request and payment of the fee set forth in 37 CFR 1.19(b)(3).

I claim:

1. A method of producing a polynucleotide library comprising:
   (a) creating a first polynucleotide collection of full-length open reading frames comprising a plurality of polynucleotides having non-homologous sequences identified and isolated from a sequenced genome of a single organism;
   (b) creating a second polynucleotide collection of full-length open reading frames comprising a plurality of polynucleotides having non-homologous sequences identified and isolated from a sequenced genome of a single organism;
   (c) optionally amplifying the isolated polynucleotide sequences of step (a) and/or step (b); and
   (d) joining in-frame in a random manner the collection of step (a) and the collection of step (b) to produce a library comprising a plurality of polynucleotides having sequences different from each other, each polynucleotide comprising a composite single open reading frame formed by at least two non-identical full-length open reading frames, at least one open reading frame originating from step (a) and at least one open reading frame originating from step (b), and encoding a single fusion polypeptide, wherein the at least one open reading frame originating from step (a) and the at least one open reading frame originating from step (b) are not homologous.

2. The method according to claim 1, further comprising inserting the library into an expression vector.

3. The method according to claim 1 or claim 2, wherein the polynucleotide comprising a composite single open reading frame further comprises at least one regulatory sequence.

4. The method according to claim 3, wherein the regulatory sequence is a promoter or a terminator.

5. The method according to claim 1 or claim 2, wherein the composite single open reading frame comprises an open reading frame from step (a) at its 5' end and the composite single open reading frame comprises an open reading frame from step (b) at its 3' end.

6. The method according to claim 1 or claim 2, wherein the composite single open reading frame comprises an open reading frame from step (b) at its 5' end and the composite single open reading frame comprises an open reading frame from step (a) at its 3' end.

7. The method according to claim 1 or claim 2, wherein the at least two open reading frames are joined via a linker sequence.

8. The method according to claim 7, wherein the linker sequence encodes the peptide of SEQ ID NO:25104.

9. The method according to claim 1, wherein the amplification of step (c) uses a primer set comprising a 5' primer comprising 16 nucleotides of sequence homologous to the promoter region of an expression vector and a 3' primer comprising 16 nucleotides of sequence homologous to SEQ ID NO:25103.

10. The method according to claim 1, wherein the amplification of step (c) uses a primer set comprising a 5' primer comprising 16 nucleotides of sequence homologous to SEQ ID NO:25103 and a 3' primer comprising 16 nucleotides homologous to the terminator region of an expression vector.

11. The method according to claim 1, wherein the amplification of step (c) uses a primer set comprising a 5' primer comprising SEQ ID NO:25099 and a 3' primer comprising SEQ ID NO:25100.

12. The method according to claim 1, wherein the amplification of step (c) uses a primer set comprising a 5' primer comprising SEQ ID NO:25101 and a 3' primer comprising SEQ ID NO:25102.

13. The method according to claim 1, wherein the amplification of step (c) uses a primer set comprising a 5' primer comprising SEQ ID NO:25127 and a 3' primer comprising SEQ ID NO:25128.

14. The method according to claim 1, wherein the amplification of step (c) uses a primer set comprising a 5' primer comprising SEQ ID NO:25129 and a 3' primer comprising SEQ ID NO: 25130.

15. The method according to claim 1, wherein the 5' open reading frame is selected from SEQ ID NO:1 to SEQ ID NO:5019.

16. The method according to claim 1, wherein the organism is a yeast, a bacterium, a fungus, a cyanobacterium, an archaeon, an alga, a protozoan, a plant or an animal.

* * * * *